(12) United States Patent
Albers et al.

(10) Patent No.: US 11,459,570 B2
(45) Date of Patent: Oct. 4, 2022

(54) TRANSGENIC MOUSE EXPRESSING AMYLOID PRECURSOR PROTEIN THAT HAS OLFACTORY NEURON DEGENERATION

(71) Applicant: The General Hospital Corporation, Boston, MA (US)

(72) Inventors: Mark William Albers, Winchester, MA (US); Steven Rodriguez, Chelsea, MA (US)

(73) Assignee: The General Hospital Corporation, Boston, MA (US)

( * ) Notice: Subject to any disclaimer, the term of this patent is extended or adjusted under 35 U.S.C. 154(b) by 109 days.

(21) Appl. No.: 16/442,143

(22) Filed: Jun. 14, 2019

(65) Prior Publication Data

US 2019/0352643 A1 Nov. 21, 2019

Related U.S. Application Data

(62) Division of application No. 15/525,396, filed as application No. PCT/US2015/060401 on Nov. 12, 2015, now abandoned.

(60) Provisional application No. 62/078,784, filed on Nov. 12, 2014.

(51) Int. Cl.
| | |
|---|---|
| *A01K 67/027* | (2006.01) |
| *C12N 15/117* | (2010.01) |
| *C07K 14/47* | (2006.01) |
| *A61K 39/395* | (2006.01) |
| *A61K 48/00* | (2006.01) |
| *C12N 15/113* | (2010.01) |

(52) U.S. Cl.
CPC ........ *C12N 15/117* (2013.01); *A01K 67/0275* (2013.01); *A61K 39/39541* (2013.01); *A61K 48/0016* (2013.01); *C07K 14/4711* (2013.01); *C12N 15/113* (2013.01); *A01K 2207/15* (2013.01); *A01K 2217/052* (2013.01); *A01K 2227/105* (2013.01); *A01K 2267/0312* (2013.01); *C12N 2310/17* (2013.01); *C12N 2310/53* (2013.01)

(58) Field of Classification Search
CPC .......... C07K 14/4711; A01K 2227/105; A01K 2267/0312
USPC .......................................................... 800/18
See application file for complete search history.

(56) References Cited

U.S. PATENT DOCUMENTS

| | | |
|---|---|---|
| 6,395,545 B1 | 5/2002 | Monia et al. |
| 2004/0016008 A1 | 1/2004 | Brimijoin et al. |
| 2009/0081128 A1 | 3/2009 | Colton et al. |
| 2010/0069479 A1 | 3/2010 | Tan et al. |
| 2011/0224217 A1 | 9/2011 | Mortensen et al. |
| 2012/0010196 A1 | 1/2012 | Qin |
| 2012/0035187 A1 | 2/2012 | Ohta |
| 2014/0030275 A1 | 1/2014 | Park et al. |

FOREIGN PATENT DOCUMENTS

| | | |
|---|---|---|
| EP | 1063298 | 12/2000 |
| WO | WO 1995/011968 | 5/1995 |
| WO | WO 2008/157208 | 12/2008 |
| WO | WO 2010/040112 | 4/2010 |
| WO | WO 2010/111471 | 9/2010 |
| WO | WO 2015/069647 | 5/2015 |
| WO | WO 2015/187684 | 12/2015 |
| WO | WO 2016/077595 | 5/2016 |
| WO | WO 2017/051188 | 3/2017 |

OTHER PUBLICATIONS

Cheng (J. Neurosci. Sep. 28, 2011, vol. 31, No. 39, p. 13699-13704).*
Kitazawa (Current Pharmaceutical Design, 2012, vol. 18, p. 1131-1147).*
Cao (Nature Communications, 2012, vol. 3, p. 1-19).*
Amit et al., "Unbiased reconstruction of a mammalian transcriptional network mediating pathogen responses," Science, 2009, 326:257-263.
Azorsa et al., "High-content siRNA screening of the kinome identifies kinases involved in Alzheimer's disease-related tau hyperphosphorylation," BMC Genomics 1: 1-10 (2010).
Baruch et al., "Aging-induced type I interferon response at the choroid plexus negatively affects brain function," Science, 2014, 346:89-93.
Bonin et al., "Determination of preferential binding sites for anti-dsRNA antibodies on double-stranded RNA by scanning force microscopy," RNA, 2000, 6: 563-570.
Brenner et al., "Comment on Cutting Edge: Inhibiting TBK1 by Compound II Ameliorates Autoimmune Disease in Mice," J Immunol, 2016, 196(2):530-1.
Brubaker et al., "A Bicistronic MAVS Transcript Highlights a Class of Truncated VAriants in Antiviral Immunity," Cell, 2014, 156(4): 800-811.
Bury et al., "Oligogenic inheritance of optineurin (OPTN) and C9ORF72 mutations in ALS highlights localisation of OPTN in the TDP-43-negative inclusions of C9ORF72-ALS," Neuropathology, 2015, 36: 125-134.
Cao et al., "Aβ alters the connectivity of olfactory neurons in the absence of amyloid plaques in vivo," Nature Communications, 2012, 3: 1-19.
Cao et al., "The precision of axon targeting of mouse olfactory sensory neurons requires the BACE1 protease," Sci Rep., 2012, 2(231):1-8.

(Continued)

*Primary Examiner* — Michael C Wilson
(74) *Attorney, Agent, or Firm* — Fish & Richardson P.C.

(57) ABSTRACT

Methods for treating, and for identifying novel treatments for, neurodegenerative diseases, as well as animal and cellular models.

4 Claims, 15 Drawing Sheets

Specification includes a Sequence Listing.

(56) References Cited

OTHER PUBLICATIONS

Cardin et al., "Driving fast-spiking cells induces gamma rhythm and controls sensory responses," Nature, 2009, 459(7247): 663-667.
Cargnello and Roux, "Activation and function of the MAPKs and their substrates, the MAPK-activated protein kinases," Microbiol Mol Biol Rev, Mar. 2011, 75(1): 50-83.
Castanier et al., "MAVS ubiquitination by the E3 ligase TRIM25 and degradation by the proteasome is involved in type I interferon production after Activation of the antiviral RIG-I-like receptors," BMC Biol, 2012, 10: 44.
Chiang et al., "Complex reorganization and predominat non-homologous repair following chromosomal breakage in karyotypically balances germline rearrangements and transgenic integration," Nat Genet., 2012, 44(4):390-7.
Chiu et al., "A neurodegeneration-specific gene-expression signature of acutely isolated microglia from an amyotrophic lateral sclerosis mouse model," Cell Rep, 2013, 4:385-401.
Cirulli et al., "Exome sequencing in amyotrophic sclerosis identifies risk genes and pathways," Science, 2015, 347: 1436-1441.
Citron et al., "Generation of amyloid beta protein from its precursos is sequence specific," Neuron, Mar. 1995, 14(3): 661-670.
Co et al, Induction of Innate Immune Responses by SIV In Vivo and In Vitro: Differential Expression and Function of RIG-I and MDA5, The Journal of Infectious Diseases , 2011, 204:1104-14 (Year: 2011).
Cooper-Knock et al., "Antisense RNA foci in the motor neurons of C9ORF72-ALS patients are associated with TDP-43 proteinopathy," Acta Neuropathol, 2015.
International Search Report and Written Opinion dated Jun. 27, 2017 in International Application No. PCT/US2017 /025765, 13 pgs.
Davidson et al., "TDP-43 pathological changes in early onset familial and sporadic Alzheimer's disease, late onset Alzheimer's disease and Down's syndrome: association with age, hippocampal sclerosis and clinical phenotype," Acta Neuropathol. 2011, 122(6):703-13.
DeJesus-Hernandez et al., "Expanded GGGGCC hexanucleotide repeat in noncoding region of C9ORF72 causes chromosome 9p-linked FTD and ALS," Neuron, 2011, 72:245-256.
Dickerson et al., "Alzheimer-signature MRI biomarker predicts AD dementia in cognitively normal adults," Neurology, 2011, 76: 1395-1402.
Donato et al., "Differential development of neuronal physiological responsiveness in two human neural stem cell lines," BMC Neurosci, 2007, 8:36.
Donnelly et al., "RNA toxicity from the ALS/FTD C9ORF72 expansion is mitigated by antisense intervention," Neuron, 2013, 80:415-428.
Douville et al., "Identification of active loci of a human endogenous retrovirus in neurons of patients with amyotrophic lateral sclerosis," Annals of Neurology, 2011, 69: 141-151.
Dumurgier et al., "Cerebrospinal fluid PKR level predicts cognitive decline in Alzheimer's disease," PloS one, Jan. 2013, 8: e53587.
Feldman et al., "Novel small molecule inhibitors of 3-phosphoinositide-dependent kinase-1," J Biol Chem, 2005, 280:19867-19874.
Frakes et al., "Microglia induce motor neuron death via the classical NF-kappaB pathway in amyotrophic lateral sclerosis," Neuron, 2014, 81:1009-1023.
Freibaum et al.. "GGGGCC repeat expansion in C9orf72 compromises nucleocytoplasmic transport," Nature, 2015, 525:129-133.
Freischmidt et al., "Haploinsufficiency of TBK1 causes familial ALS and fronto-temporal dementia," Nat. Neurosci. 2015, 18: 631-636.
Gendron et al., "Cerebellar c9RAN proteins associate with clinical and neuropathological characteristics of C9ORF72 repeat expansion carriers," Acta Neuropathol, 2015, 130:559-573.
Geser et al., "Amyotrophic lateral sclerosis, frontotemporal dementia and beyond: the TDP-43 diseases," Journal of Neurology, 2009, 256(8): 1205-1214.

Gitlin et al., "Essential role of mda-5 in type I IFN responses to polyriboinosinic: polyribocytidylic acid and encephalomy ocarditis picomavirus," PNAS, 2006, 103: 8459-8464.
Gogos et al., "Genetic ablation and restoration of the olfactory topographic map," Cell. Nov. 2000, 103(4): 609-620.
Goh et al., "The protein kinase PKR is required for p38 MAPK activation and the innate immune response to bacterial endotoxin," EMBO J, 2000, 19(16): 4292-4297.
Hamel et al., "Biology of Zika Virus Infection in Human Skin Cells," J Virol 89:8880-8896.
Hanscom and Talkowski, "Design of large-insert jumping libraries for structural variant detection using illumina sequencing," Curr Protoc Hum Genet, 2014, 80: 7 22 21-29.
Hasan et al., "Cutting Edge: Inhibiting TBK1 by Compound II Ameliorates Autoimmune Disease in Mice." J Immunol 195: 4573-4577.
Hsiao et al., "Correlative memory deficits, Abeta elevation, and amyloid plaques in transgenic mice," Science, Oct. 1996, 274(5284):99-102.
Hu et al., "Protein kinase and protein phosphatase expression in the central nervous system of G93A mSOD over-expressing mice," J Neurochem, 2003, 85: 422-431.
Imaizumi et al., "MDA5 and ISG56 mediate CXCL10 expression induced by Toll-like receptor 4 activation in U373MG human astrocytoma cells," Neuroscience Research, May 2013,76: 195-206.
International Preliminary Report on Patentability in International Application No. PCT/US2015/060401, dated May 16, 2017, 11 pages.
International Preliminary Report on Patentability in International Application No. PCT/US2017/025765, dated Oct. 11, 2018.
International Search Report and Written Opinion dated Feb. 23, 2016 in International Application No. PCT/US2015/060401, 18 pgs.
Ishibashi et al., "Short RNA duplexes elicit RIG-I-mediated apoptosis in a cell type- and length-dependent manner," Sci Signal. Nov. 2011, 4(198): ra74.
Josephs et al., "Staging TDP-43 pathology in Alzheimer's disease," Acta Neuropathol, Mar. 2014, 127: 441-450.
Jung et al., "TDP-43 in Alzheimer's disease is not associated with clinical FTLD or Parkinsonism," J Neurol, 2014, 261:1344-1348.
Kanaya et al.. "Innate immune responses and neuroepithelial degeneration and regeneration in the mouse olfactory mucosa induced by intranasal administration of Poly(I:C)," Cell Tissue Res, Jul. 2014, 357(1): 279-299.
Kim et al., "A 3D human neural cell culture system for modeling Alzheimer's disease," Nat Protoc, 2015, 10:985-1006.
Kitaguchi et al., "Novel precursor of Alzheimer's disease amyloid protein shows protease inhibitory activity," Nature, Feb. 1988, 331: 530-532.
Lagier-Tourenne et al., "Targeted degradation of sense and antisense C9orf72 RNA foci as therapy for ALS and frontotemporal degeneration," PNAS, Oct. 2013, 110: E4530-4539.
Li et al., "Human endogenous retrovirus-K contributes to motor neuron disease," Sci Transl Med, Sep. 2015, 7: 307ra153.
Li et al., "Optineurin mutations in patients with sporadic amyotrophic lateral sclerosis in China," Amyotrophic Lateral Sclerosis and Frontotemporal Degeneration, 2015, 60:485-489.
Li et al., "Transposable elements in TDP-43-mediated neurodegenerative disorders," PloS one, 2012, 7:e44099.
Liddicoat et al., RNA editing by Ad ADAR1 prevents MDA5 sensing of endogenous dsRNA as nonself, Science, 2015, 349:1115-1120.
Lindahl, "Instability and decay of the primary structure of DNA," Nature, Apr. 1993, 362(6422):709-15.
Ling et al., "Converging mechanisms in ALS and FTD: disrupted RNA and protein homeostasis," Neuron, Aug. 2013, 79: 416-438.
Ling et al.. "TDP-43 repression of nonconserved cryptic exons is compromised in ALS-FTD," Science, Aug. 2015, 349: 650-655.
Liu et al., "Phosphorylation of innate immune adaptor proteins MAVS, STING, and TRIF induces IRF3 activation," Science, 2015, 347:aaa2630.
Lodato et al., "Somatic mutation in single human neurons tracks developmental and transcriptional history," Science, Oct. 2015, 350: 94-98.

(56) References Cited

OTHER PUBLICATIONS

Lu et al., "Gene regulation and DNA damage in the ageing human brain," Nature, Jun. 2004, 429(6994):883-91.
Madabhushi et al., "DNA damage and its links to neurodegeneration," Neuron. Jul. 2014, 83(2): 266-282.
May et al., "C9orf72 FTLD/ALS-associated Gly-Ala dipeptide repeat proteins cause neuronal toxicity and Unc119 sequestration," Acta Neuropathol, 2014, 128:485-503.
McAllister and Samuel, "The RNA-activated protein kinase enhances the induction of Interferon-beta and apoptosis mediated by cytoplasmic RNA sensors," The Journal of Biological Chemistry, Jan. 2009, 284: 1644-1651.
McConnell et al., "Mosaic Copy Number Variation in Human Neurons," Science. Nov. 2013. 342(6158):632-7.
Melton et al., "Chronic glial activation, neurodegeneration, and APP immunoreactive deposits following acute administration of double-stranded RNA," Glia, Oct. 2003, 44(1): 1-12.
Mizielinska et al., "C9orf72 frontotemporal lobar degeneration is characterised by frequent neuronal sense and antisense RNA foci," Acta Neuropathol, 2013, 126(6): 845-857.
Mizielinska et al., "C9orf72 repeat expansions cause neurodegeneration in *Drosophila* through arginine-rich proteins," Science, 2014, 345:1192-1194.
Mlakar et al., "Zika Virus Associated with Microcephaly," N Engl J Med, 2016, 374:951-958.
Morel et al., "PKR, the double stranded RNA-dependent protein kinase as a critical target in Alzheimer's disease," J. Cell. Mol. Med. 13: 1476-1488 (2009).
Mouton-Liger et al., "Increased cerebrospinal fluid levels of double-stranded RNA-dependant protein kinase in Alzheimer's disease," Biological Psychiatry, May 2012, 71: 829-835.
Mukherjee et al., "Activation of the innate signaling molecule MAVS by bunyavirus infection upregulates the adaptor protein SARM1. leading to neuronal death," Immunity, 2013, 38: 705-716.
Mukherjee et al., "SARM1, Not MyD88, Mediates TLR7/TLR9-Induced Apoptosis in Neurons," J Immunol, 2015, 195:4913-4921.
Mullan et al., "A pathogenic mutation for probable Alzheimer's disease in the APP gene at the N-terminus of beta-amyloid," Nat Genet. Aug. 1992, 1(5): 345-347.
Nallagatla et al., "Regulation of innate immunity through RNA structure and the protein kinase PKR," Curr Opin Struct Biol, Feb. 2011, 21(1): 119-127.
Ou et al., "TBK1 Directly Engages Akt/PKB Survival Signaling to Support Oncogenic Transformation," Mol Cell, 2011, 41(41:458-70.
Paré et al., "Early detection of structural abnormalities and cytoplasmic accumulation of TDP-43 in tissue engineered skins derived from ALS patients," Acta Neuropathol Commun, 2015, 3:5.
Peisley et al., "Cooperative assembly and dynamic disassembly of MDA5 filaments for viral dsRNA recognition," PNAS, Dec. 2011,108(52): 21010-21015.
Platanias et al., "The p38 mitogen-activated protein kinase pathwav and its role in interferon signaling," Pharmacol Ther., May 2003, 98(2):129-42.
Polymenidou et al., "Long pre-mRNA depletion and RNA missplicing contribute to neuronal vulnerability from loss of TDP-43," Nature Neuroscience, 2011, 14:459-468.
Ponte et al., "A new A4 amyloid mRNA contains a domain homologous to serine proteinase inhibitors," Nature, Feb. 1988, 331: 525.
Pottier et al., "Whole-genome sequencing reveals important role for TBK1 and OPTN mutations in frontotemporal lobar degeneration without motor neuron disease," Acta Neuropathol. 2015, 130: 77-92.
Rao et al., "Neuroinflammation and synaptic loss," Neurochemical Research. May 2012, 37: 903-910.
Reilly et al., "The role of transposable elements in health and diseases of the central nervous system," The Journal of Neuroscience, Nov. 2013, 33: 17577-17586.
Renton et al., "A hexanucleotide repeat expansion in C9ORF72 is the cause of chromosome 9p21-linked ALS-FTD," Neuron, 2011, 72:257-268.
Rongvaux et al., "Apoptotic caspases prevent the induction of type I interferons by mitochondrial DNA," Cell, 2014, 159:1563-1577.
Rubin et al., "Zika Virus and Microcephaly," N Engl J Med, 2016, 2 pages.
Sakaguchi et al., "Optineurin with amyotrophic lateral sclerosis-related mutations abrogates inhibition of interferon regulatory factor-3 activation," Neurosci Lett, 2011, 505:279-281.
Saldi et al., "TDP-1, the Caenorhabditis elegans ortholog of TDP-43. limits the accumulation of double-stranded RNA," The EMBO Journal, 2014, 33: 2947-2966.
Sareen et al., "Targeting RNA foci in iPSC-derived motor neurons from ALS patients with a C9ORF72 repeat expansion," Sci Transl Med, 2013, 5:208ra149.
Savva et al., "The ADAR protein family," Genome Biol. 2012. 13(12): 252.
Scheuner et al., "The double-stranded RNA-activated protein kinase mediates viral-induced encephalitis," Virology, 2003, 317:263-274.
Shykind et al., "Gene switching and the stability of odorant receptor gene choice." Cell, 2004, 117(6): 801-815.
Suzuki et al., "Increased expression of TDP-43 in the skin of amyotropliic lateral sclerosis," Acta Neurol Scand, 2010, 122(5):367-72.
Takeuchi and Akira, "Pattern recognition receptors and inflammation," Cell, Mar. 2010. 140(6): 805-820.
Talkowski et al., "Sequencing chromosomal abnormalities reveals neurodevelopmental loci that confer risk across diagnostic boundaries," Cell, Apr. 2012, 149: 525-537.
Tu et al., "Structure and ubiquitination-dependent activation of TANK-binding kinase 1," Cell Rep, 2013, 3:747-758.
Vedin et al., "Regional differences in olfactory epithelial homeostasis in the adult mouse," J Comp Neurol, Apr. 2009, 513(4): 375-384.
Wen et al., "Antisense proline-arginine RAN dipeptides linked to C9ORF72-ALS/FTD form toxic nuclear aggregates that initiate in vitro and in vivo neuronal death," Neuron, 2014, 84:1213-1225.
Wu et al., "Structural basis for dsRNA recognition, filament formation, and antiviral signal activation by MDA5," Cell, 2013, 152(1-2): 276-289.
Yu et al., "Spontaneous neural activity is required for the establishment and maintenance of the olfactoiy sensory map," Neuron, 2004, 42(4): 553-566.
Zhang et al., "Integrated systems approach identifies genetic nodes and networks in late-onset Alzheimer's disease," Cell, 2013, 153: 707-720.
Zhu et al., "Suppression of PKR promotes network excitability and enhanced cognition by interferon-gamma-mediated disinhibition," Cell, 2011, 147:1384-1396.
CAS No. 457081-03-7, "JAK inhibitor I, Calcbiochem," Millipore Sigma, retrieved on Apr. 27, 2021 retrieved from URL <https://www.emdmillipore.com/US/en/product/JAK-Inhibitor-I-CAS-457081-03-7-Calbiochem,EMD_BIO-420099?ReferrerURL=https%3A%2F%2Fwww.google.com%2F&bd=1>, 3 pages.
Liu et al., "Therapeutic Efficacy of Suppressing the JAK/STAT Pathway in Multiple Models of Experimental Autoimmune Encephalomyelitis," J Immunol., 2014, 192(1):59-72.
Ning et al., "Epigallocatechin-3-gallate (EGCG) Suppresses the Trafficking of Lymphocytes to Epidermal Melanocytes via Inhibition of JAK2: Its Implication for Vitiligo Treatment," Biol. Pharm. Bull., 2015, 38(11):1700-1706.
Przedborski et al., "Series Introduction: Neurodegeneration: What is it and where are we?" J. Clin Invest., 2003, 111(1):3-10.
Qin et al., "Inhibition of the JAK/STAT Pathway Protects Against α-Synuclein-Induced Neuroinflammation and Dopaminergic Neurodegeneration," The Journal of Neuroscience, May 2016, 36(18):5144-5159.

\* cited by examiner

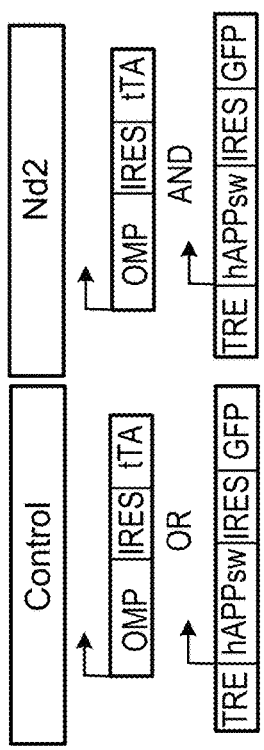
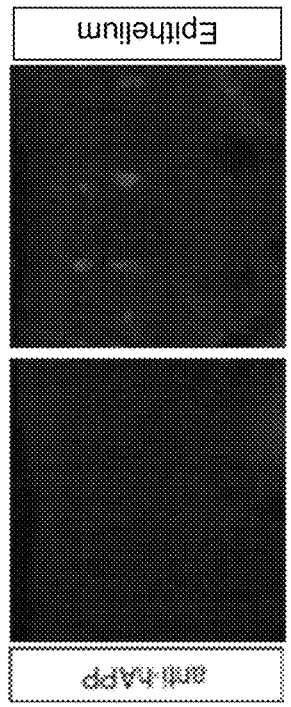
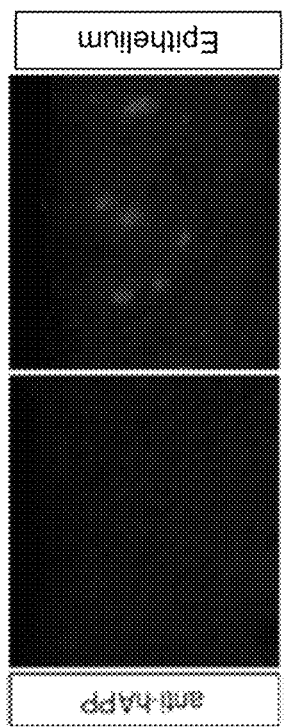
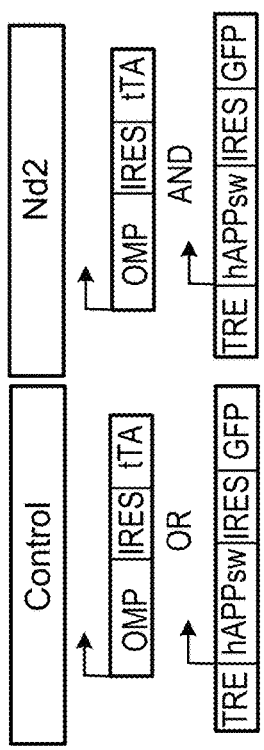
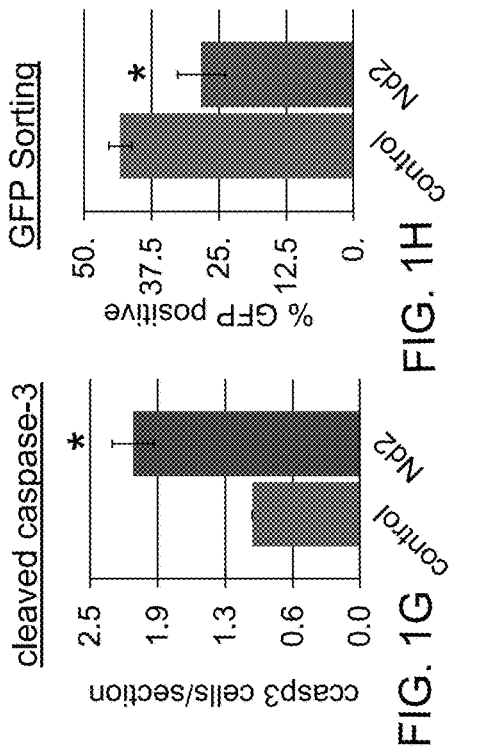
FIG. 1A  FIG. 1B  FIG. 1C  FIG. 1D  FIG. 1E  FIG. 1F  FIG. 1G  FIG. 1H

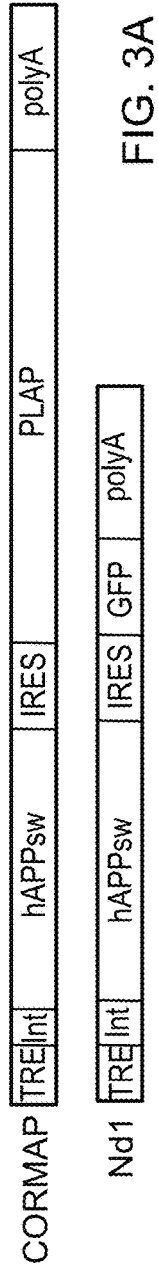
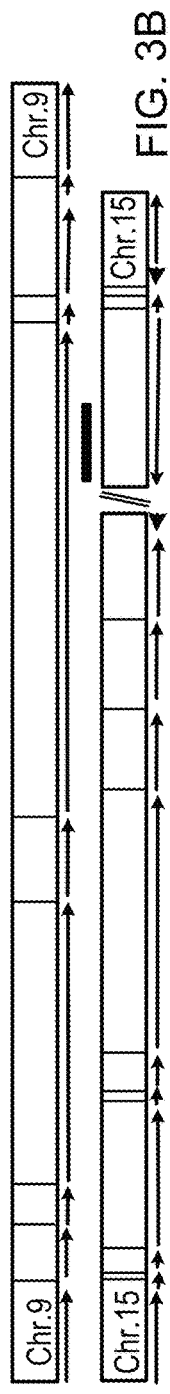
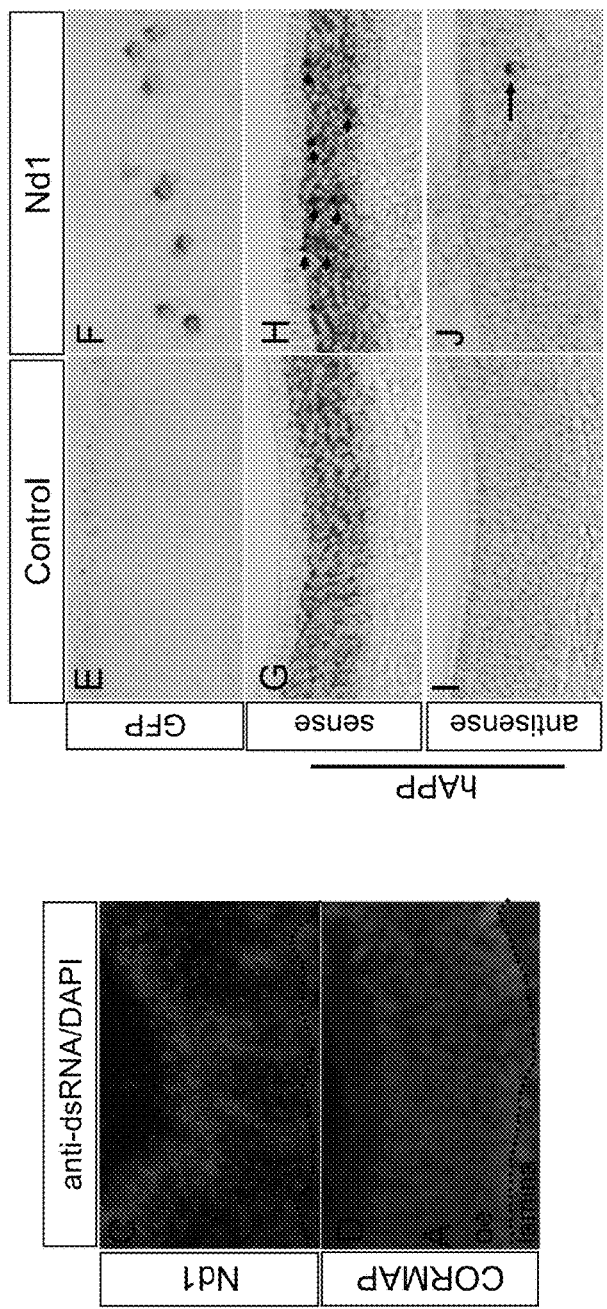
FIG. 3A
FIG. 3B
FIG. 3C
FIG. 3D
FIG. 3E-3J

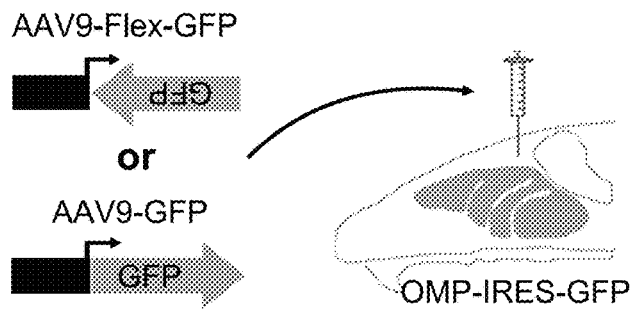
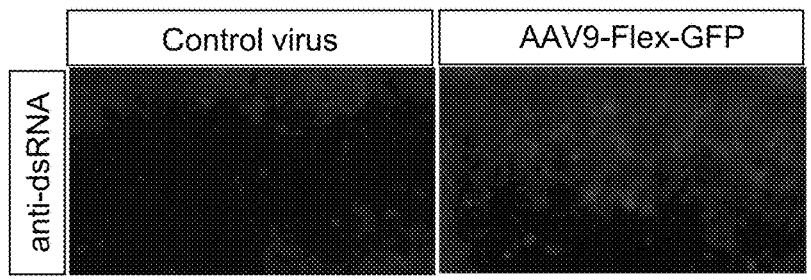
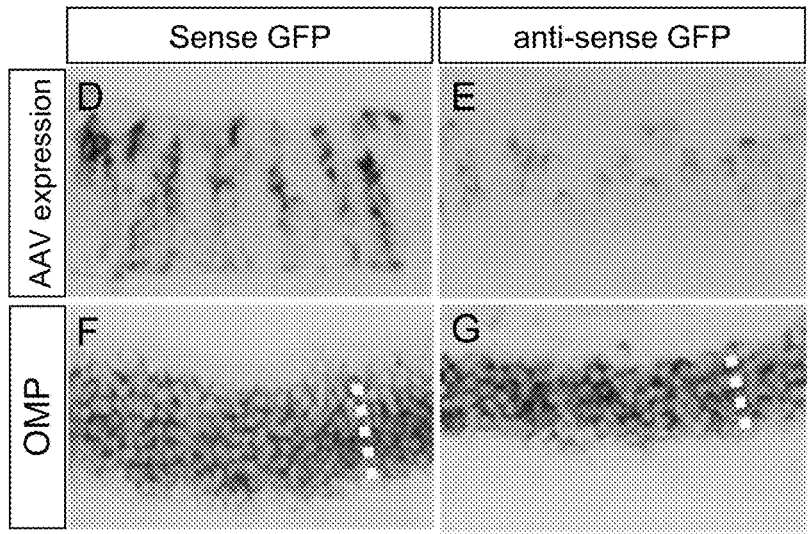
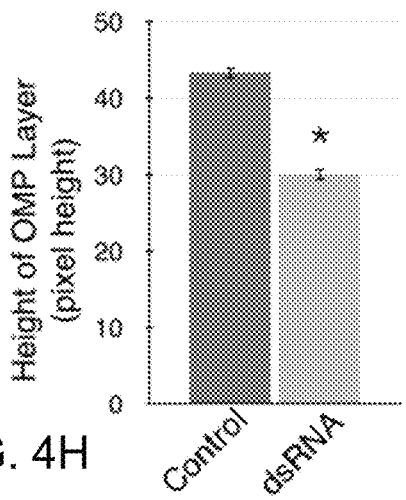
FIG. 4A
FIG. 4B
FIG. 4C
FIG. 4D-4G
FIG. 4H

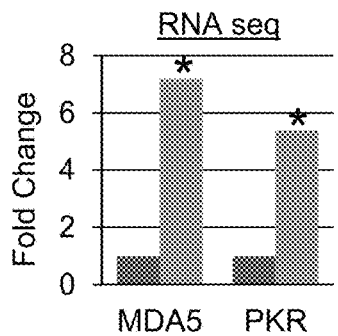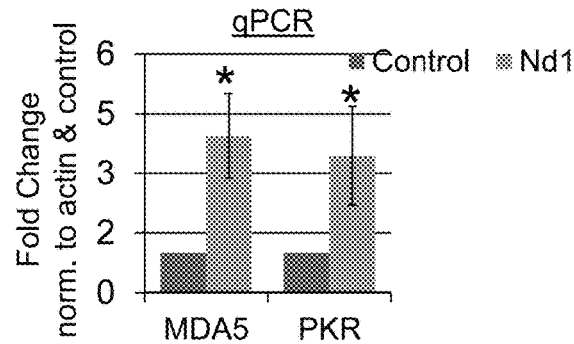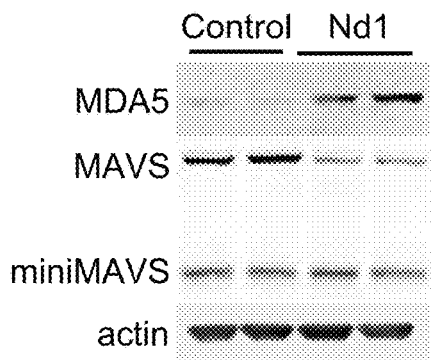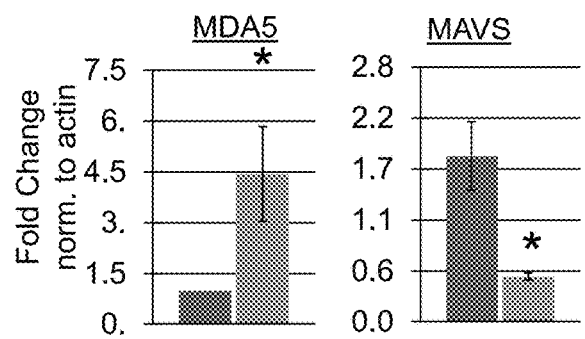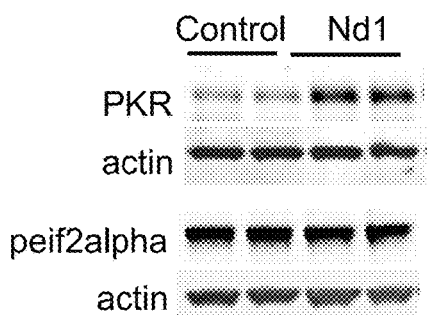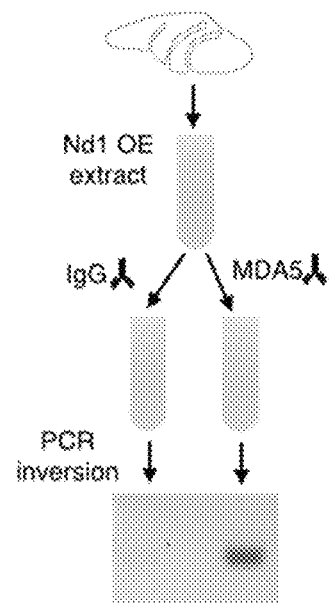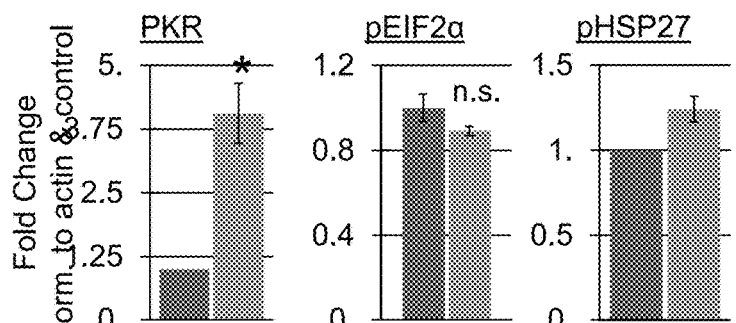

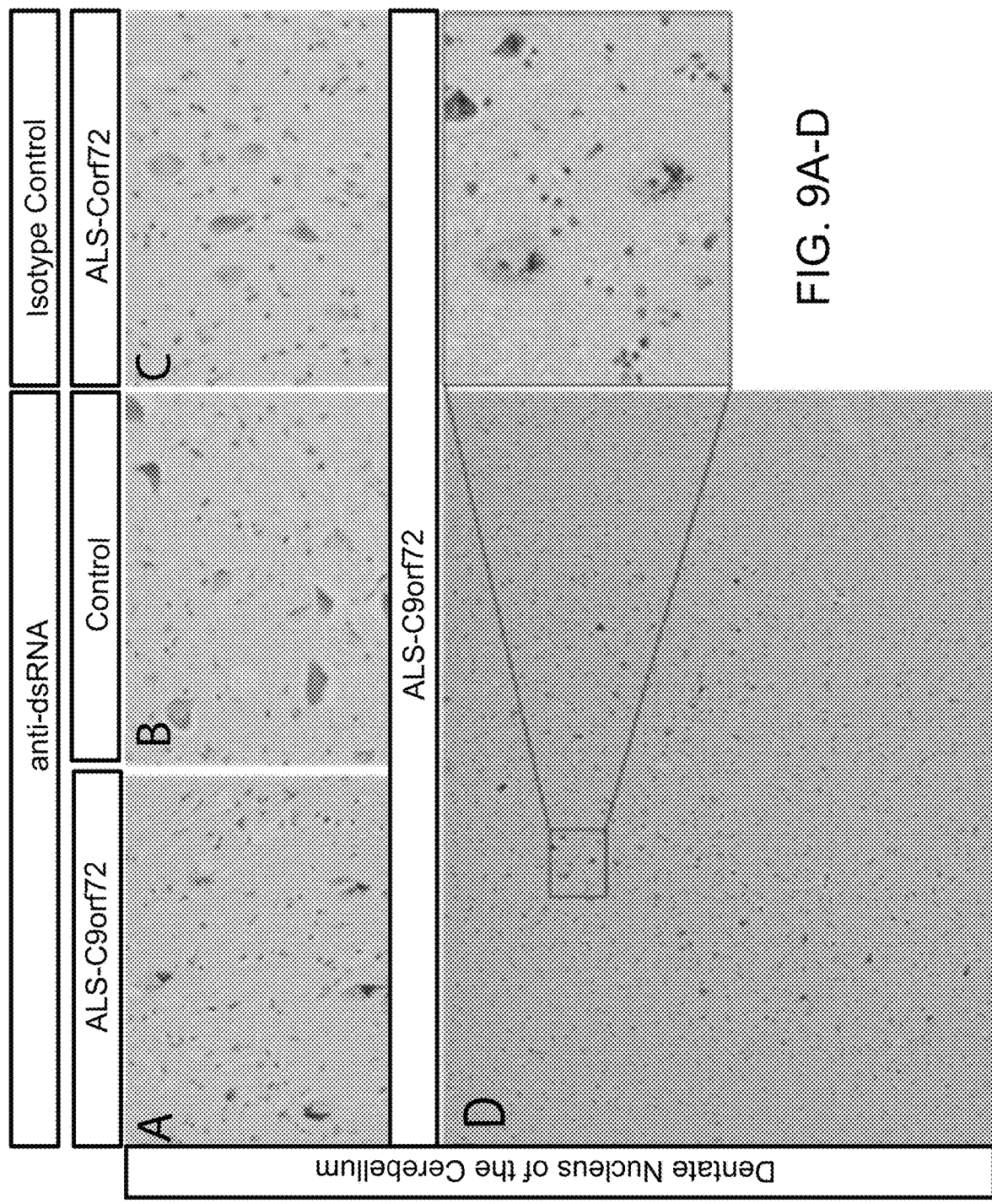
FIG. 9A-D

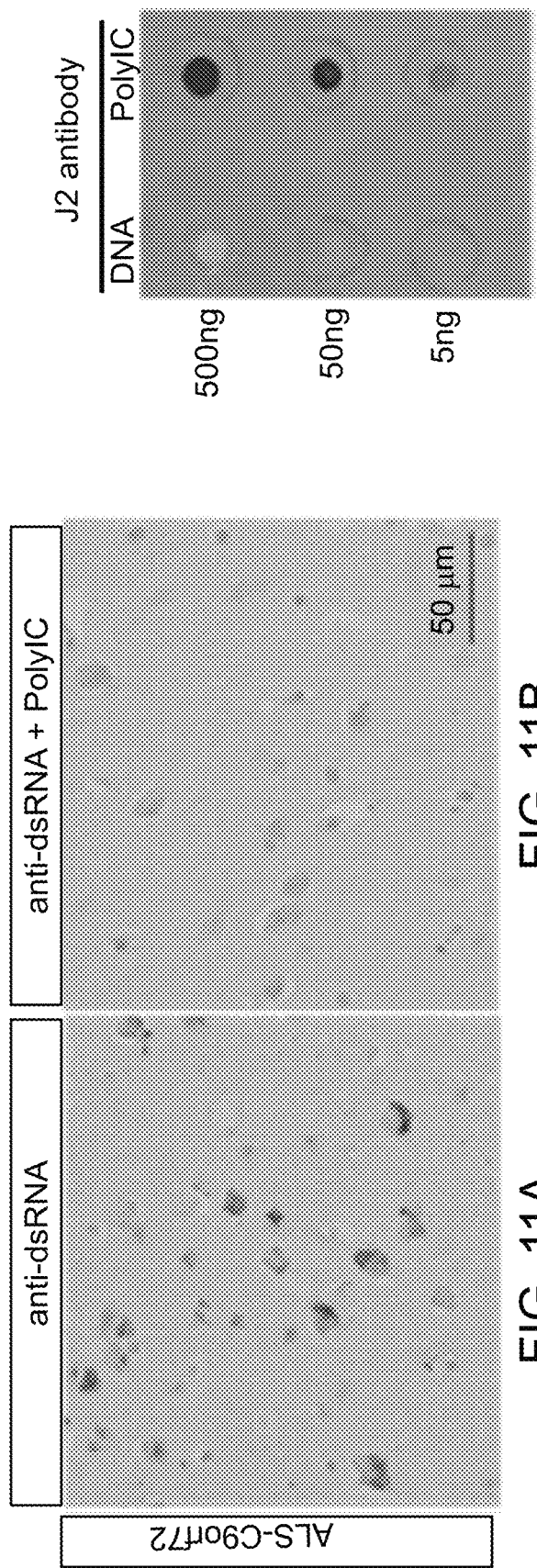

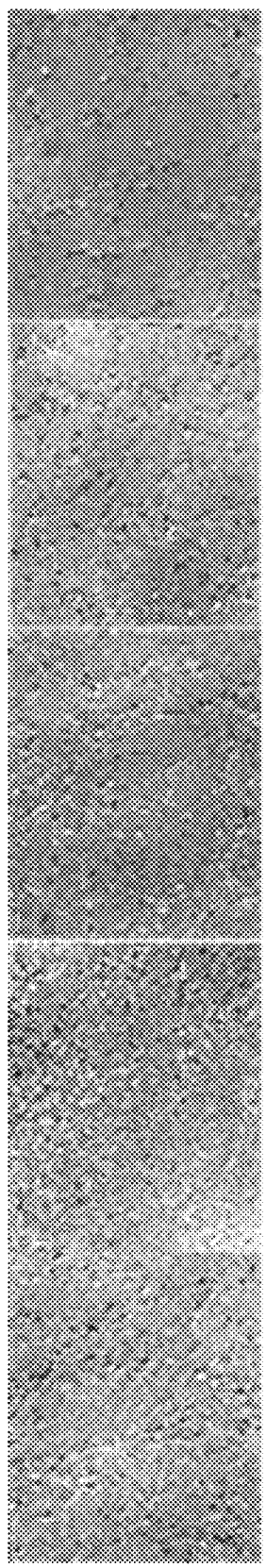
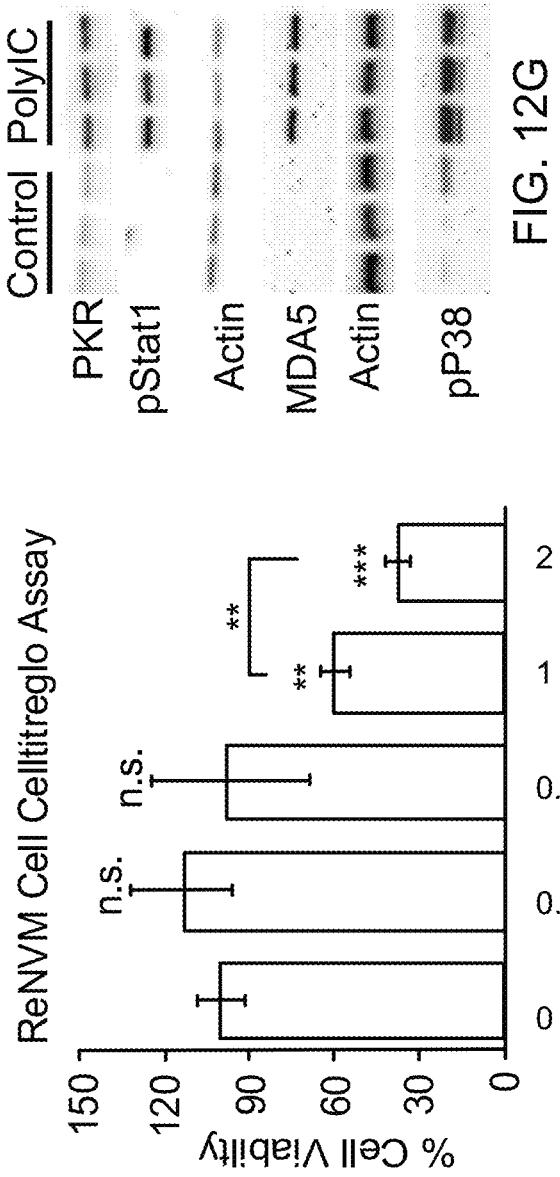
FIG. 12A  FIG. 12B  FIG. 12C  FIG. 12D  FIG. 12E
FIG. 12F
FIG. 12G

SEQUENCE LISTING

```
<160> NUMBER OF SEQ ID NOS: 22

<210> SEQ ID NO 1
<211> LENGTH: 20
<212> TYPE: DNA
<213> ORGANISM: Artificial Sequence
<220> FEATURE:
<223> OTHER INFORMATION: synthetically generated primer

<400> SEQUENCE: 1
ctgaaagagg gcttccaggg                                              20

<210> SEQ ID NO 2
<211> LENGTH: 20
<212> TYPE: DNA
<213> ORGANISM: Artificial Sequence
<220> FEATURE:
<223> OTHER INFORMATION: synthetically generated primer

<400> SEQUENCE: 2
```

```
atgcctccag cttggacttc                                               20

<210> SEQ ID NO 3
<211> LENGTH: 20
<212> TYPE: DNA
<213> ORGANISM: Artificial Sequence
<220> FEATURE:
<223> OTHER INFORMATION: synthetically generated primer

<400> SEQUENCE: 3
tgcctgggag agaatcgaga                                               20

<210> SEQ ID NO 4
<211> LENGTH: 20
<212> TYPE: DNA
<213> ORGANISM: Artificial Sequence
<220> FEATURE:
<223> OTHER INFORMATION: synthetically generated primer

<400> SEQUENCE: 4
agatgcagat gtcgcggtag                                               20

<210> SEQ ID NO 5
<211> LENGTH: 20
<212> TYPE: DNA
<213> ORGANISM: Artificial Sequence
<220> FEATURE:
<223> OTHER INFORMATION: synthetically generated primer

<400> SEQUENCE: 5
aagtctggca gctgagttcc                                               20

<210> SEQ ID NO 6
<211> LENGTH: 20
<212> TYPE: DNA
<213> ORGANISM: Artificial Sequence
<220> FEATURE:
<223> OTHER INFORMATION: synthetically generated primer

<400> SEQUENCE: 6
tacttcccaa aggcgtggtc                                               20

<210> SEQ ID NO 7
<211> LENGTH: 22
<212> TYPE: DNA
<213> ORGANISM: Artificial Sequence
<220> FEATURE:
<223> OTHER INFORMATION: synthetically generated primer

<400> SEQUENCE: 7
acttcagaga tctcctccgt ct                                            22

<210> SEQ ID NO 8
<211> LENGTH: 20
<212> TYPE: DNA
<213> ORGANISM: Artificial Sequence
<220> FEATURE:
<223> OTHER INFORMATION: synthetically generated primer

<400> SEQUENCE: 8
gggaagaggc agaacgtcaa                                               20

<210> SEQ ID NO 9
<211> LENGTH: 21
<212> TYPE: DNA
```

<213> ORGANISM: Artificial Sequence
<220> FEATURE:
<223> OTHER INFORMATION: synthetically generated primer

<400> SEQUENCE: 9
atgcacggag tagccattac g                                    21

<210> SEQ ID NO 10
<211> LENGTH: 22
<212> TYPE: DNA
<213> ORGANISM: Artificial Sequence
<220> FEATURE:
<223> OTHER INFORMATION: synthetically generated primer

<400> SEQUENCE: 10
tgacaatcca ccttgttttc gt                                   22

<210> SEQ ID NO 11
<211> LENGTH: 23
<212> TYPE: DNA
<213> ORGANISM: Artificial Sequence
<220> FEATURE:
<223> OTHER INFORMATION: synthetically generated primer

<400> SEQUENCE: 11
gccgctaaac ttgcatatct tca                                  23

<210> SEQ ID NO 12
<211> LENGTH: 23
<212> TYPE: DNA
<213> ORGANISM: Artificial Sequence
<220> FEATURE:
<223> OTHER INFORMATION: synthetically generated primer

<400> SEQUENCE: 12
tcacacgtag tagcaaaaga acc                                  23

<210> SEQ ID NO 13
<211> LENGTH: 22
<212> TYPE: DNA
<213> ORGANISM: Artificial Sequence
<220> FEATURE:
<223> OTHER INFORMATION: synthetically generated primer

<400> SEQUENCE: 13
aagagccaga gtgtcagaat ct                                   22

<210> SEQ ID NO 14
<211> LENGTH: 23
<212> TYPE: DNA
<213> ORGANISM: Artificial Sequence
<220> FEATURE:
<223> OTHER INFORMATION: synthetically generated primer

<400> SEQUENCE: 14
agctccagtt ggtaatttct tgg                                  23

<210> SEQ ID NO 15
<211> LENGTH: 21
<212> TYPE: DNA
<213> ORGANISM: Artificial Sequence
<220> FEATURE:
<223> OTHER INFORMATION: synthetically generated primer

<400> SEQUENCE: 15
ctggacccta cctacatcct g                                    21

<210> SEQ ID NO 16
<211> LENGTH: 19
<212> TYPE: DNA
<213> ORGANISM: Artificial Sequence
<220> FEATURE:
<223> OTHER INFORMATION: synthetically generated primer

<400> SEQUENCE: 16
ggcatccaaa aagccacgg                                            19

<210> SEQ ID NO 17
<211> LENGTH: 23
<212> TYPE: DNA
<213> ORGANISM: Artificial Sequence
<220> FEATURE:
<223> OTHER INFORMATION: synthetically generated primer

<400> SEQUENCE: 17
agatcaacac ctgtggtaac acc                                       23

<210> SEQ ID NO 18
<211> LENGTH: 20
<212> TYPE: DNA
<213> ORGANISM: Artificial Sequence
<220> FEATURE:
<223> OTHER INFORMATION: synthetically generated primer

<400> SEQUENCE: 18
ctctagggcc tccacgaaca                                           20

<210> SEQ ID NO 19
<211> LENGTH: 22
<212> TYPE: DNA
<213> ORGANISM: Artificial Sequence
<220> FEATURE:
<223> OTHER INFORMATION: synthetically generated primer

<400> SEQUENCE: 19
tcgaatgggt attccacaga cg                                        22

<210> SEQ ID NO 20
<211> LENGTH: 19
<212> TYPE: DNA
<213> ORGANISM: Artificial Sequence
<220> FEATURE:
<223> OTHER INFORMATION: synthetically generated primer

<400> SEQUENCE: 20
gtggcgactg tcctctgaa                                            19

<210> SEQ ID NO 21
<211> LENGTH: 20
<212> TYPE: DNA
<213> ORGANISM: Artificial Sequence
<220> FEATURE:
<223> OTHER INFORMATION: synthetically generated primer

<400> SEQUENCE: 21
actggtggaa ttgcctgcat                                           20

<210> SEQ ID NO 22
<211> LENGTH: 20
<212> TYPE: DNA
<213> ORGANISM: Artificial Sequence
<220> FEATURE:

```
<223> OTHER INFORMATION: synthetically generated primer

<400> SEQUENCE: 22
aaggagacag ctcgggtact                                              20
```

TRANSGENIC MOUSE EXPRESSING AMYLOID PRECURSOR PROTEIN THAT HAS OLFACTORY NEURON DEGENERATION

CLAIM OF PRIORITY

This application is a divisional of U.S. patent application Ser. No. 15/525,396, filed May 9, 2017, which is a § 371 National Stage Application of PCT/US2015/060401, filed Nov. 12, 2015, which claims the benefit of U.S. Provisional Patent Application Ser. No. 62/078,784, filed on Nov. 12, 2014. The entire contents of the foregoing are hereby incorporated by reference.

FEDERALLY SPONSORED RESEARCH OR DEVELOPMENT

This invention was made with Government support under Grant Nos. NIH DP2-OD006662, K08 DC4807, P30-AG036449, and P50-005134 awarded by the National Institutes of Health. The Government has certain rights in the invention.

TECHNICAL FIELD

Described herein are methods for treating, and for identifying novel treatments for, neurodegenerative diseases, as well as animal and cellular models.

BACKGROUND

Aging is necessary for all sporadic, and nearly all genetic, neurodegenerative diseases and is the most significant risk factor for Alzheimer's disease (AD). The biology underlying aging in the human brain remains poorly understood. One seminal study of gene expression in the aging human brain found that DNA repair enzymes were the class of genes with the greatest increase after the age of 40 (Lu et al., Nature. 2004; 429(6994):883-91). It is estimated that each genome in every cell of the human body undergo 10,000 lesions per day (Lindahl, Nature. 1993; 362(6422):709-15). In higher order mammals, particularly in post-mitotic cells, such as neurons, the predominant mechanism of repairing double strand breaks is non-homologous end-joining (NHEJ). As opposed to homologous repair, any two exposed ends formed by a double strand break can be fused together, potentially introducing structural rearrangements in chromosomes. Recent advances in genomic sequencing have revealed that the structures and sequences of the genomes in about half of individual frontal lobe neurons from the same healthy 20 year old individuals are not identical (McConnell et al., Science. 2013; 342(6158):632-7; Lodato et al., Science 2015; 350: 94-98) and that structural alterations in the genome (balanced shuffling of intact pieces of the genome or additions/subtractions of segments of the genome) are enriched in people with cognitive dysfunction and neurodevelopmental disorders (Chiang et al., Nat Genet. 2012; 44(4):390-7, S1). In separate studies, converging evidence indicate that innate immune signaling (Zhang et al., Cell. 2013; 153(3):707-20), discovered as a means to combat infections, play an instrumental, and perhaps causal, role in neurodegenerative diseases.

SUMMARY

The present disclosure shows that age dependent accumulation of genomic lesions leads to the production of RNA molecules within neurons that mimic viruses and intrinsically activate innate immune signaling, which triggers neurodegeneration. This hypothesis is supported by the results shown herein elucidating the mechanism of neurodegeneration in two mouse lines that specifically express different isoforms of the human amyloid precursor protein (hAPP) gene, which is associated with Alzheimer's disease (AD), exclusively in olfactory sensory neurons (OSNs) in the nose.

Thus, in a first aspect, provided herein are methods for treating a neurodegenerative disease in a subject in need thereof, e.g., a mammal, e.g., a human. The methods include administering to the subject a therapeutically effective amount of one or more of a small molecule inhibitor of a protein listed in Table A; an inhibitory nucleic acid that targets a transcript listed in Table A; and/or an antibody that binds to and inhibits a protein listed in Table A; thereby treating the neurodegenerative disease in the subject.

In some embodiments, the neurodegenerative disease is Alzheimer's disease, amyotrophic lateral sclerosis (e.g., C9orf72-linked ALS, fused in sarcoma (FUS)-linked ALS, TAR DNA-binding protein 43 (TDP-43)-linked ALS, C9orf72-linked frontotemporal dementia (FTD), FUS-linked FTD, and TDP-43-linked FTD, C9orf72-linked AD, or sporadic ALS), frontotemporal dementia, Cockayne Syndrome (CS), Xeroderma Pigmentosum (XP), Trichothiodystrophy (TTD), Ataxia with Occulomotor Apraxia-1 (AOA1), Spinocerebellar Ataxia with Axonal Neuropathy (SCAN1), Ataxia Telangiectasia (A-T) or A-T Like Disease (ATLD), ATR-Seckel Syndrome, Nijmegen Breakage Syndrome (NBS), LIG4 Syndrome, or XLF Syndrome.

In another aspect, provided herein are methods for identifying candidate compounds for treating a neurodegenerative disease. These in vitro methods include providing a cell, e.g., a neuron, that expresses an antisense transcript that is at least 35 nt long and is complementary to a sense transcript that is expressed in the cell, wherein expression of the antisense in the absence of a test compound results in apoptosis in the cell, and the apoptosis occurs via induction of Type 1 interferon signaling; contacting the cell with a test compound; measuring apoptosis in the presence of the test compound, and selecting a test compound that reduces or delays apoptosis as a candidate compound for treating a neurodegenerative disease.

In some embodiments, the antisense coding sequence is under the control of an inducible promoter and the method includes inducing expression of the antisense in the cell.

In some embodiments, the antisense is complementary to an endogenous sense transcript or to a sense transcript that is expressed from an exogenous coding sequence.

In some embodiments, the cell is in a three-dimensional culture system.

In another aspect, provided are methods for identifying a candidate compound for treating a neurodegenerative disease. The methods include expressing in an animal model an antisense transcript that leads to production of a dsRNA molecule, e.g., in the olfactory sensory neurons (OSNs) of the animal, administering a test compound to the animal, and evaluating apoptosis, e.g., in the OSNs of the animal, and selecting a test compound that reduces or delays apoptosis as a candidate compound for treating a neurodegenerative disease.

Also provided herein are animal models of neurodegenerative disease as described herein, e.g., the Nd1, Nd2, or Nd3 mice. In some embodiments the mouse is an Nd2 transgenic mouse, which has incorporated into its genome a transgene driven by the tetracycline responsive element (TRE) that expresses a synthetic allele of hAPP with an M to V amino acid substitution at position 671 (M671V) followed by an internal ribosome entry sequence (IRES), and the fluorescent marker mCherry (hAPPmv-IRES-mCherry), with an additional insertion of an inversion of part of the hAPP coding region. Also described herein is the Nd1 mouse, which has incorporated into its genome a transgene driven by the TRE that expresses the Swedish isoform of hAPP (K670N, M671L), which is believed to cause AD by enhancing the production of the amyloid-β (Aβ) peptide, and the fluorescent marker GFP (hAPPsw-IRES-GFP). In some embodiments, the transgenic mouse has incorporated into its genome a transgene driven by the TRE that expresses a pathogenic Swedish allele of human APP with an M to V amino acid substitution at positions 670 and 671 (K670N, M671L) coupled to an internal ribosome entry sequence (IRES), and the fluorescent markerGFP (hAPPsw-IRES-GFP), with an additional insertion of an inversion of part of the transgene. Also described herein is the Nd3 transgenic mouse, which has incorporated into its genome a transgene driven by the TRE that expresses a wild type allele of human APP followed by an internal ribosome entry sequence (IRES), and the fluorescent marker GFP (hAPPwt-IRES-GFP), with an additional insertion of an inversion of part of the transgene.

Unless otherwise defined, all technical and scientific terms used herein have the same meaning as commonly understood by one of ordinary skill in the art to which this invention belongs. Methods and materials are described herein for use in the present invention; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

Other features and advantages of the invention will be apparent from the following detailed description and figures, and from the claims.

DESCRIPTION OF DRAWINGS

FIGS. 1A-H. Expression of the transgene in the Nd1 and the Nd2 mouse lines is sufficient to induce increased apoptosis and a significant loss of mature OSNs, independent of transgenic integration into the genome. A) A schematic showing the Nd1 transgenic construct; hAPPsw and GFP, and B) the Nd2 transgenic construct; hAPPmv and mCherry, which are co-expressed with an IRES sequence that was placed under the transcriptional control of the tetracycline-responsive promoter element (TRE). The tetracycline-controlled transactivator protein is under the control of the endogenous OMP promoter, thereby restricting transgene expression to mature OSNs. We used animals with the transgene alone, or animals expressing tTA alone littermates as controls. C, D) Sparse transgene expression shown by tyramide amplified immunofluorescent staining with an antibody specific to hAPP (6E10, red in original) and the nuclear marker DAPI (blue in original). Quantitation of the number of cleaved-caspase3 (CCASP3) positive cells per section, normalized to littermate controls in Nd1 (middle bar) (p=0.01, n=5) (E) or for animals fed food containing doxycycline for three months (light grey bar at right) (p=0.25, n=3), and (G) Nd2 (p=0.003, n=5). Percentage of GFP positive cells in olfactory epithelial quantified by FACS analysis, in (F) Nd1 and littermate controls (p<0.0001, n=4), and (H) Nd2 and littermate controls (p=0.02, n=3).

FIGS. 3A-J. Chromothripsis in Nd1, but not CORMAP. A) schematics (1 pixel/nucleotide, then scaled) showing CORMAP and Nd1 transgene sequences that were injected into mice, as determined by Sanger sequencing. B) schematics (1 pixel/nucleotide, then scaled) of integrated transgenic sequences and their chromosomal locations (flanking black boxes), as determined by sequencing of whole genome jumping libraries and confirmed by Sanger sequencing. DsRNA, detected by immunofluorescence staining with the J2 antibody, is present in Nd1 (C), but not in CORMAP (D). RNA in situ hybridization with an anti-sense probe for GFP expression (E,F), an anti-sense probe for antisense APP (G,H), which recognizes both mouse and human APP (red arrows, H), and an sense probe that recognizes antisense hAPP (I,J).

FIGS. 4A-H. DsRNA is sufficient to induce neuronal olfactory sensory neuron death. A) A schematic showing an example of AAV9-FLEX-GFP (anti-sense GFP) or AAV9-GFP viruses applied to the olfactory epithelium of OMP-IRES-GFP mice. We infected OMP-IRES-tTA mice with the AAV-FLEX-GFP virus (n=2), or OMP-IRES-GFP mice with AAV-GFP (n=2) as controls. C) OMP-IRES-GFP mice infected with AAV-FLEX-GFP form dsRNA, B) but not mice expressing GFP infected with AAV-GFP. D,E) RNA in situ hybridzation shows that anti-sense GFP is expressed in mice infected with AAV-FLEX-GFP. H) Quantitation of OSN loss in dsRNA containing mice relative to control mice (p<0.0001, n=121 measurements from controls, n=138 from dsRNA mice).

FIGS. 6A-G. Double-stranded RNA cytoplasmic recognition receptors in Nd1. A) RNA-seq data showing the increased expression of PKR and MDA5 (IFIH1) in Nd1. B) qPCR showing increased expression of PKR and MDA5 in Nd1 relative to littermate controls. C) Western blots showing increased MDA5 protein expression, the degradation of the large isoform of MAVS, but not miniMAVS, and actin as an internal control, quantitated in (D) (MDA5 p=0.04,n=5; MAVS p=0.01, n=3). E) PKR protein expression and phosphorylated HSP27 are increased in Nd1 and controls, but not pEIF2a, quantitated in (F) (PKR p=0.006, n=3; pEIF2a p=0.37, n=3; pHSP27, n=3). G) RNA co-immunoprecipitation of Nd1 extracts with an antibody against MDA5 or IgG at the same concentration. PCR of the extracts for hAPP reveal a clear enrichment in MDA5 pulldowns relative to control IgG pulldown (n=3 mice).

FIG. 9A-D. Neurons in ALS-C9orf72 cases contain high levels of dsRNA in the dentate nuclei of the cerebellar cortex. A-F) Representative images of immunocytochemistry on cerebellar sections using the J2 antibody that recognizes dsRNA. DsRNA positive staining in brown (DAB) can be regularly seen in the neurons of the dentate nuclei in ALS-C9orf72 (A), but is not detected at high levels in controls (B). C) Isotype control showing specificity of the J2 antibody. D) Low power image (5×) of the cerebellum showing the restriction of J2 staining to the dentate nuclei-inset shows 40× magnification of neurons in (D) and shows the granularity of J2 staining within these neurons.

FIGS. 11A-C. The J2 antibody is specific to dsRNA. A,B) Representative images of sections from the superior frontal cortex (B8,9) with (A) the J2 antibody or (B) the J2 antibody pre incubated with PolyIC (a dsRNA mimetic) showing that the immunocytochemical staining with J2 is specific to dsRNA. C) A dot blot of dsDNA and polyIC probed with the J2 antibody showing the specificity of J2 for dsRNA.

FIGS. 12A-G. dsRNA induces a Type I interferon response and is sufficient to induced neurodegeneration in human neurons. A-E) Representative transmitted light images of differentiated ReNVM neurons transfected with increasing doses of PolyIC, a dsRNA mimetic, showing a dose-dependent loss of neurons after 48 hours. F) Quantification of the percentage of viable ReNVM neurons that have been transfected with PolyIC showing a dose-dependent loss in cell viability as measured using Celltiter-Glo. G) Western blots showing the elevated protein expression of type I interferon-stimulated genes in differentiated ReNVM cells 24 hour post transfection with PolyIC, using indicated antibodies.

DETAILED DESCRIPTION

Figure 2A:
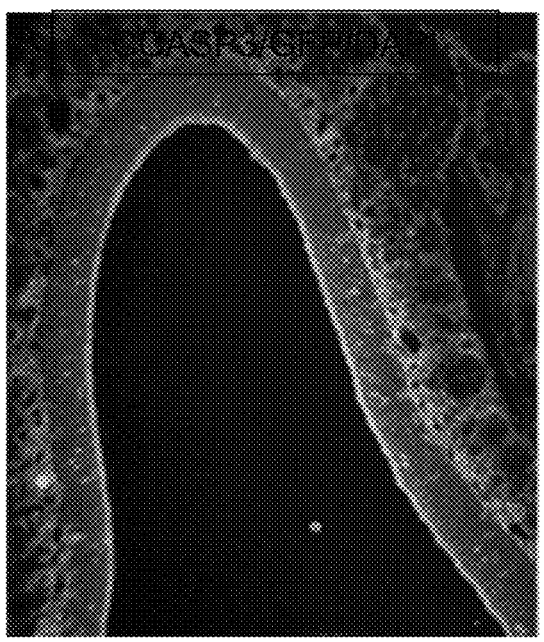
FIGS. 2A-F. Non-cell-autonomous neurodegeneration in Nd1. A) co-immunofluorescent staining with anti-GFP (green in original) and anti-CCASP3 antibodies showing that most CCASP3 positive neurons do not express the transgene at 10× magnification and at 20× magnification, shown in (B). C) Quantitation of the percent of CCASP3 positive neurons that are transgene negative (GFP-) or transgene positive (GFP+) (p=0.02, ~1000 CCASP3 positive cells for each of n=4 mice). D) RNA in situ with an anti-sense probe for GFP showing that transgene expression is restricted to a subset of olfactory sensory neurons in the olfactory epithelium and is not expressed in the olfactory bulb at low magnification and at 10× magnification (insets). E) Nd1 olfactory bulbs are qualitatively smaller than those from littermate controls. F) Quantitation of the weight of the olfactory bulbs normalized to littermate controls (p=0.001, n=4).
Figure 2B:
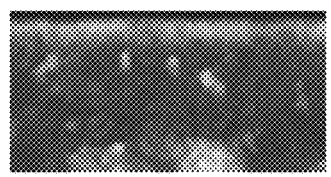

Aging is the predominant risk factor for Alzheimer's disease and is necessary for most adult-onset neurodegenerative diseases. The biology of aging is poorly understood, but one mechanism identified in aging human neurons is the robust induction of DNA repair enzymes. The present disclosure outlines a new mechanistic paradigm for neurodegeneration in mouse neurons based on expression of double stranded RNA (dsRNA) (greater than 34 nucleotides) arising from inversions of genomic sequence through routine non-homologous end joining repair or through chromothripsis, a dramatic fracturing and repair of chromosomes, that are recognized by the pattern recognition receptors MDA5 and PKR in the cytoplasm. In addition, the present disclosure identifies and validates genes and gene products that constitute two related signaling pathways triggered by dsRNA that mediate neurodegeneration and alterations in gene expression programs in neurons in vivo, and demonstrates that these signaling pathways are induced in human brains from Alzheimer's disease, frontotemporal dementia, and amyotrophic lateral sclerosis.

The present studies include a series of mouse lines that model the introduction of genomic lesions. A unique mouse line was engineered wherein the expression of the Swedish mutation of the amyloid precursor protein (hAPPsw) and the green fluorescent marker protein gene were confined to one neural circuit in vivo. In this line, hAPPsw was expressed exclusively in a sparse subset (<1%) of olfactory sensory neurons in the nose, a class of neurons with documented vulnerability Alzheimer's pathogenesis. The line was named Nd1 (Neurodegeneration 1). Examination of the Nd1 line has revealed four important insights.

First, olfactory sensory neurons turnover at an accelerated rate with an overall age-dependent reduction of mature olfactory neurons, the first mouse model to exhibit neuronal loss in response to expression on an Alzheimer's disease gene mutation isolated from patients.

Second, most neurons that are dying are not expressing the disease gene, i.e., exhibit non-cell autonomous action of APP. This is important since it provides a possible mechanism to account for the spread of the disease throughout the brain as observed by clinicians for decades and more recently by investigators using non-invasive imaging techniques.

Third, using deep sequencing, profound reductions were observed in a functionally important gene expression program of olfactory sensory neurons. Specifically, 931 olfactory receptor genes, save 2, are markedly diminished in all mature olfactory sensory neurons. Expression of these genes is dependent on epigenetic histone posttranslational modifications and on a dynamic nuclear architecture to physically approximate regions from different chromosomes to select and transcribe the chosen olfactory receptor gene.

Fourth, components of a dormant interferon signaling pathway were prominently expressed in most olfactory sensory neurons in the nose as well as many second-order olfactory neurons and adjacent interneurons in the brain. The genes that were upregulated included mouse interferon alpha 4 (human interferon alpha 16 is the closest homologue), TLR3, Eif2ak2 (PKR), Stat1, Oasl2, Ifih1, Ifi44, RNaseL, and MDA5. This result was significant because it provided the first experimental evidence of transmission of alterations of gene expression patterns to both proximate neighboring neurons and to neurons in serial connection along the olfactory neural circuit in the brain.

These four findings were observed in a related mouse line that was created that expresses a synthetic mutation of human APP that robustly reduces the production of the Aβ peptide exclusively in mouse olfactory sensory neurons (Nd2) and a third mouse line that specifically overexpresses human wild type APP (CORMAWG E). This result indicates that the mechanisms revealed by the present disclosure are likely to be relevant for sporadic Alzheimer's disease, which comprises over 95% of disease burden, as well as other neurodegenerative diseases, including C9orf72-associated frontotemporal dementia and amyotrophic lateral sclerosis. Moreover, this mechanism would be position independent (non-Mendelian) and not discoverable by GWAS studies since the lesion in each individual is likely to be unique.

The dsRNA/Type 1 Interferon Signaling/PRR Pathways

As described herein, the present inventors have found that Type 1 interferon signaling genes are upregulated in mouse models of neurodegeneration. Type I IFNs regulate gene expression for proteins with antiviral properties. The Type I IFN receptor has a multichain structure that includes at least two distinct receptor subunits, IFNαR1 and IFNαR2. As shown in FIG. 5B, two Jak-kinases, Jak-1 and Tyk-2, bind to the different receptor subunits and are activated in response to IFNα or IFNβ ligand binding to initiate multiple downstream signaling cascades. Although there are a large number of downstream pathways that may be activated by type 1 IFN signaling in various different cell types, the Stat1 pathway (which regulates transcriptional activation of IFN-sensitive genes) and the p38 Map kinase pathway (which regulates downstream activation of other serine kinases, notably MapKapK-2 and MapKapK-3, and plays a critical role in Type I IFN-dependent transcriptional regulation independent of the Stat1 pathway), appears to play a very important role in the dsRNA-induced neurodegeneration. p38 is essential for gene transcription via ISRE or GAS elements. See Platanias et al., Pharmacol Ther. 98(2):129-42 (2003).

Table A provides the sequences for human mRNA and protein for each of these targets. Other species can be identified using methods known in the art, e.g., by entering the number below into the online HomoloGene database.

TABLE A

Targets in the Type 1 IFN signaling pathway

| Target Gene | GeneBank Acc. No mRNA | GenBank Acc No. protein |
| --- | --- | --- |
| human interferon alpha 16 (IFNA16) | NM_002173.2 | NP_002164.1 |
| toll-like receptor 3 (TLR3) | NM_003265.2 | NP_003256.1 |
| eukaryotic translation initiation factor 2-alpha kinase 2 (EIF2AK2, aka PKR) | NM_001135651.2 variant 2<br>NM_001135652.2 variant 3<br>NM_002759.3 variant 1 | NP_001129123.1 isoform a<br>NP_001129124.1 isoform b<br>NP_002750.1 isoform a |
| interferon induced with helicase C domain 1 (IFIH1, aka MDA5) | NM_022168.3 | NP_071451.2 |
| mitochondrial antiviral signaling protein (MAVS) | NM_020746.4 variant 1<br>NM_001206491.1 variant 2 | NP_065797.2 Isoform 1<br>NP_001193420.1 isoform 2 |
| signal transducer and activator of transcription 1, 91 kDa (STAT1) | NM_007315.3 variant alpha<br>NM_139266.2 variant beta | NP_009330.1 isoform alpha<br>NP_644671.1 Isoform beta |
| 2'-5'-oligoadenylate synthetase-like (OASL) | NM_003733.3 variant 1<br>NM_198213.2 variant 2<br>NM_001261825.1 variant 3 | NP_003724.1 isoform a<br>NP_937856.1 isoform b<br>NP_001248754.1 isoform c |
| interferon-induced protein 44 (Ifi44) | NM_006417.4 | NP_006408.3 |
| DEAD (Asp-Glu-Ala-Asp) box polypeptide 58 (DDX58) | NM_014314.3 | NP_055129.2 |
| ribonuclease L (2',5'-oligoisoadenylate synthetase-dependent) (RNaseL) | NM_021133.3 | NP_066956.1 |

TABLE A-continued

Targets in the Type 1 IFN signaling pathway

| Target Gene | GeneBank Acc. No mRNA | GenBank Acc No. protein |
| --- | --- | --- |
| mitogen-activated protein kinase 14 (MAPK14, aka p38) | NM_011951.3 variant 1<br>NM_001168508.1 variant 2<br>NM_001168513.1 variant 3<br>NM_001168514.1 variant 4 | NP_036081.1 isoform 1<br>NP_001161980.1 isoform 2<br>NP_001161985.1 isoform 3<br>NP_001161986.1 isoform 3 |
| mitogen-activated protein kinase-activated protein kinase 2 (MapKapK-2) | NM_004759.4 variant 1<br>NM 032960.3 variant 2 | NP_004750.1 isoform 1<br>NP_116584.2 isoform 2 |
| mitogen-activated protein kinase-activated protein kinase 3 (MapKapK-3) | NM_001243926.1 variant 1<br>NM_001243925.1 variant 2<br>NM_004635.4 variant 3<br>(all encode same protein) | NP_001230855.1<br>NP_001230854.1<br>NP_004626.1 |

Compounds that target genes or proteins in the type 1 interferon dsRNA STAT response pathway, i.e., human interferon alpha 16, TLR3, Eif2ak2 (PKR), MDA5, MAVS, Stat1, Oasl2, Ifih1, Ifi44, DDX58, and RNaseL; or in the p38 pathway, i.e., p38, MapKapK-2 and MapKapK-3, can include, e.g., small molecules, inhibitory nucleic acids, and inhibitory antibodies.

Small Molecules

Small molecules that inhibit a target listed in Table A can be used disrupt Type 1 interferon signaling and cause reduction in neuronal cell death in response to dsRNA, and therefore be used to treat neurodegenerative diseases as described herein.

Figure 14:
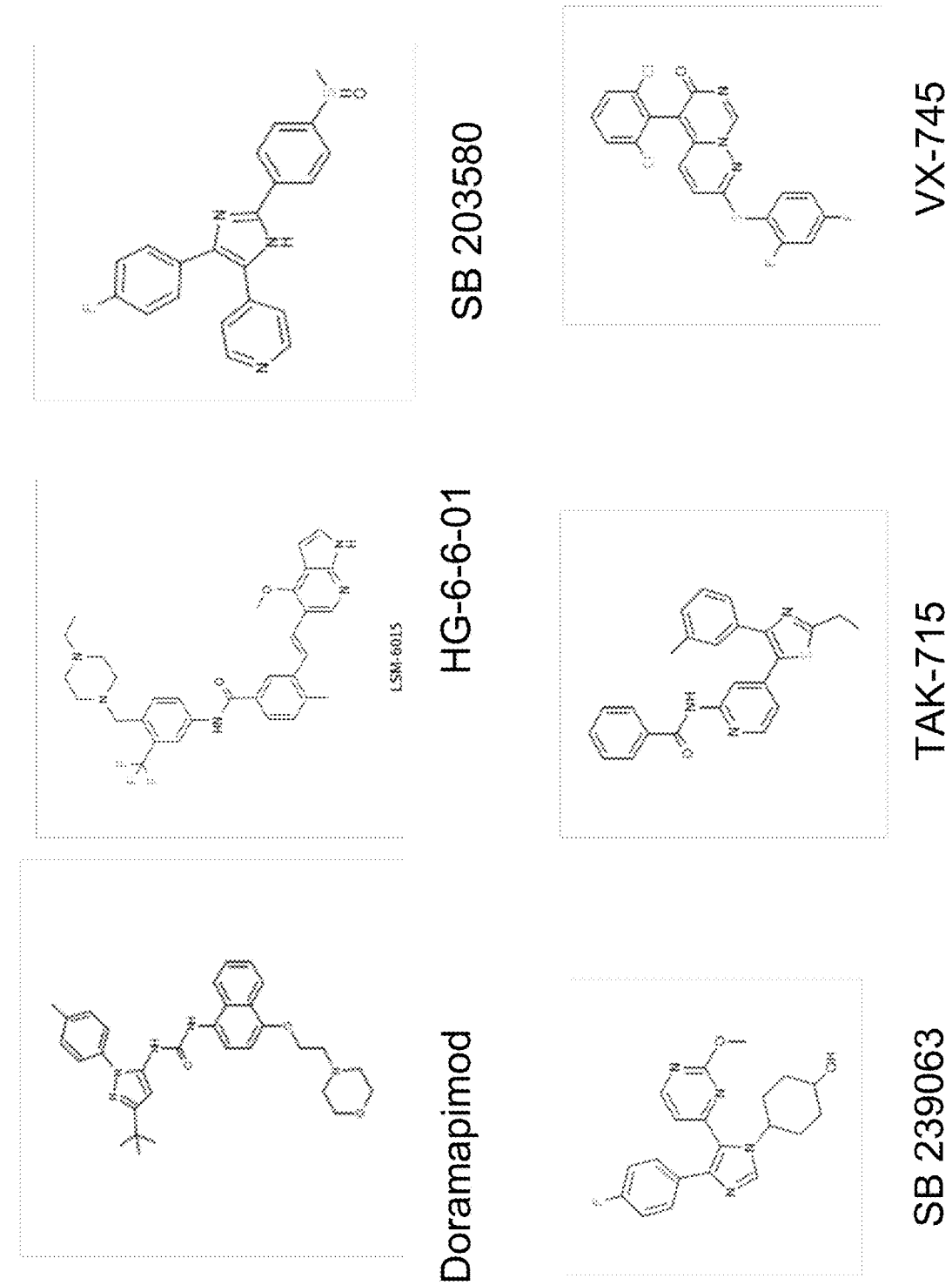
FIG. 14. MapK14 (p38) inhibitor compounds and their structures. Doramapimod, SB-203580, SB203580, SB23906, TAK-715, and VX-745.

A number of small molecule inhibitors of the targets in table A (e.g., inhibitors of the proteins) are known in the art. These include p38 inhibitors such as Doramapimod (1-[5-tert-butyl-2-(4-methylphenyl)pyrazol-3-yl]-3-[4-(2-morpholin-4-ylethoxy)naphthalen-1-yl]urea, see FIG. 14); HG-6-64-01 (LSM-6015, AGN-PC-09Q69N, N-[4-[(4-ethylpiperazin-1-yl)methyl]-3-(trifluoromethyl)phenyl]-3-[2-(4-methoxy-1H-pyrrolo[2,3-b]pyridin-5-yl)ethenyl]-4-methylbenzamide, see FIG. 14); SB 203580 (4-(4-Fluorophenyl)-2-(4-methylsulfinylphenyl)-5-(4-pyridyl) 1H-imidazole; see FIG. 14); SB 239063 (4-[4-(4-fluorophenyl)-5-(2-methoxypyrimidin-4-yl)-1H-imidazol-1-yl]cyclohexanol, see FIG. 14); TAK-715 (N-[4-[2-ethyl-4-(3-methylphenyl)-1,3-thiazol-5-yl]pyridin-2-yl] benzamide, see FIG. 14); VX-745 (5-(2,6-dichlorophenyl)-2-(2,4-difluorophenyl)sulfanylpyrimido[1,6-b]pyridazin-6-one, see FIG. 14); VX-702; Skepinone-L; SB202190 (FHPI); PH-797804; PD 169316; and LY2228820. Small molecule inhibitors of TLR3 include Imiquimod and resiquimod. Small molecule inhibitors of Stat1 include Fludarabine, NSC 74589, SD 1008, Stattic, and WP1066. Inhibitors of MapKapK-2 include NQD1, HI TOPK 032; PF 3644022; (10r)-10-methyl-3-(6-methylpyridin-3-yl)-9,10,11,12-tetrahydro-8h-[1,4]diazepino[5',6':4,5]thieno[3,2-f]quinolin-8-one; (3r)-3-(aminomethyl)-9-methoxy-1,2,3,4-tetrahydro-5h-[1]benzothieno[3,2-e][1,4]diazepin-5-one; (4r)-n-[4-({[2-(dimethylamino)ethyl]amino}carbonyl)-1,3-thiazol-2-yl]-4-methyl-1-oxo-2,3,4,9-tetrahydro-1 h-beta-carboline-6-carboxamide; 2-(2-quinolin-3-ylpyridin-4-yl)-1,5,6,7-tetrahydro-4h-pyrrolo[3,2-c]pyridin-4-one; 2-[2-(2-fluorophenyl)pyridin-4-yl]-1,5,6,7-tetrahydro-4h-pyrrolo[3,2-c]pyridin-4-one; and 3-{[(1r)-1-phenylethyl]amino}-4-(pyridin-4-ylamino)cyclobut-3-ene-1,2-dione. Inhibitors of MapKapK-3 include DB08358 (2-(2-quinolin-3-ylpyrrolo-4-yl)-1,5,6,7-tetrahydro-4h-pyrrolo[3,2-c]pyridin-4-one) and DB07728 (2-[2-(2-fluorophenyl)pyridin-4-yl]-1,5,6,7-tetrahydro-4h-pyrrolo[3,2-c]pyridin-4-one). These small molecules can be synthesized using methods known in the art or obtained from commercial sources, e.g., Tocris or other source, e.g., as listed in the DrugBank database.

Inhibiting Type 1 Interferon Signaling with Sequence-Specific Oligonucleotides

As described herein, oligonucleotides ("oligos") that hybridize specifically to a gene or transcript listed in Table A can be used disrupt Type 1 interferon signaling and cause reduction in neuronal cell death in response to dsRNA. Exemplary target sequences are listed in Table A.

In some embodiments, the oligos hybridize to at least 7, 8, 9, 10, 11, 12, 13, 14, 15, 16, 17, 18, 19, 20, 21, 22, 23, 24, 25, 26, 27, 28, 29, 30 or more consecutive nucleotides of the target sequence.

In some embodiments, the methods include introducing into the cell an oligo that specifically binds, or is complementary, to a gene listed in Table A. A nucleic acid that "specifically" binds primarily to the target, i.e., to a gene listed in Table A RNA but not to other non-target RNAs. The specificity of the nucleic acid interaction thus refers to its function (e.g., inhibiting a gene listed in Table A) rather than its hybridization capacity. Oligos may exhibit nonspecific binding to other sites in the genome or other mRNAs, without interfering with binding of other regulatory proteins and without causing degradation of the non-specifically-bound RNA. Thus this nonspecific binding does not significantly affect function of other non-target RNAs and results in no significant adverse effects. These methods can be used to treat a subject, e.g., a subject with cancer, by administering to the subject a composition (e.g., as described herein) comprising an oligo that binds to a gene listed in Table A. Examples of oligos and target sequences are provided herein.

As used herein, treating includes "prophylactic treatment" which means reducing the incidence of or preventing (or reducing risk of) a sign or symptom of a disease in a patient at risk for the disease, and "therapeutic treatment", which means reducing signs or symptoms of a disease, reducing progression of a disease, reducing severity of a disease, in a patient diagnosed with the disease.

In some embodiments, the methods described herein include administering a composition, e.g., a sterile composition, comprising an oligo that is complementary to a gene listed in Table A sequence as described herein. Oligos for use in practicing the methods described herein can be an antisense or small interfering RNA, including but not limited to an shRNA or siRNA. In some embodiments, the oligo is a modified nucleic acid polymer (e.g., a locked nucleic acid (LNA) molecule), a gapmer, or a mixmer.

Oligos have been employed as therapeutic moieties in the treatment of disease states in animals, including humans. Oligos can be useful therapeutic modalities that can be configured to be useful in treatment regimens for the treatment of cells, tissues and animals, especially humans.

For therapeutics, an animal, preferably a human, suspected of having cancer is treated by administering an oligo in accordance with this disclosure. For example, in one non-limiting embodiment, the methods comprise the step of administering to the animal in need of treatment a therapeutically effective amount of an oligo as described herein.

Oligonucleotides

Oligos useful in the present methods and compositions include antisense oligonucleotides, ribozymes, external guide sequence (EGS) oligonucleotides, siRNA compounds, single- or double-stranded RNA interference (RNAi) compounds such as siRNA compounds, molecules comprising modified bases, locked nucleic acid molecules (LNA molecules), antagomirs, peptide nucleic acid molecules (PNA molecules), mixmers, gapmers, and other oligomeric compounds or oligonucleotide mimetics that hybridize to at least a portion of a gene listed in Table A and modulate its function. In some embodiments, the oligos include antisense RNA, antisense DNA, chimeric antisense oligonucleotides, antisense oligonucleotides comprising modified linkages, interference RNA (RNAi), short interfering RNA (siRNA); a micro, interfering RNA (miRNA); a small, temporal RNA (stRNA); or a short, hairpin RNA (shRNA); small RNA-induced gene activation (RNAa); small activating RNAs (saRNAs), or combinations thereof. See, e.g., WO2010/040112. However, in some embodiments the oligo is not an miRNA, an stRNA, an shRNA, an siRNA, an RNAi, or a dsRNA.

In some embodiments, the oligos are 10 to 50, 13 to 50, or 13 to 30 nucleotides in length. One having ordinary skill in the art will appreciate that this embodies oligonucleotides having antisense (complementary) portions of 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 nucleotides in length, or any range therewithin. It is understood that non-complementary bases may be included in such oligos; for example, an oligo 30 nucleotides in length may have a portion of 15 bases that is complementary to the targeted gene listed in Table A RNA. In some embodiments, the oligonucleotides are 15 nucleotides in length. In some embodiments, the antisense or oligonucleotide compounds of the invention are 12 or 13 to 30 nucleotides in length. One having ordinary skill in the art will appreciate that this embodies oligos having antisense (complementary) portions of 12, 13, 14, 15, 16, 17, 18, 19, 20, 21, 22, 23, 24, 25, 26, 27, 28, 29 or 30 nucleotides in length, or any range therewithin.

Preferably the oligo comprises one or more modifications comprising: a modified sugar moiety, and/or a modified internucleoside linkage, and/or a modified nucleotide and/or combinations thereof. It is not necessary for all positions in a given oligonucleotide to be uniformly modified, and in fact more than one of the modifications described herein may be incorporated in a single oligonucleotide or even at within a single nucleoside within an oligonucleotide.

In some embodiments, the oligos are chimeric oligonucleotides that contain two or more chemically distinct regions, each made up of at least one nucleotide. These oligonucleotides typically contain at least one region of modified nucleotides that confers one or more beneficial properties (such as, for example, increased nuclease resistance, increased uptake into cells, increased binding affinity for the target) and a region that is a substrate for enzymes capable of cleaving RNA:DNA or RNA:RNA hybrids. Chimeric oligos of the invention may be formed as composite structures of two or more oligonucleotides, modified oligonucleotides, oligonucleosides and/or oligonucleotide mimetics as described above. Such compounds have also been referred to in the art as hybrids or gapmers. Representative United States patents that teach the preparation of such hybrid structures comprise, but are not limited to, U.S. Pat. Nos. 5,013,830; 5,149,797; 5,220,007; 5,256,775; 5,366,878; 5,403,711; 5,491,133; 5,565,350; 5,623,065; 5,652,355; 5,652,356; and 5,700,922, each of which is herein incorporated by reference.

In some embodiments, the oligo comprises at least one nucleotide modified at the 2' position of the sugar, most preferably a 2'-O-alkyl, 2'-O-alkyl-O-alkyl or 2'-fluoro-modified nucleotide. In other preferred embodiments, RNA modifications include 2'-fluoro, 2'-amino and 2' O-methyl modifications on the ribose of pyrimidines, abasic residues or an inverted base at the 3' end of the RNA. Such modifications are routinely incorporated into oligonucleotides and these oligonucleotides have been shown to have a higher Tm (i.e., higher target binding affinity) than; 2'-deoxyoligonucleotides against a given target.

A number of nucleotide and nucleoside modifications have been shown to make the oligonucleotide into which they are incorporated more resistant to nuclease digestion than the native oligodeoxynucleotide; these modified oligos survive intact for a longer time than unmodified oligonucleotides. Specific examples of modified oligonucleotides include those comprising modified backbones, for example, phosphorothioates, phosphotriesters, methyl phosphonates, short chain alkyl or cycloalkyl intersugar linkages or short chain heteroatomic or heterocyclic intersugar linkages. Most preferred are oligonucleotides with phosphorothioate backbones and those with heteroatom backbones, particularly $CH_2$—NH—O—$CH_2$, CH, ~$N(CH_3)$~O~$CH_2$ (known as a methylene(methylimino) or MMI backbone], $CH_2$—O—N($CH_3$)—$CH_2$, $CH_2$—N($CH_3$)—N($CH_3$)—$CH_2$ and O—N($CH_3$)— $CH_2$—$CH_2$ backbones, wherein the native phosphodiester backbone is represented as O— P—O— CH,); amide backbones (see De Mesmaeker et al. Ace. Chem. Res. 1995, 28:366-374); morpholino backbone structures (see Summerton and Weller, U.S. Pat. No. 5,034,506); peptide nucleic acid (PNA) backbone (wherein the phosphodiester backbone of the oligonucleotide is replaced with a polyamide backbone, the nucleotides being bound directly or indirectly to the aza nitrogen atoms of the polyamide backbone, see Nielsen et al., Science 1991, 254, 1497). Phosphorus-containing linkages include, but are not limited to, phosphorothioates, chiral phosphorothioates, phosphorodithioates, phosphotriesters, aminoalkylphosphotriesters, methyl and other alkyl phosphonates comprising 3'alkylene phosphonates and chiral phosphonates, phosphinates, phosphoramidates comprising 3'-amino phosphoramidate and aminoalkylphosphoramidates, thionophosphoramidates, thionoalkylphosphonates, thionoalkylphosphotriesters, and boranophosphates having normal 3'-5' linkages, 2'-5' linked analogs of these, and those having inverted polarity wherein the adjacent pairs of nucleoside units are linked 3'-5' to 5'-3' or 2'-5' to 5'-2'; see U.S. Pat. Nos. 3,687,808; 4,469,863; 4,476,301; 5,023,243; 5,177,196; 5,188,897; 5,264,423; 5,276,019; 5,278,302; 5,286,717; 5,321,131; 5,399,676; 5,405,939; 5,453,496; 5,455, 233; 5,466,677; 5,476,925; 5,519,126; 5,536,821; 5,541,306; 5,550,111; 5,563, 253; 5,571,799; 5,587,361; and 5,625,050.

Morpholino-based oligomeric compounds are described in Dwaine A. Braasch and David R. Corey, Biochemistry, 2002, 41(14), 4503-4510); Genesis, volume 30, issue 3, 2001; Heasman, J., Dev. Biol., 2002, 243, 209-214; Nasevicius et al., Nat. Genet., 2000, 26, 216-220; Lacerra et al., Proc. Natl. Acad. Sci., 2000, 97, 9591-9596; and U.S. Pat. No. 5,034,506, issued Jul. 23, 1991. In some embodiments, the morpholino-based oligomeric compound is a phosphorodiamidate morpholino oligomer (PMO) (e.g., as described in Iverson, Curr. Opin. Mol. Ther., 3:235-238, 2001; and Wang et al., J. Gene Med., 12:354-364, 2010; the disclosures of which are incorporated herein by reference in their entireties).

Cyclohexenyl nucleic acid oligonucleotide mimetics are described in Wang et al., J. Am. Chem. Soc., 2000, 122, 8595-8602.

Modified oligonucleotide backbones that do not include a phosphorus atom therein have backbones that are formed by short chain alkyl or cycloalkyl internucleoside linkages, mixed heteroatom and alkyl or cycloalkyl internucleoside linkages, or one or more short chain heteroatomic or heterocyclic internucleoside linkages. These comprise those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; alkene containing backbones; sulfamate backbones; methyleneimino and methylenehydrazino backbones; sulfonate and sulfonamide backbones; amide backbones; and others having mixed N, O, S and $CH_2$ component parts; see U.S. Pat. Nos. 5,034,506; 5,166,315; 5,185,444; 5,214,134; 5,216,141; 5,235,033; 5,264, 562; 5, 264,564; 5,405,938; 5,434,257; 5,466,677; 5,470,967; 5,489,677; 5,541,307; 5,561,225; 5,596,086; 5,602,240; 5,610,289; 5,602,240; 5,608,046; 5,610,289; 5,618,704; 5,623,070; 5,663,312; 5,633,360; 5,677,437; and 5,677,439, each of which is herein incorporated by reference.

Modified oligonucleotides are also known that include oligonucleotides that are based on or constructed from arabinonucleotide or modified arabinonucleotide residues.

Arabinonucleosides are stereoisomers of ribonucleosides, differing only in the configuration at the 2'-position of the sugar ring. In some embodiments, a 2'-arabino modification is 2'-F arabino. In some embodiments, the modified oligonucleotide is 2'-fluoro-D-arabinonucleic acid (FANA) (as described in, for example, Lon et al., Biochem., 41:3457-3467, 2002 and Min et al., Bioorg. Med. Chem. Lett., 12:2651-2654, 2002; the disclosures of which are incorporated herein by reference in their entireties). Similar modifications can also be made at other positions on the sugar, particularly the 3' position of the sugar on a 3' terminal nucleoside or in 2'-5' linked oligonucleotides and the 5' position of 5' terminal nucleotide.

PCT Publication No. WO 99/67378 discloses arabinonucleic acids (ANA) oligomers and their analogues for improved sequence specific inhibition of gene expression via association to complementary messenger RNA.

Other preferred modifications include ethylene-bridged nucleic acids (ENAs) (e.g., International Patent Publication No. WO 2005/042777, Morita et al., Nucleic Acid Res., Suppl 1:241-242, 2001; Surono et al., Hum. Gene Ther., 15:749-757, 2004; Koizumi, Curr. Opin. Mol. Ther., 8:144-149, 2006 and Horie et al., Nucleic Acids Symp. Ser (Oxf), 49:171-172, 2005; the disclosures of which are incorporated herein by reference in their entireties). Preferred ENAs include, but are not limited to, 2'-0,4'-C-ethylene-bridged nucleic acids.

Examples of LNAs are described in WO 2008/043753 and WO2007031091 and include compounds of the following formula.

Scheme 1

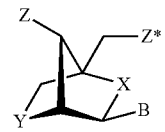

where X and Y are independently selected among the groups —O—, —S—, —N(H)—, N(R)—, —$CH_2$— or —CH— (if part of a double bond), —$CH_2$—O—, —$CH_2$—S—, —$CH_2$—N(H)—, —$CH_2$—N(R)—, —$CH_2$—$CH_2$— or —$CH_2$—CH— (if part of a double bond), —CH=CH—, where R is selected from hydrogen and C1-4-alkyl; Z and Z* are independently selected among an internucleoside linkage, a terminal group or a protecting group; B constitutes a natural or non-natural nucleotide base moiety; and the asymmetric groups may be found in either orientation.

Preferably, the LNA used in the oligomer of the invention comprises at least one LNA unit according any of the formulas Scheme 2

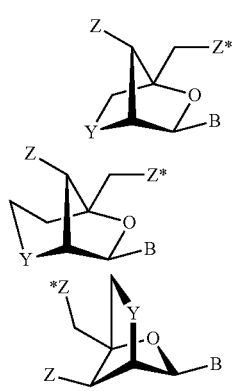

wherein Y is —O—, —S—, —NH—, or N($R^H$); Z and Z* are independently selected among an internucleoside linkage, a terminal group or a protecting group; B constitutes a natural or non-natural nucleotide base moiety, and RH is selected from hydrogen and $C_{1-4}$-alkyl. Preferably, the Locked Nucleic Acid (LNA) used in an oligomeric compound, such as an antisense oligonucleotide, as described herein comprises at least one nucleotide comprises a Locked Nucleic Acid (LNA) unit according any of the formulas shown in Scheme 2 of PCT/DK2006/000512 (WO2007031091).

Preferably, the LNA used in the oligomer of the invention comprises internucleoside linkages selected from —O—P(O)$_2$—O—, —O—P(O,S)—O—, —O—P(S)$_2$—O—, —S—P(O)$_2$—O—, —S—P(O,S)—O—, —S—P(S)$_2$—O—, —O—P(O)$_2$—S—, —O—P(O,S)—S—, —S—P(O)$_2$—S—, —O—PO($R^H$)—O—, O—PO (O$CH_3$)—O—, —O—PO(N$R^H$)—O—, —O—PO (O$CH_2CH_2$S—R)—O—, —O—PO(B$H_3$)—O—, —O—PO (NH$R^H$)—O—, —O—P(O)$_2$—N$R^H$—, —N$R^H$—P(O)$_2$—O—, —N$R^H$—CO—O—, where $R^H$ is selected from hydrogen and $C_{1-4}$-alkyl.

Specifically preferred LNA units are shown in scheme 3:

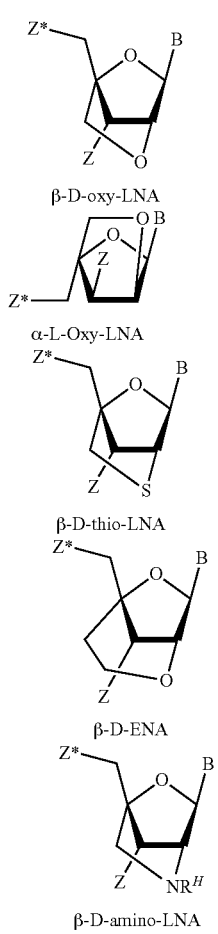

Scheme 3

β-D-oxy-LNA

α-L-Oxy-LNA

β-D-thio-LNA

β-D-ENA

β-D-amino-LNA

The term "thio-LNA" comprises a locked nucleotide in which at least one of X or Y in the general formula above is selected from S or —CH$_2$—S—. Thio-LNA can be in both beta-D and alpha-L-configuration.

The term "amino-LNA" comprises a locked nucleotide in which at least one of X or Y in the general formula above is selected from —N(H)—, N(R)—, CH$_2$—N(H)—, and —CH$_2$—N(R)— where R is selected from hydrogen and C$_{1-4}$-alkyl. Amino-LNA can be in both beta-D and alpha-L-configuration.

The term "oxy-LNA" comprises a locked nucleotide in which at least one of X or Y in the general formula above represents —O— or —CH$_2$—O—. Oxy-LNA can be in both beta-D and alpha-L-configuration.

The term "ena-LNA" comprises a locked nucleotide in which Y in the general formula above is —CH$_2$—O— (where the oxygen atom of —CH$_2$—O— is attached to the 2'-position relative to the base B).

LNAs are described in additional detail below. One or more substituted sugar moieties can also be included, e.g., one of the following at the 2' position: OH, SH, SCH$_3$, F, OCN, OCH$_3$OCH$_3$, OCH$_3$O(CH$_2$)n CH$_3$, O(CH$_2$)nNH$_2$ or O(CH$_2$)n CH$_3$ where n is from 1 to about 10; Ci to C10 lower alkyl, alkoxyalkoxy, substituted lower alkyl, alkaryl or aralkyl; Cl; Br; CN; CF3; OCF3; O-, S-, or N-alkyl; O-, S-, or N-alkenyl; SOCH3; SO2CH3; ONO2; NO2; N3; NH2; heterocycloalkyl; heterocycloalkaryl; aminoalkylamino; polyalkylamino; substituted silyl; an RNA cleaving group; a reporter group; an intercalator; a group for improving the pharmacokinetic properties of an oligonucleotide; or a group for improving the pharmacodynamic properties of an oligonucleotide and other substituents having similar properties. A preferred modification includes 2'-methoxyethoxy [2'-O—CH$_2$CH$_2$OCH$_3$, also known as 2'-O-(2-methoxyethyl)] (Martin et al, Helv. Chim. Acta, 1995, 78, 486). Other preferred modifications include 2'-methoxy (2'-0-CH$_3$), 2'-propoxy (2'-OCH$_2$CH$_2$CH$_3$) and 2'-fluoro (2'-F). Similar modifications may also be made at other positions on the oligonucleotide, particularly the 3' position of the sugar on the 3' terminal nucleotide and the 5' position of 5' terminal nucleotide. Oligonucleotides may also have sugar mimetics such as cyclobutyls in place of the pentofuranosyl group.

Oligos can also include, additionally or alternatively, nucleobase (often referred to in the art simply as "base") modifications or substitutions. As used herein, "unmodified" or "natural" nucleobases include adenine (A), guanine (G), thymine (T), cytosine (C) and uracil (U). Modified nucleobases include nucleobases found only infrequently or transiently in natural nucleic acids, e.g., hypoxanthine, 6-methyladenine, 5-Me pyrimidines, particularly 5-methylcytosine (also referred to as 5-methyl-2' deoxycytosine and often referred to in the art as 5-Me-C), 5-hydroxymethylcytosine (HMC), glycosyl HMC and gentobiosyl HMC, isocytosine, pseudoisocytosine, as well as synthetic nucleobases, e.g., 2-aminoadenine, 2-(methylamino)adenine, 2-(imidazolylalkyl)adenine, 2-(aminoalklyamino)adenine or other heterosubstituted alkyladenines, 2-thiouracil, 2-thiothymine, 5-bromouracil, 5-hydroxymethyluracil, 5-propynyluracil, 8-azaguanine, 7-deazaguanine, N6 (6-aminohexyl)adenine, 6-aminopurine, 2-aminopurine, 2-chloro-6-aminopurine and 2,6-diaminopurine or other diaminopurines. See, e.g., Kornberg, "DNA Replication," W. H. Freeman & Co., San Francisco, 1980, pp 75-77; and Gebeyehu, G., et al. Nucl. Acids Res., 15:4513 (1987)). A "universal" base known in the art, e.g., inosine, can also be included. 5-Me-C substitutions have been shown to increase nucleic acid duplex stability by 0.6-1.2<0>C. (Sanghvi, in Crooke, and Lebleu, eds., Antisense Research and Applications, CRC Press, Boca Raton, 1993, pp. 276-278) and are presently preferred base substitutions.

It is not necessary for all positions in a given oligonucleotide to be uniformly modified, and in fact more than one of the modifications described herein may be incorporated in a single oligonucleotide or even at within a single nucleoside within an oligonucleotide.

In some embodiments, both a sugar and an internucleoside linkage, i.e., the backbone, of the nucleotide units are replaced with novel groups. The base units are maintained for hybridization with an appropriate nucleic acid target compound. One such oligomeric compound, an oligonucleotide mimetic that has been shown to have excellent hybridization properties, is referred to as a peptide nucleic acid (PNA). In PNA compounds, the sugar-backbone of an oligonucleotide is replaced with an amide containing backbone, for example, an aminoethylglycine backbone. The nucleobases are retained and are bound directly or indirectly to aza nitrogen atoms of the amide portion of the backbone. Representative United States patents that teach the preparation of PNA compounds include, but are not limited to, U.S. Pat. Nos. 5,539,082; 5,714,331; and 5,719,262, each of which is herein incorporated by reference. Further teaching of PNA compounds can be found in Nielsen et al, Science, 1991, 254, 1497-1500.

Oligos can also include one or more nucleobase (often referred to in the art simply as "base") modifications or substitutions. As used herein, "unmodified" or "natural" nucleobases comprise the purine bases adenine (A) and guanine (G), and the pyrimidine bases thymine (T), cytosine (C) and uracil (U). Modified nucleobases comprise other synthetic and natural nucleobases such as 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl uracil and cytosine, 6-azo uracil, cytosine and thymine, 5-uracil (pseudo-uracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylquanine and 7-methyladenine, 8-azaguanine and 8-azaadenine, 7-deazaguanine and 7-deazaadenine and 3-deazaguanine and 3-deazaadenine.

Further, nucleobases comprise those disclosed in U.S. Pat. No. 3,687,808, those disclosed in "The Concise Encyclopedia of Polymer Science And Engineering", pages 858-859, Kroschwitz, ed. John Wiley & Sons, 1990; those disclosed by Englisch et al., Angewandle Chemie, International Edition, 1991, 30, page 613, and those disclosed by Sanghvi, Chapter 15, Antisense Research and Applications," pages 289-302, Crooke, and Lebleu, eds., CRC Press, 1993. Certain of these nucleobases are particularly useful for increasing the binding affinity of the oligomeric compounds of the invention. These include 5-substituted pyrimidines, 6-azapyrimidines and N-2, N-6 and 0-6 substituted purines, comprising 2-aminopropyladenine, 5-propynyluracil and 5-propynylcytosine. 5-methylcytosine substitutions have been shown to increase nucleic acid duplex stability by 0.6-1.2° C. (Sanghvi, et al., eds, "Antisense Research and Applications," CRC Press, Boca Raton, 1993, pp. 276-278) and are presently preferred base substitutions, even more particularly when combined with 2'-O-methoxyethyl sugar modifications. Modified nucleobases are described in U.S. Pat. No. 3,687,808, as well as U.S. Pat. Nos. 4,845,205; 5,130,302; 5,134,066; 5,175,273; 5,367,066; 5,432,272; 5,457,187; 5,459,255; 5,484,908; 5,502,177; 5,525,711; 5,552,540; 5,587,469; 5,596,091; 5,614,617; 5,750,692, and 5,681,941, each of which is herein incorporated by reference.

In some embodiments, the oligos are chemically linked to one or more moieties or conjugates that enhance the activity, cellular distribution, or cellular uptake of the oligonucleotide. For example, one or more oligos, of the same or different types, can be conjugated to each other; or oligos can be conjugated to targeting moieties with enhanced specificity for a cell type or tissue type. Such moieties include, but are not limited to, lipid moieties such as a cholesterol moiety (Letsinger et al., Proc. Natl. Acad. Sci. USA, 1989, 86, 6553-6556), cholic acid (Manoharan et al., Bioorg. Med. Chem. Let., 1994, 4, 1053-1060), a thioether, e.g., hexyl-S-tritylthiol (Manoharan et al, Ann. N. Y. Acad. Sci., 1992, 660, 306-309; Manoharan et al., Bioorg. Med. Chem. Let., 1993, 3, 2765-2770), a thiocholesterol (Oberhauser et al., Nucl. Acids Res., 1992, 20, 533-538), an aliphatic chain, e.g., dodecandiol or undecyl residues (Kabanov et al., FEBS Lett., 1990, 259, 327-330; Svinarchuk et al., Biochimie, 1993, 75, 49-54), a phospholipid, e.g., di-hexadecyl-rac-glycerol or triethylammonium 1,2-di-O-hexadecyl-rac-glycero-3-H-phosphonate (Manoharan et al., Tetrahedron Lett., 1995, 36, 3651-3654; Shea et al., Nucl. Acids Res., 1990, 18, 3777-3783), a polyamine or a polyethylene glycol chain (Mancharan et al., Nucleosides & Nucleotides, 1995, 14, 969-973), or adamantane acetic acid (Manoharan et al., Tetrahedron Lett., 1995, 36, 3651-3654), a palmityl moiety (Mishra et al., Biochim. Biophys. Acta, 1995, 1264, 229-237), or an octadecylamine or hexylaminocarbonyl-t oxycholesterol moiety (Crooke et al., J. Pharmacol. Exp. Ther., 1996, 277, 923-937). See also U.S. Pat. Nos. 4,828,979; 4,948,882; 5,218,105; 5,525,465; 5,541,313; 5,545,730; 5,552, 538; 5,578,717; 5,580,731; 5,580,731; 5,591,584; 5,109,124; 5,118,802; 5,138,045; 5,414,077; 5,486, 603; 5,512,439; 5,578,718; 5,608,046; 4,587,044; 4,605,735; 4,667,025; 4,762, 779; 4,789,737; 4,824,941; 4,835,263; 4,876,335; 4,904,582; 4,958,013; 5,082, 830; 5,112,963; 5,214,136; 5,082,830; 5,112,963; 5,214,136; 5, 245,022; 5,254,469; 5,258,506; 5,262,536; 5,272,250; 5,292,873; 5,317,098; 5,371,241, 5,391, 723; 5,416,203, 5,451,463; 5,510,475; 5,512,667; 5,514,785; 5, 565,552; 5,567,810; 5,574,142; 5,585,481; 5,587,371; 5,595,726; 5,597,696; 5,599,923; 5,599, 928 and 5,688,941, each of which is herein incorporated by reference.

These moieties or conjugates can include conjugate groups covalently bound to functional groups such as primary or secondary hydroxyl groups. Conjugate groups of the invention include intercalators, reporter molecules, polyamines, polyamides, polyethylene glycols, polyethers, groups that enhance the pharmacodynamic properties of oligomers, and groups that enhance the pharmacokinetic properties of oligomers. Typical conjugate groups include cholesterols, lipids, phospholipids, biotin, phenazine, folate, phenanthridine, anthraquinone, acridine, fluoresceins, rhodamines, coumarins, and dyes. Groups that enhance the pharmacodynamic properties, in the context of this invention, include groups that improve uptake, enhance resistance to degradation, and/or strengthen sequence-specific hybridization with the target nucleic acid. Groups that enhance the pharmacokinetic properties, in the context of this invention, include groups that improve uptake, distribution, metabolism or excretion of the compounds of the present invention. Representative conjugate groups are disclosed in International Patent Application No. PCT/US92/09196, filed Oct. 23, 1992, and U.S. Pat. No. 6,287,860, which are incorporated herein by reference. Conjugate moieties include, but are not limited to, lipid moieties such as a cholesterol moiety, cholic acid, a thioether, e.g., hexyl-5-tritylthiol, a thiocholesterol, an aliphatic chain, e.g., dodecandiol or undecyl residues, a phospholipid, e.g., di-hexadecyl-rac-glycerol or triethylammonium 1,2-di-O-hexadecyl-rac-glycero-3-H-phosphonate, a polyamine or a polyethylene glycol chain, or adamantane acetic acid, a palmityl moiety, or an octadecylamine or hexylamino-carbonyl-oxy cholesterol moiety. See, e.g., U.S. Pat. Nos. 4,828,979; 4,948,882; 5,218,105; 5,525,465; 5,541,313; 5,545,730; 5,552,538; 5,578,717; 5,580,731; 5,580,731; 5,591,584; 5,109,124; 5,118,802; 5,138,045; 5,414,077; 5,486,603; 5,512,439; 5,578,718; 5,608,046; 4,587,044; 4,605,735; 4,667,025; 4,762,779; 4,789,737; 4,824,941; 4,835,263; 4,876,335; 4,904,582; 4,958,013; 5,082,830; 5,112,963; 5,214,136; 5,082,830; 5,112,963; 5,214,136; 5,245,022; 5,254,469; 5,258,506; 5,262,536; 5,272,250; 5,292,873; 5,317,098; 5,371,241; 5,391,723; 5,416,203, 5,451,463; 5,510,475; 5,512,667; 5,514,785; 5,565,552; 5,567,810; 5,574,142; 5,585,481; 5,587,371; 5,595,726; 5,597,696; 5,599,923; 5,599,928 and 5,688,941.

The oligos useful in the present methods are sufficiently complementary to the target a gene listed in Table A, e.g., hybridize sufficiently well and with sufficient biological functional specificity, to give the desired effect. "Complementary" refers to the capacity for pairing, through base stacking and specific hydrogen bonding, between two sequences comprising naturally or non-naturally occurring (e.g., modified as described above) bases (nucleosides) or analogs thereof. For example, if a base at one position of an oligo is capable of hydrogen bonding with a base at the corresponding position of a gene listed in Table A, then the bases are considered to be complementary to each other at that position. 100% complementarity is not required. As noted above, oligos can comprise universal bases, or inert abasic spacers that provide no positive or negative contribution to hydrogen bonding. Base pairings may include both canonical Watson-Crick base pairing and non-Watson-Crick base pairing (e.g., Wobble base pairing and Hoogsteen base pairing). It is understood that for complementary base pairings, adenosine-type bases (A) are complementary to thymidine-type bases (T) or uracil-type bases (U), that cytosine-type bases (C) are complementary to guanosine-type bases (G), and that universal bases such as such as 3-nitropyrrole or 5-nitroindole can hybridize to and are considered complementary to any A, C, U, or T. Nichols et al., Nature, 1994; 369:492-493 and Loakes et al., Nucleic Acids Res., 1994; 22:4039-4043. Inosine (I) has also been considered in the art to be a universal base and is considered complementary to any A, C, U, or T. See Watkins and SantaLucia, Nucl. Acids Research, 2005; 33 (19): 6258-6267.

In some embodiments, the location on a target a gene listed in Table A binding site to which an oligo hybridizes is a region to which a protein binding partner binds. The identification of these binding sites is described in the Examples below. Routine methods can be used to design an oligo that binds to a selected strong or moderate binding site sequence with sufficient specificity. In some embodiments, the methods include using bioinformatics methods known in the art to identify regions of secondary structure, e.g., one, two, or more stem-loop structures, or pseudoknots, and selecting those regions to target with an oligo. For example, methods of designing oligonucleotides similar to the oligos described herein, and various options for modified chemistries or formats, are exemplified in Lennox and Behlke, Gene Therapy (2011) 18: 1111-1120, which is incorporated herein by reference in its entirety, with the understanding that the inhibitory oligonucleotides of the present disclosure do not target miRNA 'seed regions'.

While the specific sequences of certain exemplary target segments are set forth herein, one of skill in the art will recognize that these serve to illustrate and describe particular embodiments within the scope of the present invention. Additional target segments are readily identifiable by one having ordinary skill in the art in view of this disclosure. One having skill in the art armed with the sequences provided herein will be able, without undue experimentation, to identify further preferred regions to target with complementary oligos.

In the context of the present disclosure, hybridization means base stacking and hydrogen bonding, which may be Watson-Crick, Hoogsteen or reversed Hoogsteen hydrogen bonding, between complementary nucleoside or nucleotide bases. For example, adenine and thymine are complementary nucleobases which pair through the formation of hydrogen bonds. Complementary, as the term is used in the art, refers to the capacity for precise pairing between two nucleotides. For example, if a nucleotide at a certain position of an oligonucleotide is capable of hydrogen bonding with a nucleotide at the same position of a gene listed in Table A molecule, then the oligo and the a gene listed in Table A molecule are considered to be complementary to each other at that position. The oligos and the a gene listed in Table A molecule are complementary to each other when a sufficient number of corresponding positions in each molecule are occupied by nucleotides that can hydrogen bond with each other through their bases. Thus, "specifically hybridizable" and "complementary" are terms which are used to indicate a sufficient degree of complementarity or precise pairing such that stable and specific binding occurs between the oligo and the a gene listed in Table A molecule. For example, if a base at one position of an oligo is capable of hydrogen bonding with a base at the corresponding position of a gene listed in Table A, then the bases are considered to be complementary to each other at that position. 100% complementarity is not required.

It is understood in the art that a complementary nucleic acid sequence need not be 100% complementary to that of its target nucleic acid to be specifically hybridizable. A complementary nucleic acid sequence for purposes of the present methods is specifically hybridizable when binding of the sequence to the target a gene listed in Table A molecule interferes with the normal function of a gene listed in Table A to cause a loss of activity and there is a sufficient degree of complementarity to avoid non-specific binding of the sequence to non-target sequences under conditions in which avoidance of the non-specific binding is desired, e.g., under physiological conditions in the case of in vivo assays or therapeutic treatment, and in the case of in vitro assays, under conditions in which the assays are performed under suitable conditions of stringency. For example, stringent salt concentration will ordinarily be less than about 750 mM NaCl and 75 mM trisodium citrate, preferably less than about 500 mM NaCl and 50 mM trisodium citrate, and more preferably less than about 250 mM NaCl and 25 mM trisodium citrate. Low stringency hybridization can be obtained in the absence of organic solvent, e.g., formamide, while high stringency hybridization can be obtained in the presence of at least about 35% formamide, and more preferably at least about 50% formamide. Stringent temperature conditions will ordinarily include temperatures of at least about 30° C., more preferably of at least about 37° C., and most preferably of at least about 42° C. Varying additional parameters, such as hybridization time, the concentration of detergent, e.g., sodium dodecyl sulfate (SDS), and the inclusion or exclusion of carrier DNA, are well known to those skilled in the art. Various levels of stringency are accomplished by combining these various conditions as needed. In a preferred embodiment, hybridization will occur at 30° C. in 750 mM NaCl, 75 mM trisodium citrate, and 1% SDS. In a more preferred embodiment, hybridization will occur at 37° C. in 500 mM NaCl, 50 mM trisodium citrate, 1% SDS, 35% formamide, and 100 µg/ml denatured salmon sperm DNA (ssDNA). In a most preferred embodiment, hybridization will occur at 42° C. in 250 mM NaCl, 25 mM trisodium citrate, 1% SDS, 50% formamide, and 200 µg/ml ssDNA. Useful variations on these conditions will be readily apparent to those skilled in the art.

For most applications, washing steps that follow hybridization will also vary in stringency. Wash stringency conditions can be defined by salt concentration and by temperature. As above, wash stringency can be increased by decreasing salt concentration or by increasing temperature. For example, stringent salt concentration for the wash steps will preferably be less than about 30 mM NaCl and 3 mM trisodium citrate, and most preferably less than about 15 mM NaCl and 1.5 mM trisodium citrate. Stringent temperature conditions for the wash steps will ordinarily include a temperature of at least about 25° C., more preferably of at least about 42° C., and even more preferably of at least about 68° C. In a preferred embodiment, wash steps will occur at 25° C. in 30 mM NaCl, 3 mM trisodium citrate, and 0.1% SDS. In a more preferred embodiment, wash steps will occur at 42° C. in 15 mM NaCl, 1.5 mM trisodium citrate, and 0.1% SDS. In a more preferred embodiment, wash steps will occur at 68° C. in 15 mM NaCl, 1.5 mM trisodium citrate, and 0.1% SDS. Additional variations on these conditions will be readily apparent to those skilled in the art. Hybridization techniques are well known to those skilled in the art and are described, for example, in Benton and Davis (Science 196:180, 1977); Grunstein and Hogness (Proc. Natl. Acad. Sci., USA 72:3961, 1975); Ausubel et al. (Current Protocols in Molecular Biology, Wiley Interscience, New York, 2001); Berger and Kimmel (Guide to Molecular Cloning Techniques, 1987, Academic Press, New York); and Sambrook et al., Molecular Cloning: A Laboratory Manual, Cold Spring Harbor Laboratory Press, New York.

In general, the oligos useful in the methods described herein have at least 80% sequence complementarity to a target region within the target nucleic acid, e.g., 90%, 95%, or 100% sequence complementarity to the target region within a gene listed in Table A. For example, an antisense compound in which 18 of 20 nucleobases of the antisense oligonucleotide are complementary, and would therefore specifically hybridize, to a target region would represent 90 percent complementarity. Percent complementarity of an oligo with a region of a target nucleic acid can be determined routinely using basic local alignment search tools (BLAST programs) (Altschul et al., J. Mol. Biol., 1990, 215, 403-410; Zhang and Madden, Genome Res., 1997, 7, 649-656). Antisense and other compounds of the invention that hybridize to a gene listed in Table A are identified through routine experimentation. In general the oligos must retain specificity for their target, i.e., either do not directly bind to, or do not directly significantly affect expression levels of, transcripts other than the intended target.

Target-specific effects, with corresponding target-specific functional biological effects, are possible even when the oligo exhibits non-specific binding to a large number of non-target RNAs. For example, short 8 base long oligos that are fully complementary to a gene listed in Table A may have multiple 100% matches to hundreds of sequences in the genome, yet may produce target-specific effects, e.g. upregulation of a specific target gene through inhibition of a gene listed in Table A activity. 8-base oligos have been reported to prevent exon skipping with with a high degree of specificity and reduced off-target effect. See Singh et al., RNA Biol., 2009; 6(3): 341-350. 8-base oligos have been reported to interfere with miRNA activity without significant off-target effects. See Obad et al., Nature Genetics, 2011; 43: 371-378.

For further disclosure regarding oligos, please see US2010/0317718 (antisense oligos); US2010/0249052 (double-stranded ribonucleic acid (dsRNA)); US2009/0181914 and US2010/0234451 (LNA molecules); US2007/0191294 (siRNA analogues); US2008/0249039 (modified siRNA); and WO2010/129746 and WO2010/040112 (oligos).

Antisense

In some embodiments, the oligos are antisense oligonucleotides. Antisense oligonucleotides are typically designed to block expression of a DNA or RNA target by binding to the target and halting expression at the level of transcription, translation, or splicing. Antisense oligonucleotides of the present invention are complementary nucleic acid sequences designed to hybridize under stringent conditions to a gene listed in Table A in vitro, and are expected to inhibit the activity of a gene listed in Table A in vivo. Thus, oligonucleotides are chosen that are sufficiently complementary to the target, i.e., that hybridize sufficiently well and with sufficient biological functional specificity, to give the desired effect.

Modified Bases, Including Locked Nucleic Acids (LNAs)

In some embodiments, the oligos used in the methods described herein comprise one or more modified bonds or bases. Modified bases include phosphorothioate, methylphosphonate, peptide nucleic acids, or locked nucleic acids (LNAs). Oligos that have been modified (locked nucleic acid—LNA) have demonstrated the "on target" specificity of this approach. Preferably, the modified nucleotides are part of locked nucleic acid molecules, including [alpha]-L-LNAs. LNAs include ribonucleic acid analogues wherein the ribose ring is "locked" by a methylene bridge between the 2'-oxgygen and the 4'-carbon—i.e., oligonucleotides containing at least one LNA monomer, that is, one 2'-0,4'-C-methylene-β-D-ribofuranosyl nucleotide. LNA bases form standard Watson-Crick base pairs but the locked configuration increases the rate and stability of the basepairing reaction (Jepsen et al., Oligonucleotides, 14, 130-146 (2004)). LNAs also have increased affinity to base pair with RNA as compared to DNA. These properties render LNAs especially useful as probes for fluorescence in situ hybridization (FISH) and comparative genomic hybridization, as knockdown tools for miRNAs, and as antisense oligonucleotides to target mRNAs or other RNAs, e.g., a gene listed in Table A sequences as described herein.

The modified base/LNA molecules can include molecules comprising, e.g., 10-30, e.g., 12-24, e.g., 12, 13, 14, 15, 16, 17, 18, 19, 20, 21, 22, 23, 24, 25, 26, 27, 28, 29, or 30 nucleotides in each strand, wherein one of the strands is substantially identical, e.g., at least 80% (or more, e.g., 85%, 90%, 95%, or 100%) identical, e.g., having 3, 2, 1, or 0 mismatched nucleotide(s), to a target region in the a gene listed in Table A. The modified base/LNA molecules can be chemically synthesized using methods known in the art.

The modified base/LNA molecules can be designed using any method known in the art; a number of algorithms are known, and are commercially available (e.g., on the internet, for example at exiqon.com). See, e.g., You et al., Nuc. Acids. Res. 34:e60 (2006); McTigue et al., Biochemistry 43:5388-405 (2004); and Levin et al., Nuc. Acids. Res. 34:e142 (2006). For example, "gene walk" methods, similar to those used to design antisense oligos, can be used to optimize the inhibitory activity of a modified base/LNA molecule; for example, a series of oligonucleotides of 10-30 nucleotides spanning the length of a target gene listed in Table A can be prepared, followed by testing for activity. Optionally, gaps, e.g., of 5-10 nucleotides or more, can be left between the LNAs to reduce the number of oligonucleotides synthesized and tested. GC content is preferably between about 30-60%. General guidelines for designing modified base/LNA molecules are known in the art; for example, LNA sequences will bind very tightly to other LNA sequences, so it is preferable to avoid significant complementarity within an LNA molecule. Contiguous runs of three or more Gs or Cs, or more than four LNA residues, should be avoided where possible (for example, it may not be possible with very short (e.g., about 9-10 nt) oligonucleotides). In some embodiments, the LNAs are xylo-LNAs.

For additional information regarding LNA molecules see U.S. Pat. Nos. 6,268,490; 6,734,291; 6,770,748; 6,794,499; 7,034,133; 7,053,207; 7,060,809; 7,084,125; and 7,572,582;

and U.S. Pre-Grant Pub. Nos. 20100267018; 20100261175; and 20100035968; Koshkin et al. Tetrahedron 54, 3607-3630 (1998); Obika et al. Tetrahedron Lett. 39, 5401-5404 (1998); Jepsen et al., Oligonucleotides 14:130-146 (2004); Kauppinen et al., Drug Disc. Today 2(3):287-290 (2005); and Ponting et al., Cell 136(4):629-641 (2009), and references cited therein.

As demonstrated herein, LNA molecules can be used as a valuable tool to manipulate and aid analysis of a gene listed in Table A RNAs. Advantages offered by an LNA molecule-based system are the relatively low costs, easy delivery, and rapid action. While other oligos may exhibit effects after longer periods of time, LNA molecules exhibit effects that are more rapid, e.g., a comparatively early onset of activity, are fully reversible after a recovery period following the synthesis of new a gene listed in Table A molecules, and occur without causing substantial or substantially complete RNA cleavage or degradation. One or more of these design properties may be desired properties of the oligos of the invention. Additionally, LNA molecules make possible the systematic targeting of domains within much longer nuclear transcripts. The LNA technology enables high-throughput screens for functional analysis of a gene listed in Table A RNAs and also provides a novel tool to manipulate chromatin states in vivo for therapeutic applications.

In various related aspects, the methods described herein include using LNA molecules to target a gene listed in Table A for a number of uses, including as a research tool to probe the function of a gene listed in Table A, e.g., in vitro or in vivo. The methods include selecting one or more desired a gene listed in Table A sequences, designing one or more LNA molecules that target the a gene listed in Table A sequences, providing the designed LNA molecule, and administering the LNA molecule to a cell or animal.

In still other related aspects, the LNA molecules targeting a gene listed in Table A as described herein can be used to create animal or cell models of conditions associated with altered a gene listed in Table A expression.

Antagomirs

In some embodiments, the oligo is an antagomir. Antagomirs are chemically modified antisense oligonucleotides that can target a gene listed in Table A. For example, an antagomir for use in the methods described herein can include a nucleotide sequence sufficiently complementary to hybridize to a gene listed in Table A target sequence of about 12 to 25 nucleotides, preferably about 15 to 23 nucleotides.

In some embodiments, antagomirs include a cholesterol moiety, e.g., at the 3'-end. In some embodiments, antagomirs have various modifications for RNase protection and pharmacologic properties such as enhanced tissue and cellular uptake. For example, in addition to the modifications discussed above for antisense oligos, an antagomir can have one or more of complete or partial 2'-O-methylation of sugar and/or a phosphorothioate backbone. Phosphorothioate modifications provide protection against RNase or other nuclease activity and their lipophilicity contributes to enhanced tissue uptake. In some embodiments, the antagomir cam include six phosphorothioate backbone modifications; two phosphorothioates are located at the 5'-end and four at the 3'-end, but other patterns of phosphorothioate modification are also commonly employed and effective. See, e.g., Krutzfeldt et al., Nature 438, 685-689 (2005); Czech, N Engl J Med 2006; 354:1194-1195 (2006); Robertson et al., Silence. 1:10 (2010); Marquez and McCaffrey, Hum Gene Ther. 19(1):27-38 (2008); van Rooij et al., Circ Res. 103(9):919-928 (2008); and Liu et al., Int. J. Mol. Sci. 9:978-999 (2008). Krutzfeld et al. (2005) describe chemically engineered oligonucleotides, termed 'antagomirs', that are reported to be efficient and specific silencers of endogenous miRNAs in mice.

In general, the design of an antagomir avoids target RNA degradation due to the modified sugars present in the molecule. The presence of an unbroken string of unmodified sugars supports RNAseH recruitment and enzymatic activity. Thus, typically the design of an antagomir will include bases that contain modified sugar (e.g., LNA), at the ends or interspersed with natural ribose or deoxyribose nucleobases.

Antagomirs useful in the present methods can also be modified with respect to their length or otherwise the number of nucleotides making up the antagomir. In some embodiments, the antagomirs must retain specificity for their target, i.e., must not directly bind to, or directly significantly affect expression levels of, transcripts other than the intended target. In some embodiments, antagomirs may exhibit nonspecific binding that does not produce significant undesired biologic effect, e.g., the antagomirs do not affect expression levels of non-target transcripts or their association with regulatory proteins or regulatory RNAs.

Interfering RNA, Including siRNA/shRNA

In some embodiments, the oligo sequence that is complementary to a gene listed in Table A can be an interfering RNA, including but not limited to a small interfering RNA ("siRNA") or a small hairpin RNA ("shRNA"). Methods for constructing interfering RNAs are well known in the art. For example, the interfering RNA can be assembled from two separate oligonucleotides, where one strand is the sense strand and the other is the antisense strand, wherein the antisense and sense strands are self-complementary (i.e., each strand comprises nucleotide sequence that is complementary to nucleotide sequence in the other strand; such as where the antisense strand and sense strand form a duplex or double stranded structure); the antisense strand comprises nucleotide sequence that is complementary to a nucleotide sequence in a target nucleic acid molecule or a portion thereof (i.e., an undesired gene) and the sense strand comprises nucleotide sequence corresponding to the target nucleic acid sequence or a portion thereof. Alternatively, interfering RNA is assembled from a single oligonucleotide, where the self-complementary sense and antisense regions are linked by means of nucleic acid based or non-nucleic acid-based linker(s). The interfering RNA can be a polynucleotide with a duplex, asymmetric duplex, hairpin or asymmetric hairpin secondary structure, having self-complementary sense and antisense regions, wherein the antisense region comprises a nucleotide sequence that is complementary to nucleotide sequence in a separate target nucleic acid molecule or a portion thereof and the sense region having nucleotide sequence corresponding to the target nucleic acid sequence or a portion thereof. The interfering can be a circular single-stranded polynucleotide having two or more loop structures and a stem comprising self-complementary sense and antisense regions, wherein the antisense region comprises nucleotide sequence that is complementary to nucleotide sequence in a target nucleic acid molecule or a portion thereof and the sense region having nucleotide sequence corresponding to the target nucleic acid sequence or a portion thereof, and wherein the circular polynucleotide can be processed either in vivo or in vitro to generate an active siRNA molecule capable of mediating RNA interference.

In some embodiments, the interfering RNA coding region encodes a self-complementary RNA molecule having a sense region, an antisense region and a loop region. Such an RNA molecule when expressed desirably forms a "hairpin"

structure, and is referred to herein as an "shRNA." The loop region is generally between about 2 and about 10 nucleotides in length. In some embodiments, the loop region is from about 6 to about 9 nucleotides in length. In some embodiments, the sense region and the antisense region are between about 15 and about 20 nucleotides in length. Following post-transcriptional processing, the small hairpin RNA is converted into a siRNA by a cleavage event mediated by the enzyme Dicer, which is a member of the RNase III family. The siRNA is then capable of inhibiting the expression of a gene with which it shares homology. For details, see Brummelkamp et al., Science 296:550-553, (2002); Lee et al, Nature Biotechnol., 20, 500-505, (2002); Miyagishi and Taira, Nature Biotechnol 20:497-500, (2002); Paddison et al. Genes & Dev. 16:948-958, (2002); Paul, Nature Biotechnol, 20, 505-508, (2002); Sui, Proc. Natl. Acad. Sd. USA, 99(6), 5515-5520, (2002); Yu et al. Proc NatlAcadSci USA 99:6047-6052, (2002).

The target RNA cleavage reaction guided by siRNAs is highly sequence specific. In general, siRNA containing a nucleotide sequences identical to a portion of the target nucleic acid are preferred for inhibition. However, 100% sequence identity between the siRNA and the target gene is not required to practice the present invention. Thus the invention has the advantage of being able to tolerate sequence variations that might be expected due to genetic mutation, strain polymorphism, or evolutionary divergence. For example, siRNA sequences with insertions, deletions, and single point mutations relative to the target sequence have also been found to be effective for inhibition. Alternatively, siRNA sequences with nucleotide analog substitutions or insertions can be effective for inhibition. In general the siRNAs must retain specificity for their target, i.e., must not directly bind to, or directly significantly affect expression levels of, transcripts other than the intended target.

Ribozymes

In some embodiments, the oligos are ribozymes. Trans-cleaving enzymatic nucleic acid molecules can also be used; they have shown promise as therapeutic agents for human disease (Usman & McSwiggen, 1995 Ann. Rep. Med. Chem. 30, 285-294; Christoffersen and Marr, 1995 J. Med. Chem. 38, 2023-2037). Enzymatic nucleic acid molecules can be designed to cleave specific caRNA targets within the background of cellular RNA. Such a cleavage event renders the caRNA non-functional.

In general, enzymatic nucleic acids with RNA cleaving activity act by first binding to a target RNA. Such binding occurs through the target binding portion of an enzymatic nucleic acid which is held in close proximity to an enzymatic portion of the molecule that acts to cleave the target RNA. Thus, the enzymatic nucleic acid first recognizes and then binds a target RNA through complementary base pairing, and once bound to the correct site, acts enzymatically to cut the target RNA. Strategic cleavage of such a target RNA will destroy its ability to direct synthesis of an encoded protein. After an enzymatic nucleic acid has bound and cleaved its RNA target, it is released from that RNA to search for another target and can repeatedly bind and cleave new targets.

Several approaches such as in vitro selection (evolution) strategies (Orgel, 1979, Proc. R. Soc. London, B 205, 435) have been used to evolve new nucleic acid catalysts capable of catalyzing a variety of reactions, such as cleavage and ligation of phosphodiester linkages and amide linkages, (Joyce, 1989, Gene, 82, 83-87; Beaudry et al., 1992, Science 257, 635-641; Joyce, 1992, Scientific American 267, 90-97; Breaker et al, 1994, TIBTECH 12, 268; Bartel et al, 1993, Science 261:1411-1418; Szostak, 1993, TIBS 17, 89-93; Kumar et al, 1995, FASEB J., 9, 1183; Breaker, 1996, Curr. Op. Biotech., 1, 442). The development of ribozymes that are optimal for catalytic activity would contribute significantly to any strategy that employs RNA-cleaving ribozymes for the purpose of regulating gene expression. The hammerhead ribozyme, for example, functions with a catalytic rate (kcat) of about 1 $min^{-1}$ in the presence of saturating (10 MM) concentrations of $Mg^{2+}$ cofactor. An artificial "RNA ligase" ribozyme has been shown to catalyze the corresponding self-modification reaction with a rate of about 100 $min^{-1}$. In addition, it is known that certain modified hammerhead ribozymes that have substrate binding arms made of DNA catalyze RNA cleavage with multiple turn-over rates that approach 100 $min^{-1}$.

Making and Using Oligos

The nucleic acid sequences used to practice the methods described herein, whether RNA, cDNA, genomic DNA, vectors, viruses or hybrids thereof, can be isolated from a variety of sources, genetically engineered, amplified, and/or expressed/generated recombinantly. If desired, nucleic acid sequences of the invention can be inserted into delivery vectors and expressed from transcription units within the vectors. The recombinant vectors can be DNA plasmids or viral vectors. Generation of the vector construct can be accomplished using any suitable genetic engineering techniques well known in the art, including, without limitation, the standard techniques of PCR, oligonucleotide synthesis, restriction endonuclease digestion, ligation, transformation, plasmid purification, and DNA sequencing, for example as described in Sambrook et al. Molecular Cloning: A Laboratory Manual. (1989)), Coffin et al. (Retroviruses. (1997)) and "RNA Viruses: A Practical Approach" (Alan J. Cann, Ed., Oxford University Press, (2000)).

Preferably, oligos of the invention are synthesized chemically. Nucleic acid sequences used to practice this invention can be synthesized in vitro by well-known chemical synthesis techniques, as described in, e.g., Adams (1983) J. Am. Chem. Soc. 105:661; Belousov (1997) Nucleic Acids Res. 25:3440-3444; Frenkel (1995) Free Radic. Biol. Med. 19:373-380; Blommers (1994) Biochemistry 33:7886-7896; Narang (1979) Meth. Enzymol. 68:90; Brown (1979) Meth. Enzymol. 68:109; Beaucage (1981) Tetra. Lett. 22:1859; U.S. Pat. No. 4,458,066; WO/2008/043753 and WO/2008/049085, and the refences cited therein.

Nucleic acid sequences of the invention can be stabilized against nucleolytic degradation such as by the incorporation of a modification, e.g., a nucleotide modification. For example, nucleic acid sequences of the invention includes a phosphorothioate at least the first, second, or third internucleotide linkage at the 5' or 3' end of the nucleotide sequence. As another example, the nucleic acid sequence can include a 2'-modified nucleotide, e.g., a 2'-deoxy, 2'-deoxy-2'-fluoro, 2'-O-methyl, 2'-O-methoxyethyl (2'-O-MOE), 2'-O-aminopropyl (2'-O-AP), 2'-O-dimethylaminoethyl (2'-O-DMAOE), 2'-O-dimethylaminopropyl (2'-O-DMAP), 2'-O-dimethylaminoethyloxyethyl (2'-O-DMAEOE), or 2'-O—N-methylacetamido (2'-O-NMA). As another example, the nucleic acid sequence can include at least one 2'-O-methyl-modified nucleotide, and in some embodiments, all of the nucleotides include a 2'-O-methyl modification. In some embodiments, the nucleic acids are "locked," i.e., comprise nucleic acid analogues in which the ribose ring is "locked" by a methylene bridge connecting the 2'-0 atom and the 4'-C atom (see, e.g., Kaupinnen et al., Drug Disc. Today 2(3):287-290 (2005); Koshkin et al., J. Am.

Chem. Soc., 120(50):13252-13253 (1998)). For additional modifications see US 20100004320, US 20090298916, and US 20090143326.

It is understood that any of the modified chemistries or formats of oligos described herein can be combined with each other, and that one, two, three, four, five, or more different types of modifications can be included within the same molecule.

Techniques for the manipulation of nucleic acids used to practice this invention, such as, e.g., subcloning, labeling probes (e.g., random-primer labeling using Klenow polymerase, nick translation, amplification), sequencing, hybridization and the like are well described in the scientific and patent literature, see, e.g., Sambrook et al., Molecular Cloning; A Laboratory Manual 3d ed. (2001); Current Protocols in Molecular Biology, Ausubel et al., eds. (John Wiley & Sons, Inc., New York 2010); Kriegler, Gene Transfer and Expression: A Laboratory Manual (1990); Laboratory Techniques In Biochemistry And Molecular Biology: Hybridization With Nucleic Acid Probes, Part I. Theory and Nucleic Acid Preparation, Tijssen, ed. Elsevier, N.Y. (1993).

Modification Patterns

In some embodiments, the inhibitory oligonucleotide comprises locked nucleic acids (LNA), ENA modified nucleotides, 2'-O-methyl nucleotides, or 2'-fluoro-deoxyribonucleotides. In some embodiments, the inhibitory oligonucleotide comprises alternating deoxyribonucleotides and 2'-fluoro-deoxyribonucleotides. In some embodiments, the inhibitory oligonucleotide comprises alternating deoxyribonucleotides and 2'-O-methyl nucleotides. In some embodiments, the inhibitory oligonucleotide comprises alternating deoxyribonucleotides and ENA modified nucleotides. In some embodiments, the inhibitory oligonucleotide comprises alternating deoxyribonucleotides and locked nucleic acid nucleotides. In some embodiments, the inhibitory oligonucleotide comprises alternating locked nucleic acid nucleotides and 2'-O-methyl nucleotides.

The oligonucleotide may comprise deoxyribonucleotides flanked by at least one bridged nucleotide (e.g., a LNA nucleotide, cEt nucleotide, ENA nucleotide) on each of the 5' and 3' ends of the deoxyribonucleotides. The oligonucleotide may comprise deoxyribonucleotides flanked by 1, 2, 3, 4, 5, 6, 7, 8 or more bridged nucleotides (e.g., LNA nucleotides, cEt nucleotides, ENA nucleotides) on each of the 5' and 3' ends of the deoxyribonucleotides. In some embodiments, the 5' nucleotide of the oligonucleotide is a deoxyribonucleotide. In some embodiments, the 5' nucleotide of the oligonucleotide is a locked nucleic acid nucleotide. In some embodiments, the nucleotides of the oligonucleotide comprise deoxyribonucleotides flanked by at least one locked nucleic acid nucleotide on each of the 5' and 3' ends of the deoxyribonucleotides. In some embodiments, the nucleotide at the 3' position of the oligonucleotide has a 3' hydroxyl group or a 3' thiophosphate.

In some embodiments, the inhibitory oligonucleotide comprises phosphorothioate internucleotide linkages. In some embodiments, the single stranded oligonucleotide comprises phosphorothioate internucleotide linkages between at least two nucleotides. In some embodiments, the single stranded oligonucleotide comprises phosphorothioate internucleotide linkages between all nucleotides.

It should be appreciated that the oligonucleotide can have any combination of modifications as described herein.

As an example, the oligonucleotide may comprise a nucleotide sequence having one or more of the following modification patterns.

(a) (X)Xxxxxx, (X)xXxxxx, (X)xxXxxx, (X)xxxXxx, (X)xxxxXx and (X)xxxxxX, (b) (X)XXxxxx, (X)XxXxxx, (X)XxxXxx, (X)XxxxXx, (X)XxxxxX, (X)xXXxxx, (X)xXxXxx, (X)xXxxXx, (X)xXxxxX, (X)xxXXxx, (X)xxXxXx, (X)xxXxxX, (X)xxxXXx, (X)xxxXxX and (X)xxxxXX, (c) (X)XXXxxx, (X)xXXXxx, (X)xxXXXx, (X)xxxXXX, (X)XXxXxx, (X)XXxxXx, (X)XXxxxX, (X)xXXxXx, (X)xXXxxX, (X)xxXXxX, (X)XxXXxx, (X)XxxXXx, (X)XxxxXX, (X)XxxxXX, (X)xXxXXx, (X)xXxxXX, (X)xxXxXX, (X)xXxXxX and (X)XxXxXx, (d) (X)xxXXXX, (X)xXxXXX, (X)xXXxXX, (X)xXXXxX, (X)xXXXXx, (X)XxxXXXX, (X)XxXxXX, (X)XxXXxX, (X)XxXXx, (X)XXxxXX, (X)XXxXxX, (X)XXxXXx, (X)XXXxxX, (X)XXXxXx, and (X)XXXXxx, (e) (X)xXXXXX, (X)XxXXXX, (X)XXxXXX, (X)XXXxXX, (X)XXXXxX and (X)XXXXXx, and (f) XXXXXX, XxXXXXX, XXxXXXX, XXXxXXX, XXXXxXX, XXXXXxX and XXXXXXx, in which "X" denotes a nucleotide analogue, (X) denotes an optional nucleotide analogue, and "x" denotes a DNA or RNA nucleotide unit. Each of the above listed patterns may appear one or more times within an oligonucleotide, alone or in combination with any of the other disclosed modification patterns.

In some embodiments, the oligonucleotide is a gapmer (contain a central stretch (gap) of DNA monomers sufficiently long to induce RNase H cleavage, flanked by blocks of LNA modified nucleotides; see, e.g., Stanton et al., Nucleic Acid Ther. 2012. 22: 344-359; Nowotny et al., Cell, 121:1005-1016, 2005; Kurreck, European Journal of Biochemistry 270: 1628-1644, 2003; FLuiter et al., Mol Biosyst. 5(8):838-43, 2009). In some embodiments, the oligonucleotide is a mixmer (includes alternating short stretches of LNA and DNA; Naguibneva et al., Biomed Pharmacother. 2006 November; 60(9):633-8; Orom et al., Gene. 2006 May 10; 3720:137-41).

Additional Sequence Structural Information

The inhibitory oligonucleotides described herein may have a sequence that does not contain guanosine nucleotide stretches (e.g., 3 or more, 4 or more, 5 or more, 6 or more consecutive guanosine nucleotides). In some embodiments, oligonucleotides having guanosine nucleotide stretches have increased non-specific binding and/or off-target effects, compared with oligonucleotides that do not have guanosine nucleotide stretches.

The inhibitory oligonucleotides have a sequence that has less than a threshold level of sequence identity with every sequence of nucleotides, of equivalent length, that map to a genomic position encompassing or in proximity to an off-target gene. For example, an oligonucleotide may be designed to ensure that it does not have a sequence that maps to genomic positions encompassing or in proximity with all known genes (e.g., all known protein coding genes) other than the gene of interest. The oligonucleotide is expected to have a reduced likelihood of having off-target effects. The threshold level of sequence identity may be 50%, 60%, 70%, 80%, 85%, 90%, 95%, 99% or 100% sequence identity.

The inhibitory oligonucleotides may have a sequence that is complementary to a region that encodes an RNA that forms a secondary structure comprising at least two single stranded loops. In some embodiments, oligonucleotides that are complementary to a region that encodes an RNA that forms a secondary structure comprising one or more single stranded loops (e.g., at least two single stranded loops) have a greater likelihood of being active (e.g., of being capable of activating or enhancing expression of a target gene) than a randomly selected oligonucleotide. In some cases, the secondary structure may comprise a double stranded stem between the at least two single stranded loops. Accordingly, the area of complementarity between the oligonucleotide and the nucleic acid region may be at a location of the PRC2 associated region that encodes at least a portion of at least one of the loops. In some embodiments, the predicted secondary structure RNA (e.g., of the a gene listed in Table A sequence) containing the nucleic acid region is determined using RNA secondary structure prediction algorithms, e.g., RNAfold, mfold. In some embodiments, oligonucleotides are designed to target a region of the RNA that forms a secondary structure comprising one or more single stranded loop (e.g., at least two single stranded loops) structures which may comprise a double stranded stem between the at least two single stranded loops.

The inhibitory oligonucleotide may have a sequence that is has greater than 30% G-C content, greater than 40% G-C content, greater than 50% G-C content, greater than 60% G-C content, greater than 70% G-C content, or greater than 80% G-C content. The inhibitory oligonucleotide may have a sequence that has up to 100% G-C content, up to 95% G-C content, up to 90% G-C content, or up to 80% G-C content.

In some embodiments, the region of complementarity of the inhibitory oligonucleotide is complementary with at least 8 to 15, 8 to 30, 8 to 40, or 10 to 50, or 5 to 50, or 5 to 40 bases, e.g., 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 consecutive nucleotides of a gene listed in Table A as known in the art or disclosed herein. In some embodiments, the region of complementarity is complementary with at least 8, 10, 12, 14, 16, 18, or 20 consecutive nucleotides of a gene listed in Table A as known in the art or disclosed herein.

Antibodies

Antibodies that specifically bind to and inhibit a target listed in Table A can be used disrupt Type 1 interferon signaling and cause reduction in neuronal cell death in response to dsRNA, and therefore be used to treat neurodegenerative diseases as described herein.

The term "antibody" as used herein refers to an immunoglobulin molecule or an antigen-binding portion thereof. Examples of antigen-binding portions of immunoglobulin molecules include F(ab) and F(ab')$_2$ fragments, which retain the ability to bind antigen. The antibody can be polyclonal, monoclonal, recombinant, chimeric, de-immunized or humanized, fully human, non-human, (e.g., murine), or single chain antibody. In some embodiments the antibody has effector function and can fix complement. In some embodiments, the antibody has reduced or no ability to bind an Fc receptor. For example, the antibody can be an isotype or subtype, fragment or other mutant, which does not support binding to an Fc receptor, e.g., it has a mutagenized or deleted Fc receptor binding region. Methods for making antibodies and fragments thereof are known in the art, see, e.g., Harlow et. al., editors, Antibodies: A Laboratory Manual (1988); Goding, Monoclonal Antibodies: Principles and Practice, (N.Y Academic Press 1983); Howard and Kaser, Making and Using Antibodies: A Practical Handbook (CRC Press; 1st edition, Dec. 13, 2006); Kontermann and Duibel, Antibody Engineering Volume 1 (Springer Protocols) (Springer; 2nd ed., May 21, 2010); Lo, Antibody Engineering: Methods and Protocols (Methods in Molecular Biology) (Humana Press; Nov. 10, 2010); and Dibel, Handbook of Therapeutic Antibodies: Technologies, Emerging Developments and Approved Therapeutics, (Wiley-VCH; 1 edition Sep. 7, 2010).

Antibodies that bind to the targets listed in Table A are known in the art and can be obtained from commercial sources.

Methods of Screening

Based on the work described herein, the present disclosure provides methods for identifying compounds that decrease cell death (apoptosis) in neurons in response to dsRNA, for treating neurodegenerative diseases; in some embodiments, the compounds target genes or proteins in the type 1 interferon dsRNA STAT response pathway, i.e., human interferon alpha 16, TLR3, Eif2ak2 (PKR), MDA5, MAVS, Stat1, Oasl2, Ifih1, Ifi44, DDX58, and RNaseL; or in the p38 pathway, i.e., p38, MapKapK-2 and MapKapK-3. These compounds are useful in inhibiting components in these signaling pathways that lead to neurodegeneration.

Included herein are methods for screening test compounds, e.g., polypeptides, polynucleotides, inorganic or organic large or small molecule test compounds, to identify agents useful in the treatment of disorders associated with neurodegeneration.

As used herein, "small molecules" refers to small organic or inorganic molecules of molecular weight below about 3,000 Daltons. In general, small molecules useful for the invention have a molecular weight of less than 3,000 Daltons (Da). The small molecules can be, e.g., from at least about 100 Da to about 3,000 Da (e.g., between about 100 to about 3,000 Da, about 100 to about 2500 Da, about 100 to about 2,000 Da, about 100 to about 1,750 Da, about 100 to about 1,500 Da, about 100 to about 1,250 Da, about 100 to about 1,000 Da, about 100 to about 750 Da, about 100 to about 500 Da, about 200 to about 1500, about 500 to about 1000, about 300 to about 1000 Da, or about 100 to about 250 Da).

The test compounds can be, e.g., natural products or members of a combinatorial chemistry library. A set of diverse molecules should be used to cover a variety of functions such as charge, aromaticity, hydrogen bonding, flexibility, size, length of side chain, hydrophobicity, and rigidity. Combinatorial techniques suitable for synthesizing small molecules are known in the art, e.g., as exemplified by Obrecht and Villalgordo, *Solid-Supported Combinatorial and Parallel Synthesis of Small-Molecular-Weight Compound Libraries*, Pergamon-Elsevier Science Limited (1998), and include those such as the "split and pool" or "parallel" synthesis techniques, solid-phase and solution-phase techniques, and encoding techniques (see, for example, Czarnik, Curr. Opin. Chem. Bio. 1:60-6 (1997)). In addition, a number of small molecule libraries are commercially available. A number of suitable small molecule test compounds are listed in U.S. Pat. No. 6,503,713, incorporated herein by reference in its entirety.

Libraries screened using the methods of the present invention can comprise a variety of types of test compounds. A given library can comprise a set of structurally related or unrelated test compounds. In some embodiments, the test compounds are peptide or peptidomimetic molecules. In some embodiments, the test compounds are nucleic acids.

In some embodiments, the test compounds and libraries thereof can be obtained by systematically altering the structure of a first test compound, e.g., a first test compound that is structurally similar to a known natural binding partner of the target polypeptide, or a first small molecule identified as capable of binding the target polypeptide, e.g., using methods known in the art or the methods described herein, and correlating that structure to a resulting biological activity, e.g., a structure-activity relationship study. As one of skill in the art will appreciate, there are a variety of standard methods for creating such a structure-activity relationship. Thus, in some instances, the work may be largely empirical, and in others, the three-dimensional structure of an endogenous polypeptide or portion thereof can be used as a starting point for the rational design of a small molecule compound or compounds. For example, in one embodiment, a general library of small molecules is screened, e.g., using the methods described herein.

In some embodiments, a test compound is applied to a test sample, e.g., a cell or living tissue or organ, e.g., an eye, and one or more effects of the test compound is evaluated. In a cultured or primary cell for example, the ability of the test compound to protect the cell from death in the presence of dsRNA or synthetic dsRNA-mimetics, or to reduce expression or activity of a target gene listed in Table A, can be assayed. For example, a cell, e.g., a neuron, that includes an inducible antisense-coding sequence, e.g., a sequence that encodes an antisense transcript that is at least 35 nt long, and is complementary to a sense transcript that is expressed in the cell, e.g., an endogenous sense transcript (preferably for a non-essential gene) or to a sense transcript that is expressed from an exogenous coding sequence. The sense transcript can be, but need not be, all or part of a protein-coding transcript. The cells can be primary cells, e.g., from a transgenic animal that contains both the sense and antisense coding sequences in the germline, or can be cultured, e.g., wherein the sense or the antisense coding sequence is transfected into the cell. In some embodiments, one or both of the transcript and the antisense are linked to and under the control of an inducible promoter. In the cells, rates of apoptosis can be evaluated using methods known in the art, e.g., caspase expression or TUNEL assays. Expression of the sense and antisense coding sequences is induced if needed, and the cell is contacted with the test compound. A compound that decreases apoptosis in the cells is selected as a candidate compound.

Methods for evaluating effects on levels or activity of the genes and proteins are known in the art. For example, ability to modulate expression of a protein can be evaluated at the gene or protein level, e.g., using quantitative PCR or immunoassay methods. In some embodiments, high throughput methods, e.g., protein or gene chips as are known in the art (see, e.g., Ch. 12, Genomics, in Griffiths et al., Eds. Modern genetic Analysis, 1999,W. H. Freeman and Company; Ekins and Chu, Trends in Biotechnology, 1999, 17:217-218; MacBeath and Schreiber, Science 2000, 289(5485):1760-1763; Simpson, Proteins and Proteomics: A Laboratory Manual, Cold Spring Harbor Laboratory Press; 2002; Hardiman, Microarrays Methods and Applications: Nuts & Bolts, DNA Press, 2003), can be used to detect an effect on protein or transcript levels of any of the targets listed in Table A. Ability to modulate signaling via the type 1 interferon pathway can be evaluated, e.g., using assays that detect levels of pSTAT1 or a kinase substrate in the p38/MAPK1 pathway. The cell can be cultured using methods known in the art, e.g., traditional (two-dimensional, on a plate or in suspension) or three-dimensional culture systems (e.g., as described in Choi et al., A three-dimensional human neural cell culture model of Alzheimer's disease. Nature. 2014 Oct. 12. doi: 10.1038/nature13800; assays as described in Choi et al., 2014 can also be used.).

In some embodiments, the test sample is an in vivo model of a disorder as described herein. For example, an animal model, e.g., a rodent such as a rat, can be used, wherein the animal expresses an inducible antisense in its neurons, or is infected with a virus encoding the antisense, dsRNA, or containing a dsRNA intermediate. Alternatively, an animal model in which a dsRNA of 35 nts or longer is produced can also be used, e.g., the Nd1 or Nd2 mouse models described herein. In these animal models, rates of neurodegeneration can be evaluated, e.g., using structural (e.g., histochemical or immunohistochemical analysis of cell death or PET imaging of olfactory neurons), functional analysis (e.g., including electrophysiologic or in vivo imaging) and/or behavioral analysis (e.g., psychometric testing or olfactory behavioral analysis based on responses to odors with innate aversive or attractive responses, e.g., as described in Cao et al., Sci Rep. 2012; 2(231): 1-8 and Liberles, Annual review of physiology. 2014; 76:151-75). A compound that decreases rates or parameters associated with neurodegeneration, e.g., improves in trajectory of psychometric testing, reduction or delay/slowing of brain atrophy on MRI, reversal of hypometabolism on PET imaging, or delayed or decreased progression of amyloid or tau pathology on PET imaging, is selected as a test compound. Alternatively or in addition, an effect on levels or activity of a transcript or protein listed in Table A can be evaluated in samples or cells from the animal, e.g., in samples or cells from the brain of the animal.

A test compound that has been screened by a method described herein and determined to reduce apoptosis, cell death or other markers such as RNA expression signature, interferon signature, can be considered a candidate compound. A candidate compound that has been screened, e.g., in an in vivo model of a disorder as described herein, and determined to have a desirable effect on the disorder, e.g., on one or more symptoms of the disorder, can be considered a candidate therapeutic agent. Candidate therapeutic agents, once screened in a clinical setting, are therapeutic agents. Candidate compounds, candidate therapeutic agents, and therapeutic agents can be optionally optimized and/or derivatized, and formulated with physiologically acceptable excipients to form pharmaceutical compositions.

Thus, test compounds identified as "hits" (e.g., test compounds that reduce cell death) in a first screen can be selected and systematically altered, e.g., using rational design, to optimize binding affinity, avidity, specificity, or other parameter. Such optimization can also be screened for using the methods described herein. Thus, in one embodiment, the invention includes screening a first library of compounds using a method known in the art and/or described herein, identifying one or more hits in that library, subjecting those hits to systematic structural alteration to create a second library of compounds structurally related to the hit, and screening the second library using the methods described herein.

Test compounds identified as hits can be considered candidate therapeutic compounds, useful in treating disorders associated with neurodegeneration as described herein. A variety of techniques useful for determining the structures of "hits" can be used in the methods described herein, e.g., NMR, mass spectrometry, gas chromatography equipped with electron capture detectors, fluorescence and absorption spectroscopy. Thus, the invention also includes compounds identified as "hits" by the methods described herein, and methods for their administration and use in the treatment, prevention, or delay of development or progression of a disorder described herein.

Test compounds identified as candidate therapeutic compounds can be further screened by administration to an animal model of a disorder associated with neurodegeneration as described herein. The animal can be monitored for a change in the disorder, e.g., for an improvement in a parameter of the disorder, e.g., a parameter related to clinical outcome. In some embodiments, the parameter is cell death and an improvement would be reduction or delay in cell death. In some embodiments, the subject is a human, e.g., a human with a neurodegenerative disease, and the parameter is retention of function or delay in symptoms of neurodegeneration.

Pharmaceutical Compositions and Methods of Administration

The methods described herein include the use and manufacture of pharmaceutical compositions comprising as an active ingredient a compound that decreases apoptosis in neurons in response to dsRNA, e.g., a compound that targets genes or proteins in the type 1 interferon dsRNA response STAT pathway, i.e., human interferon alpha 16, TLR3, Eif2ak2 (PKR), MDA5, MAVS, Stat1, Oasl2, Ifih1, Ifi44, and RNaseL; or in the p38 pathway, i.e., p38, MapKapK-2 and MapKapK-3, or a compound identified by a method described herein.

Pharmaceutical compositions typically include a pharmaceutically acceptable carrier. As used herein the language "pharmaceutically acceptable carrier" includes saline, solvents, dispersion media, coatings, antibacterial and antifungal agents, isotonic and absorption delaying agents, and the like, compatible with pharmaceutical administration. Supplementary active compounds can also be incorporated into the compositions, e.g., anti-tau agents, such as other kinase inhibitors, e.g. lithium, GSK inhibitors, e.g., or anti-tau antibodies; Insulin or insulin agonists; Statins, e.g., simvastatin; other modulators of different components of the innate immune system, such as microglial modulators; or HDAC inhibitors.

Pharmaceutical compositions are typically formulated to be compatible with its intended route of administration. Examples of routes of administration include parenteral, e.g., intravenous, intradermal, subcutaneous, oral (e.g., inhalation), transdermal (topical), transmucosal, and rectal administration.

Methods of formulating suitable pharmaceutical compositions are known in the art, see, e.g., *Remington: The Science and Practice of Pharmacy*, 21st ed., 2005; and the books in the series *Drugs and the Pharmaceutical Sciences: a Series of Textbooks and Monographs* (Dekker, NY). For example, solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use can include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the composition must be sterile and should be fluid to the extent that easy syringability exists. It should be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyetheylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as mannitol, sorbitol, sodium chloride in the composition. Prolonged absorption of the injectable compositions can be brought about by including in the composition an agent that delays absorption, for example, aluminum monostearate and gelatin.

Sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle, which contains a basic dispersion medium and the required other ingredients from those enumerated above. In the case of sterile powders for the preparation of sterile injectable solutions, the preferred methods of preparation are vacuum drying and freeze-drying, which yield a powder of the active ingredient plus any additional desired ingredient from a previously sterile-filtered solution thereof.

Oral compositions generally include an inert diluent or an edible carrier. For the purpose of oral therapeutic administration, the active compound can be incorporated with excipients and used in the form of tablets, troches, or capsules, e.g., gelatin capsules. Oral compositions can also be prepared using a fluid carrier for use as a mouthwash. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compounds can be delivered in the form of an aerosol spray from a pressured container or dispenser that contains a suitable propellant, e.g., a gas such as carbon dioxide, or a nebulizer. Such methods include those described in U.S. Pat. No. 6,468,798.

Systemic administration of a therapeutic compound as described herein can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The pharmaceutical compositions can also be prepared in the form of suppositories (e.g., with conventional suppository bases such as cocoa butter and other glycerides) or retention enemas for rectal delivery.

Therapeutic compounds that are or include nucleic acids can be administered by any method suitable for administration of nucleic acid agents. These methods include gene guns, bio injectors, and skin patches as well as needle-free methods such as the micro-particle DNA vaccine technology disclosed in U.S. Pat. No. 6,194,389, and the mammalian transdermal needle-free vaccination with powder-form vaccine as disclosed in U.S. Pat. No. 6,168,587. Additionally, intranasal delivery is possible, as described in, inter alia, Hamajima et al., Clin. Immunol. Immunopathol., 88(2), 205-10 (1998). Liposomes (e.g., as described in U.S. Pat. No. 6,472,375) and microencapsulation can also be used. Biodegradable targetable microparticle delivery systems can also be used (e.g., as described in U.S. Pat. No. 6,471,996).

In one embodiment, the therapeutic compounds are prepared with carriers that will protect the therapeutic compounds against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Such formulations can be prepared using standard techniques, or obtained commercially, e.g., from Alza Corporation and Nova Pharmaceuticals, Inc. Liposomal suspensions (including liposomes targeted to selected cells with monoclonal antibodies to cellular antigens) can also be used as pharmaceutically acceptable carriers. These can be prepared according to methods known to those skilled in the art, for example, as described in U.S. Pat. No. 4,522,811.

The pharmaceutical compositions can be included in a container, pack, or dispenser together with instructions for administration.

Transgenic Animals

Also described herein are mouse lines Nd1, Nd2, and CORMAWG and their uses for identification and validation of other novel targets for neurodegeneration, propagation of neurodegeneration, and Alzheimer's disease pathogenesis as well as for purposes of drug screening and validation with the primary outcome being loss of neurons.

As used herein, a "transgenic animal" is a non-human animal, preferably a mammal, more preferably a rodent such as a rat or mouse, in which one or more of the cells of the animal includes a transgene as described herein. Other examples of transgenic animals include non-human primates, sheep, dogs, cows, goats, pigs, chickens, amphibians, and the like. A transgene can be exogenous DNA, e.g., that results in expression of an exogenous gene or in increased expression of an endogenous gene, or a rearrangement, e.g., a deletion of endogenous chromosomal DNA, which preferably is integrated into or occurs in the genome of the cells of a transgenic animal, in which insertion of the transgene into the genome included chromothripsis such that an antisense is also transcribed. Thus, a transgenic animal is one in which the transgene has been introduced, optionally by homologous recombination between part an endogenous gene and an exogenous DNA molecule (the transgene) introduced into a cell of the animal, e.g., an embryonic cell of the animal, prior to development of the animal. In some embodiments, the transgenic animals include human APP genes, e.g., comprising a wild type APP, or pathogenic APP (e.g., comprising mutations K670M/N and M671L, also known as the Swedish allele, see Ponte et al. (1988) Nature 331: 525; and Kitaguchi et al. (1988) Nature 331: 530; US 20040016008 and WO 1995011968) or synthetic APP.

In some embodiments, the transgenic animals comprise transgenes that result in overexpression of MDA5, constitutively activated PKR, or MAVS. Sequences encoding each of these are known in the art. For example, sequences for human MDA5 and MAVS are shown in Table A. Mouse sequences for MAVS are in GenBank at Acc. No. NM_144888.2 (variant 1, mRNA) and NM_001206385.1 (variant 2, mRNA), which both encode NP_659137.1 (isoform 1), and NM_001206382.1 (variant 3, mRNA) and NM_001206383.1 (variant 4, mRNA), both of which encode NP_001193311.1 (isoform 2). Mouse sequences for MDA5 are in GenBank at Acc. No. NM_027835.3 (variant 1, mRNA) encoding NP_082111.2 (isoform 1, protein) and NM_001164477.1 (variant 2, mRNA) encoding NP_001157949.1 (isoform 2, protein).

The sequences for human PKR (also known as EIF2AK2, or eukaryotic translation initiation factor 2-alpha kinase 2) are in GenBank at Acc. No. NM_002759.3 (variant 1) or NM_001135651.2 (variant 2, mRNA), which both encode NP_001129123.1 (isoform a, protein), or NM_001135652.2 (variant 3, mRNA), which encodes NP_001129124.1 (isoform b). Mouse sequences for PKR are in GenBank at Acc. No. NM_011163.4 (mRNA) and NP_035293.1 (protein). Mutations of D328 and D333 (numbering relative to the human sequence), e.g., to alanine, produce a constitutively active PKR.

Intronic sequences and polyadenylation signals can also be included in the transgene to increase the efficiency of expression of the transgene. A tissue-specific regulatory sequence(s) can be operably linked to a transgene of the invention to direct expression of a protein to particular cells. A transgenic founder animal can be identified based upon the presence of a sense coding sequence and the antisense coding sequence in its genome and/or expression of sense and antisense in tissues or cells of the animals. A transgenic founder animal can then be used to breed additional animals carrying the transgene. Moreover, transgenic animals carrying a sense and antisense transgene can further be bred to other transgenic animals carrying other transgenes. In some embodiments, the transgenic animals are the Nd1 or Nd2 mice.

Also included herein are cells and populations of cells from a transgenic animal, as discussed, e.g., below.

Methods of Treatment

Based on the work described herein, the present disclosure provides methods for treating neurodegenerative diseases based on targeting genes in the type 1 interferon dsRNA STAT response pathway, i.e., human interferon alpha 16, TLR3, Eif2ak2 (PKR), MDA5, MAVS, Stat1, Oasl2, Ifih1, Ifi44, and RNaseL; or in the p38 pathway, i.e., p38, MapKapK-2 and MapKapK-3, targeting components in these signaling pathways that lead to neurodegeneration. Interference with one or more of these targets can be used to prevent neurodegeneration in Alzheimer's disease and other neurodegenerative diseases in vivo.

The methods described herein include methods for the treatment of disorders associated with neurodegeneration. In some embodiments, the disorder is Alzheimer's disease, amyotrophic lateral sclerosis (e.g., C9orf72-linked ALS), frontotemporal dementia, Cockayne Syndrome (CS), Xeroderma Pigmentosum (XP), Trichothiodystrophy (TTD), Ataxia with Occulomotor Apraxia-1 (AOA1), Spinocerebellar Ataxia with Axonal Neuropathy (SCAN1), Ataxia Telangiectasia (A-T) or A-T Like Disease (ATLD), ATR-Seckel Syndrome, Nijmegen Breakage Syndrome (NBS), LIG4 Syndrome, Aicardi-Goutier's syndrome and related interferonopathies, or XLF Syndrome. In some embodiments the disease is associated with a mutation in a DNA repair genes (see, e.g., Madabhushi et al., 83(2):p 266-282 (2014)).

Generally, the methods include administering a therapeutically effective amount of a compound that targets a gene or protein in the Type 1 interferon signaling pathway as described herein (e.g., as listed in Table A), to a subject who is in need of, or who has been determined to be in need of, such treatment.

As used in this context, to "treat" means to ameliorate at least one symptom or sign of the disorder associated with neurodegeneration, e.g., improvement in trajectory of psychometric testing, reduction or delay/slowing of brain atrophy on MRI, reversal of hypometabolism on PET imaging, decreased progression of or amyloid or tau pathology on PET imaging. Often, neurodegeneration results in a loss of cognitive, sensory, or physical (motor) function; thus, a treatment can result in a reduction in rate or severity of loss of cognitive, sensory or physical (motor) function and a return or approach to normal cognitive, sensory or physical (motor) function, or preservation of cognitive or physical function. Administration of a therapeutically effective amount of a compound described herein for the treatment of a condition associated with neurodegeneration will result in decreased neuronal cell death.

EXAMPLES

The invention is further described in the following examples, which do not limit the scope of the invention described in the claims.

Example 1. Cytoplasmic Double Stranded RNA Links Genomic Lesions with Propagated Neurodegeneration in Mice Here, we describe 2 independent mouse transgenes that underwent chromothripsis, a complex genetic event resulting from multiple DSBs, that caused inversions, insertions and deletions at the site of transgenic integration. These transgenic mice allowed us to evaluate the effects of chromothripsis at a defined genetic locus and within a defined neuronal population. Expression of these complicated transgenes exclusively in mature olfactory sensory neurons (OSNs) leads to an increase in both an autonomous and non-cell-autonomous loss of neurons. A more detailed analysis revealed the expression of each strand of an inverted duplication of the transgene, which produces double-stranded RNA (dsRNA). Combining mouse genetics with adenoviral associated vectors (AAVs) we demonstrate that cytoplasmic dsRNA formation of GFP exclusively in mature OSNs is sufficient to induce neurodegeneration. Using unbiased RNA-seq and pathway analysis we showed that the expression of the transgene leads to the activation of the type I interferon innate immune signaling pathway, which is strongly activated by dsRNA, and overlaps with gene expression signatures in several cancer cell lines. Our results demonstrated that complex genomic rearrangements can lead to the production of cytoplasmic dsRNA that triggers type I interferon-signaling and neuronal apoptosis that propagates to neighboring, connected neurons as well as neurons in the same neural system, which ultimately leads to neural system failure and symptoms.

Experimental Procedures

The following materials and methods were used for Example 1.

Generation and characterization of Nd1 and Nd2 mice: The hAPPsw695 cDNA was amplified using primers with a PacI site flanking the 5' primer and an AscI and PacI site flanking the 3' end. For Nd1, the DNA fragment encoding ires-GFP was introduced into the AscI site and the hAPPsw-ires-GFP fragment introduced via a Pac site into pBSRV (Gogos, Osborne et al. 2000) which contained the TRE sequence followed by an artificial intron and splice site, and an SV40 polyadenylation signal. For Nd2, a DNA fragment encoding ires-mCherry was introduced into the Asc1 site and the hAPPsw-ires-mCherry fragment introduced via a Pac site into pBSRV. These transgenes were injected into the pronuclei of fertilized eggs (Nd1 at Columbia; Nd2 at MGH). Tail DNA from the resulting mice was isolated using standard procedures and analyzed for the transgene by Southern blotting and PCR. Founder mice with the transgene were crossed with OMP-ires-tTA mice (Yu, Power et al. 2004) to determine which founders had active transgenes. For Nd1, compound heterozygote mice of three founders each expressed hAPPsw and GFP in approximately 1% of OSNs and not elsewhere in the brain. For Nd2, compound heterozygote mice of two founders each expressed hAPPsw and mCherry in approximately 1% of OSNs (Nd2) and in approximately 15% of OSNs (CORMAC (Cao et al., Sci Rep. 2012; 2(231): 1-8) and not elsewhere in the brain. Founders were backcrossed into C57/BL6 for six generations to generate Nd1 and Nd2. A similar line COR-MAWG-E or Nd3 was generated using a similar genetic strategy described above by intgration of a transgene that expresses human wild type APP followed by an IRES followed by GFP. This line exhibits accelerated neurodegeneration and preliminary mapping of the transgene indicates that the integration of the transgene occurred in the context of chromothripsis.

BrdU labeling of OSNs: Mice were injected IP with 10 mg/kg body weight of BrdU (catalog #B23151, Life Technologies, Grand Island, N.Y.) diluted in 1×PBS. Mice were then sacrificed at 2 hours for analysis of neurogenesis or 15 and 30 days for the analysis of OSN lifespan. 20 μm thin coronal cryosections of the olfactory epithelium were cut on a micron 505H and placed onto super frost slides (catalog #12-550-17, Fisher Scientific, Pittsburgh, Pa.). The slides were allowed to dry for 30 minutes in a 37 degrees incubator before processing. Dried sections were fixed in freshly made 4% paraformaldehyde for 15 minutes, and then washed 3× with 1×PBS, and incubated in pre-warmed 2N HCl for 30 minutes at 37 degrees. The slides were then incubated in a 0.1M sodium Borate solution for 15 minutes. Slides were blocked with 5% horse serum, with 0.1% tritonX-100, in 1×PBS for 1 hour at room temperature. Afterwards a 1:100 dilution of mouse anti-BrdU in blocking buffer was applied each slide, which was covered with a Hybrislip cover (catalog #247459, Research Products International Corp., Mount Prospect, Ill.) and incubated overnight at 4 degrees. The next day the slides were washed 3× in 1×PBS and incubated with 1:500 Alexa488 conjugated anti-mouse secondary antibody (catalog #A-21202, Life Technologies, Grand Island, N.Y.) for 2 hours at room temperature. The slides were then washed 3× in 1×PBS and coverslipped with a solution of 90% glycerol, containing 4% n-propyl gallate in 1×PBS. BrdU positive cells were counted for the entirety of 3 sections (one anterior, one middle and one posterior in coronal sections) and was normalized over the area of the olfactory epithelia across these sections using the measuring tools in Adobe Photoshop.

MDA5 pulldown: We incubated a 1:100 dilution of rabbit anti-MDA5 antibody (catalog #5321, Cell Signaling, Beverly, Mass.) or equal concentration of Rabbit IgG (catalog #3900, Cell Signaling, Beverly, Mass.) with Protein A Dynabeads (Invitrogen) that were prepared according to the manufacturers protocol for 10-20 minutes at room temperature. Samples were pulverized on ice with a pestle in 1.5 ml microcentrifuge tubes with 1 ml of RIPA buffer (50 mM Tris pH 7.5, 150 mM NaCl, 1% Igepal, 0.5% sodium deoxycholate, 0.1% SDS), with 1× Halt protease inhibitor cocktail (catalog #78440 Thermoscientific, Pittsburgh, Pa.), and 2 mM of AMP-PNP, a non-hydrolyzable ATP analog to prevent dissociation of MDA5 oligomers from dsRNA (Sigma, catalog #A2657). Samples were then centrifuged for 2 minutes at 13,500 RPM at 4 degrees and was incubated with 25 μl of turbo DNase (Ambion, catalog #AM2238) for 1.5 hours in 37 degrees water bath. The supernatant was then split into two aliquots and transferred into tubes containing anti-MDA5 or IgG conjugated Dynabeads, and incubated overnight at 4 degrees on a orbital shaker. The next day we washed the beads 3× with RIPA buffer. Samples were eluted with 800 μl of Trizol reagent (catalog #15596-018, Life Technologies, Grand Island, N.Y.). The RNA was then used to generated cDNA libraries using the Super Script III First-strand Synthesis System (catalog #18080-051, Life Technologies, Grand Island, N.Y.).

RNA in situ hybridization: RNA in situ was performed as previously described (Cao et al., 2012). The templates for cRNA probes were generated by PCR amplification of cDNA libraries synthesized from olfactory epithelia of C57BL/6J mice (stock #000664, Jackson Laboratories, Bar Harbor, Me.), as described below. PCR products were cloned into TOPO pCRII vector (catalog #K4610, Life Technologies, Grand Island N.Y.). Each clone was verified by DNA sequencing (DNA Sequencing Core, Massachusetts General Hospital, Boston, Mass.). Digoxigenin labeled cRNA probes were synthesized as previously described (Cao et al., 2012) and a 1 μl aliquot was run on an 1% agarose gel for quality control.

| In situ probe primer sequences | | SEQ ID NO. |
|---|---|---|
| Ifi44 F | CTGAAAGAGGGCTTCCAGGG | |
| Ifi44 R | ATGCCTCCAGCTTGGACTTC | |
| OasI2 F | TGCCTGGGAGAGAATCGAGA | |
| OasI2 R | AGATGCAGATGTCGCGGTAG | |
| Stat1 F | AAGTCTGGCAGCTGAGTTCC | |
| Stat1 R | TACTTCCCAAAGGCGTGGTC | |
| APPinv F | ACTTCAGAGATCTCCTCCGTCT | |
| APPinv R | GGGAAGAGGCAGAACGTCAA | | cDNA libraries: Each olfactory epithelium was ground with an electric homogenizer in 1 ml of Trizol reagent (catalog #15596-018, Life Technologies, Grand Island, N.Y.). RNA was considered of good quality if there was an approximately 2:1 ratio of 28s relative to 18s ribosomal RNA bands on a 1% agarose gel, and a 260/280 spectrophotometer ratio of approximately 2. RNA was DNase treated using the DNA-free Kit (catalog #AM1906, Life Technologies, Grand Island N.Y.). 1 μg of purified DNase-free total RNA was used to generate oligodT primed cDNA libraries using the Super Script III First-strand Synthesis System (catalog #18080-051, Life Technologies, Grand Island, N.Y.) (see below for list of primers). cDNA libraries were cleaned up by ethanol precipitation as follows: samples were diluted to 100 μl with water and we added 200 μl of a solution consisting of 10% 3M sodium acetate, 95% ethanol, and 1 μl of 5 mg/ml Linear Acrylamide (catalog #AM9520, Life Technologies, Grand Island N.Y.). This mixture was placed at −20 degrees for 20 minutes or overnight. The next day the samples were pelleted in a microcentrifuge at 13,500 RPM for 15 minutes, washed 2× with 75% ethanol, air dried for 10 minutes, and resuspended in 100 μl of pure water. 1 μl of cDNA was used for each 25 μl qPCR reaction or for each 25 μl PCR amplification to synthesize RNA in situ probe templates.

| PCR Primers | | SEQ ID NO. |
|---|---|---|
| PKR-Fq | ATGCACGGAGTAGCCATTACG | |
| PKR-Rq | TGACAATCCACCTTGTTTTCGT | |
| hPKR-Fq | GCCGCTAAACTTGCATATCTTCA | |
| hPKR-Rq | TCACACGTAGTAGCAAAAGAACC | |
| RigI-Fq | AAGAGCCAGAGTGTCAGAATCT | |
| RigI-Rq | AGCTCCAGTTGGTAATTTCTTGG | |
| hRigI-Fq | CTGGACCCTACCTACATCCTG | |
| hRigI-Rq | GGCATCCAAAAGCCACGG | |
| MDA5-Fq | AGATCAACACCTGTGGTAACACC | |
| MDA5-Rq | CTCTAGGGCCTCCACGAACA | |
| hMDA5-Fq | TCGAATGGGTATTCCACAGACG | |
| hMDA5-Rq | GTGGCGACTGTCCTCTGAA | |
| C9orf72 sense | ACTGGTGGAATTGCCTGCAT | |
| C9orf72 antisense | AAGGAGACAGCTCGGGTACT | | qPCR: We used the iQ Sybr Green Supermix (catalog #170-8880, Bio-Rad, Hercules, Calif.) to perform qPCR in technical triplicates on an iCycler (Bio-Rad, Hercules, Calif.) with a tm=60 degrees. At least 2-4 biological replicates were performed. qPCR primers were designed using PrimerBank (REF), and were only used for analysis if they had an efficiency of at least 90%.

Immunofluorescence: 20 μm thick cryosections were cut from olfactory epithelia that were fixed and placed onto super frost slides (catalog #12-550-17, Fisher Scientific, Pittsburgh, Pa.). Sections were dried for 45 minutes at 37 degrees. Sections were then steamed for fixed with 4% paraformaldehyde (PFA) for 15 minutes. For sections from animals perfused with 4% PFA we treated the slides for 10 minutes in preheated 10 mM citrate buffer pH 6.0 in a food steamer (Oster, Fort Lauderdale, Fla.). Slides were then incubated for 1 hour with 300-500 μl of blocking buffer: 5% non-immune donkey serum, 0.1% triton-X100, in 1×PBS. After this blocking step the slides were dabbed on Kimwipes (catalog #06-666C, Fisher Scientific, Pittsburgh, Pa.) and we applied 125 μl of primary antibody diluted in blocking buffer and incubated in a humidified slide chamber overnight at 4 degrees. The next day the sections were washed 3 times in 1×PBS, then incubated for 2 hours with a 1:500 dilution of Cy3 conjugated donkey anti-mouse secondary antibody (catalog #706-165-148, Jackson Immunoresearch, West Grove, Pa.). In cases where amplification was necessary, we used the Cy3 Tyramide Signal Amplification kit (catalog #NEL744001KT, PerkinElmer, Waltham, Massachussetts).

| Primary antibody | Dilution |
| --- | --- |
| anti-hAPP 6E10 (catalog # SIG-39320, Covance, Princeton, NJ) | IF 1:100, W 1:1000 |
| anti-pStat1 (catalog # 9167, Cell Signaling, Beverly, MA) | IF 1:200, W 1:1000 |
| anti-cleaved Caspase-3 (catalog # 9661, Cell Signaling, Beverly, MA) | IF 1:250-1:500 |
| anti-MAVS (catalog # 3993, Cell Signaling, Beverly, MA) | W 1:1000 |
| anti-MDA5 (catalog # 5321, Cell Signaling, Beverly, MA) | IP 1:50 |
| Rabbit IgG (catalog # 3900, Cell Signaling, Beverly, MA) | Conc. of primary |
| anti-phospho-PKR (catalog # ab131447, Abcam, Cambridge, MA) | W 1:1000 |
| anti-PKR (catalog # sc-6282, Santa Cruz, Dallas, TX) | W 1:1000 |
| anti-APP 6900 ( catalog # 36-6900, Invitrogen) | IF: 1:500 |

OSN isolation: Freshly dissected olfactory epithelia were minced to ~1 mm³ cubes with a razor blade on a glass slide, and placed in a scintillation vial for dissociation. To isolate individual cells we used the Papain Dissociation System (catalog #LK003150, Worthington Biochemical Corporation, Lakewood, N.J.), with the following modifications: 1) we incubated olfactory epithelia in papain solution for only 15 minutes versus the recommended time without an appreciable loss of cells, 2) after trituration, the cell suspension was filtered through a 40 µm mesh strainer (catalog #352340, BD Bioscience, San Jose, Calif.). Dissociated cells were resuspended in 1 ml 1× Hank's balanced salt solution (HBSS) (catalog #14025, Life Technologies, Grand Island N.Y.) and directly sorted. Each olfactory epithelium was prepared and sorted in 1.5 hours. Samples were visually inspected under a microscope for purity.

Fluorescence activated cell sorting (FACS): GFP positive mature OSNs were purified from olfactory epithelia on a FACS Aria II SORPS cell sorter (BD Bioscience, San Jose, Calif.) with a 70 µm nozzle at a sheath pressure of 70 psi at 5000 events/second. The cells were identified by forward and side scatter and then gated for GFP positive signal relative to a non-GFP expressing control mouse line. The area of GFP positive cells was sorted into a 5 ml tube held in a 4 degree chilled chamber containing 500 µl of 1×HBSS. The sorted cells were pelleted at 2,500 rpm for 5 minutes at 4 degrees. The supernatant was discarded and the cells were resuspended in 800 µl of Trizol reagent (catalog #15596-018, Life Technologies, Grand Island, N.Y.), then frozen on dry ice and maintained at −80 degrees until processed for total RNA isolation. For a quantitative comparison of GFP positive cells in control versus transgenic animals, we compared the percent of GFP positive cells to the entire population of cells in the olfactory epithelium.

RNA-seq: RNA quality from FACS sorted cells was assessed by an RNA Pico chip on a 2100 Bioanalyzer (Agilent Technologies, Santa Clara, Calif.) by the Advanced Tissue Resource Center (ATRC, Harvard Neurodiscovery Center, Charlestown, Mass.). 150 ng of total RNA with a RIN value greater than 8.3 was used to generate sequencing libraries using the Illumina TruSeq mRNA Sample Preparation Kit (catalog #157894, Illumina, San Diego, Calif.), as per manufacturers protocol. Four samples, ligated with adapters AR002, AR004, AR006 and AR0012, were pooled and 50 bp single end reads were generated from an Illumina HiSeq 2000 by the Next Generation Sequencing Core (Massachusetts General Hospital, Boston, Mass.). Each sample contained no less than 40 million reads that were mapped to mouse genome mm9.

RNA-seq: Mapped reads were processed for expression analysis using the Cufflinks (REF) software pipeline via the Galaxy interface (cite three references). The gene list was analyzed for molecular pathway signatures using Ingenuity Pathway Analysis software (Qiagen, Redwood City, Calif.) and Gene Set Enrichment Analysis software (Broad Institute, Cambridge, Mass.).

Cell counts: A blinded comparison of the number of cleaved-caspase3 positive cells was done by counting every positive cell on every 10th section though the olfactory epithelium of control and transgenic mice performed in parallel.

AAV cranial injections: We instilled 2 µl of $10^{10}$ viral genome copies of either AAV9-GFP (catalog #AV-9-ALL854, UPENN Viral Vector Core, PA) or AAV9-FLEX-GFP (catalog #AV-9-PV1963, expressing anti-sense GFP, over the olfactory epithelium ~2 mm anterior of the olfactory bulb using a hamilton syringe. Animals were sacrificed 4 weeks after viral instillation for analysis. For quantitation of olfactory epithelium height 5× images were captured from alternating sections of the olfactory epithelium stained for OMP and anti-sense GFP via RNA in situ hybridization. On the OMP images we highlighted the boundaries of AAV infection defined by regions positive for anti-sense GFP. We then used a measurement tool in Photoshop to measure the apical-basal distance in pixels of the OMP layer, at approximately equal pixel distance throughout the anti-sense GFP positive layers. We avoided regions that were too lateral within the olfactory epithelium as they naturally undergo more frequent turnover and were likely to confound our data (Vedin, Molander et al. 2009).

Human brain Protein/RNA isolation: For protein isolation 200 mg of frozen brain tissue was pulverized in RIPA buffer (see above) on ice with a pestle in an microcentrifuge tube or glass tube. The sample was allowed to sit on ice for 3 minutes before centrifuging at 13,500 RPM for 5 minutes to pellet the cellular debris. The supernatant was transferred to a new tube the protein was quantitated using a BCA assay (catalog #PI-23227, Thermo Scientific, Pittsburgh, Pa.). 30 g of protein was loaded per well for western blots. For RNA isolation 200 mg of frozen brain tissue was ground with an electric homogenizer in 1 ml of Trizol reagent (catalog #15596-018, Life Technologies, Grand Island, N.Y.) and isolated according to manufactures protocol.

Example 1.1. The Nd1 and Nd2 Lines Exhibit Propagated Neurodegeneration in the Mouse Olfactory Neuronal Circuit Two independent transgenic mouse lines were produced at different times and in different facilities by oocyte microinjection with a bicistronic construct consisting of human cDNA containing exons 1-19 of the amyloid precursor protein (hAPP), an internal ribosome entry site (IRES), and a marker protein. The Neurodegenerative (Nd1) line expresses the Swedish isoform of hAPP (K670N, M671L), which causes a familial, early onset form of AD (Mullan, Crawford et al. 1992), and the fluorescent marker GFP (hAPPsw-IRES-GFP). Nd2 was engineered to express a synthetic allele of hAPP with an M to V amino acid substitution at position 671 (M671V), which is a much less avid substrate for BACE1 and reduces the production of the AP3 peptide by 90% from wild type levels (Citron, Teplow et al. 1995), and the fluorescent marker mCherry (hAPPmv-IRES-mCherry). The Nd1 line expresses wild type hAPP and the fluorescent marker GFP (hAPPsw-IRES-GFP). These constructs were placed downstream of a tetracycline responsive element (TRE), and we restricted expression of the transgenes to mature OSNs by crossing them into the OMP-IRES-tTA line (Gogos, Osborne et al. 2000), which was designed to express the tetracycline-controlled transcriptional activator protein from the native olfactory marker protein (OMP) locus (FIGS. 1A and 1B). This genetic approach allowed us to modulate transgene expression both in a cell type specific manner and temporally, in order to control for transgenic integration, and to evaluate the non-cell-autonomous effects of transgene expression.

We confirmed the expression of the transgenes using immunofluorescence with the 6E10 antibody specific for hAPP (FIGS. 1C and 1D). Less than 1% of OSNs express the transgene in a stochastic pattern. Manual counting of hAPP positive cells using DAPI as a counter stain confirmed that less than 1% of OSNs express the transgene at detectable levels. Quantification using fluorescence activated cell sorting (FACS) of GFP (Nd1) or Cherry (Nd2) positive cells relative to the total population confirmed this estimate (Nd1 0.83%±0.21% SEM, n=4, Nd2 0.73%±0.04% SEM, n=3).

Using the same genetic strategy, we previously reported that mouse lines simultaneously engineered to overexpress hAPPsw (CORMAP) or hAPPmv (CORMAC) in mature OSNs did not cause neuronal death (Cao, Schrank et al. 2012). Unexpectedly, an approximately 1.6 to 2-fold increase in immunofluorescent staining for cleaved-caspase 3 (CCASP3) in OSNs from Nd1 and Nd2 animals relative to littermate controls, respectively (Nd1, p=0.01, n=5; Nd2, p=0.003, n=5) (FIGS. 1E and 1G). We also observed an approximately 2-fold increase in TUNEL staining in the OE (data not shown). Quantification of the percentage of all mature OSNs in Nd1 and Nd2 animals by FACS reveals a striking 40% reduction in the steady state levels of OSNs after 90 days of age (Nd1 p<0.0001, n=4, Nd2 p=0.02, n=3) (FIG. 1F and 1H).

Figure 2C:
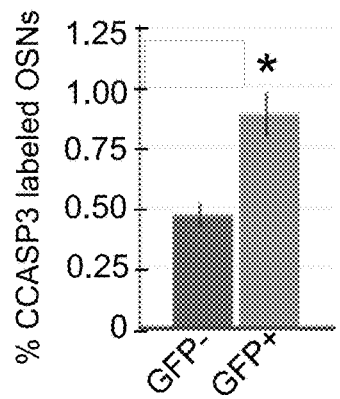

This 40% reduction of OSNs from the expression of the transgene in less than 1% of neurons reveals a robust non-cell-autonomous neurodegenerative phenotype. To examine this more closely we focused our attention on Nd1 since both Nd1 and Nd2 show similar phenotypes. Co-immunofluorescent labeling of GFP (transgene positive cells) and CCASP3 shows that most apoptotic OSNs in Nd1 do not express the transgene, even though there was a higher propensity for cell death in transgene positive cells (FIGS. 2A and 2C, p=0.02, approximately 1000 CCASP3 positive neurons for each of n=4 mice). Interestingly, we also found that the olfactory bulbs in Nd1 mice, which are the target of OSN axons and which do not express the transgene (FIG. 2D), are significantly smaller than control animals (FIG. 2E-2F), consistent with the propagation of neurodegeneration to neighboring and connected neurons in the mouse olfactory neural circuit.

Figures 7A, 7B:
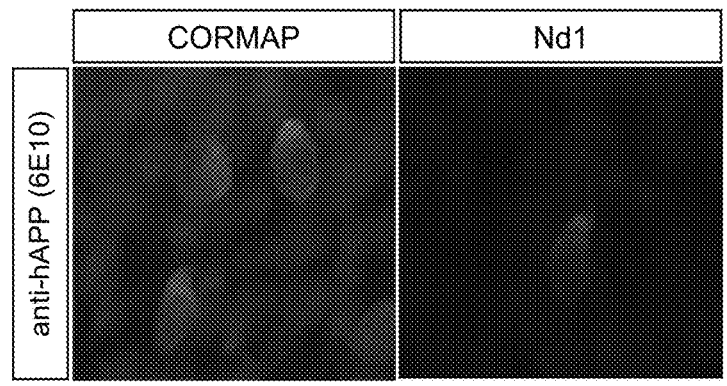
FIGS. 7A-E. hAPP protein expression is equivalent in CORMAP and Nd1. A,B) direct immunofluorescent staining of hAPP (6E10, red) in (A) CORMAP and (B) Nd1. C) Quantitation of the intensity of hAPP expression in CORMAP (blue bar) and Nd1 (green bar) in 100-300 cells across the olfactory epithelium for each of three animals (p=0.62). hAPP RNA expression is equivalent in CORMAC and Nd2. D) A schematic showing the isolation of transgene positive cells by FACS for qPCR analysis. E) qPCR with primers specific to hAPP on cDNA synthesized from RNA isolated from transgene positive cells in CORMAC and Nd2, in three technical replicates from two sets of animals (p=0.96).
Figure 7C:
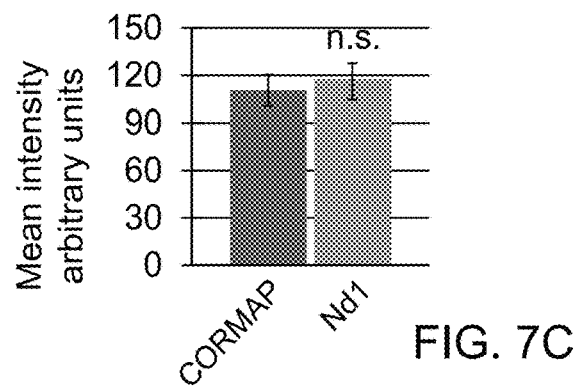
Figure 7D:
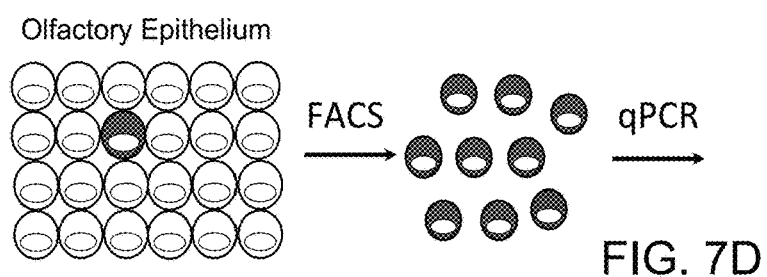
Figure 7E:
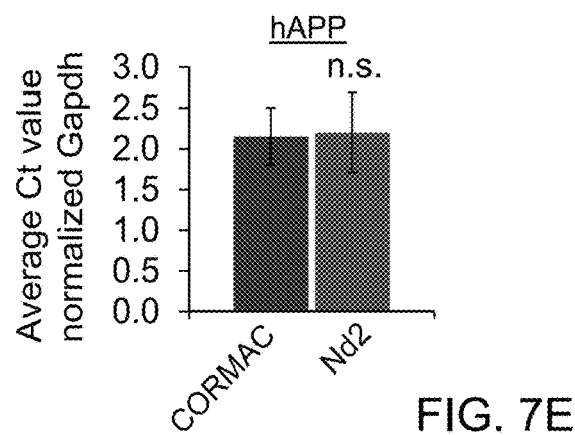
Figures 8A, 8B, 8C, 8E, 8F, 8G, 8I, 8J, 8K:
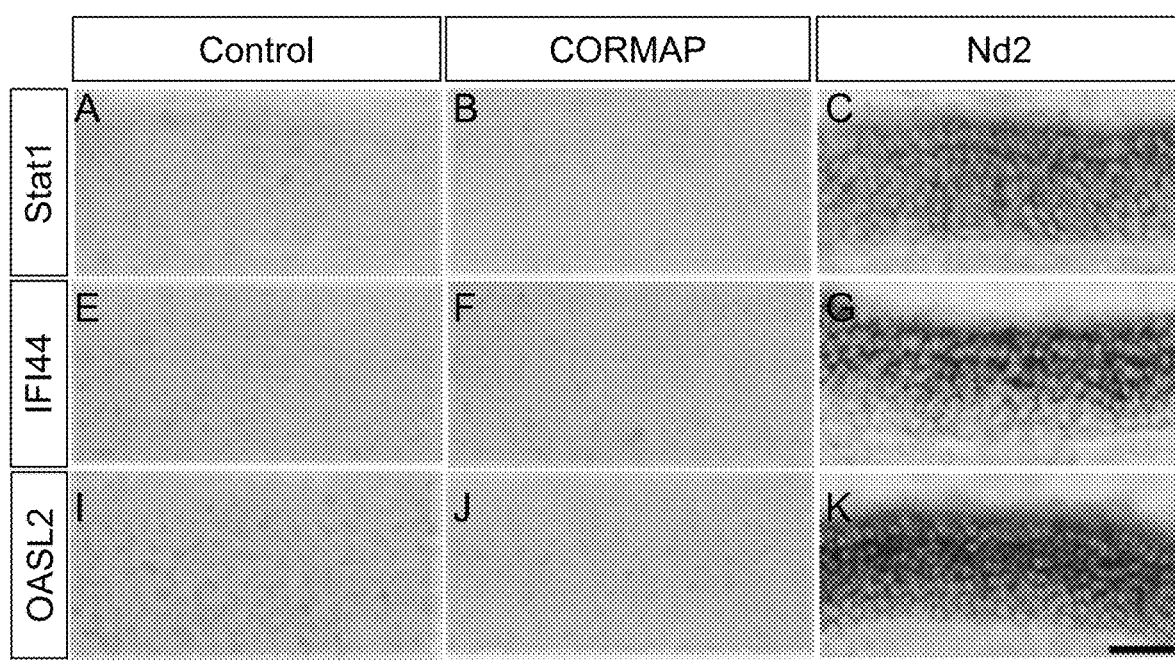
FIGS. 8A-8C, 8E-8G, 8I-8K. Type I interferon signaling is not unregulated in CORMAP, but is highly unregulated in Nd2 by RNA in situ hybridization. A-C) Stat1 expression in (A) control, (B) CORMAP, and (Nd2). E-G) IFI44 expression in (E) control, (F) CORMAP, and (G) Nd2. I-K) OASL2 expression in (I) control, (J) CORMAP, and (K) Nd2.

Example 1.2. Neurodegeneration Associated with Genomic Lesions and not hAPP Expression Levels One possibility for the discrepancy in the neurodegeneration in Nd1 versus CORMAP, which both express hAPPsw, and between Nd2 versus CORMAC, which both express hAPPmv, could be expression levels of APP. However, there was no statistical difference in the quantitation of hAPP protein expression levels in Nd1 compared to CORMAP by direct immunofluorescence using an antibody specific for hAPP (6E10) (FIG. 7A-7C) (or anti-APP antibody 6900, data not shown). This is consistent with our observation that in the Tg2576 mouse model of Alzheimer's disease (Hsiao, Science 274(5284):99-102 (1996)), which expresses higher levels of hAPPsw and produces more AP3 peptide in the olfactory epithelium, there is no OSN death (Cao et al. Nature Comm., 2012) Moreover, there is no statistical difference in the levels of hAPP RNA expression detected by quantitative PCR (qPCR) of FACS isolated transgene positive OSNs from Nd2 and CORMAC (FIGS. 7D and 7F, p=0.96). Therefore, the loss of neurons in Nd1 and Nd2 is not accounted for by hAPP expression levels, suggesting an alternate mechanism for neurodegeneration.

Another possibility is that transgenic integration disrupted native genes, however, we did not observe increased apoptosis or loss of mature OSNs in animals containing Nd1 or Nd2 transgenes alone (TRE-hAPPsw-IRES-GFP and TRE-hAPPmv-IRES-mCherry). Furthermore, silencing of transgene expression in adult Nd1 mice by the oral administration of doxycycline via food for three months was sufficient to rescue neuronal apoptosis to levels observed in control animals (p=0.25, n=3) (FIG. 1E). Lastly, mapping of our transgenes localized them to unique chromosomal (Chr) loci (FIG. 3B): Nd1 to Chr 15 and CORMAP to Chr 9. Importantly, these data show that transgene expression is both necessary and sufficient for neurodegeneration in Nd1 and Nd2, and appears to be independent of transgene position effects and hAPP levels.

Example 1.3. Cytoplasmic Double Stranded RNA Evokes Type I Interferon Signaling and Neurodegeneration Recent studies showed that the transgenic constructs in the R6/1 and R6/2 Huntington's disease (HD) mouse models, as well as transgenic sheep constructs, underwent complex genetic rearrangements called chromothripsis upon integration, which included deletions, insertions, and inversions of the transgenic sequence that may explain phenotypic differences in these HD transgenic mouse models (Chiang et al, Nature Gen. 44:390-7, S1, 2012). Transgenic chromothripsis mirrors chromothripsis in human genomes; the latter is enriched in autism and related neurodevelopmental disorders, suggesting that it alters neuronal function. We posited that chromothripsis occurred in Nd1 and Nd2 transgenes leading to a toxic gain of function. To test this model we performed deep-sequencing on whole genome jumping libraries with insert sizes selected at ~2kb (Hanscom and Talkowski 2014). Sanger sequencing confirmed that Nd1 integrated into Chr 15 and CORMAP into Chr 9 (FIGS. 3A and 3B). However, we found that Nd1 underwent chromothripsis, which involved more than 2 breakpoints consisting of deletions, insertions, and at least one inversion during integration (FIG. 3B). Our data suggested that Nd2, but not CORMAC (generated at the same time from the same expression construct) also underwent chromothripsis, as well as Nd3.

We were intrigued by the possibility that the inverted sequence might lead to the formation of dsRNA, which triggers an innate immune response and can lead to programmed cell death. Consistent with this model we found that dsRNA was aberrantly expressed in the cytoplasm in Nd1, but not CORMAP, using immunofluorescent staining with the J2 antibody that specifically recognizes dsRNA (FIGS. 3C and 3D). Moreover, we detected the expression of both sense and anti-sense RNA for hAPP (from the inverted fragment) by RNA in situ hybridization in the cytoplasm of Nd1 (FIG. 3E-3J). We note that there were fewer cells expressing anti-sense relative to sense RNA for both GFP and APP, which may be due to rapid loss of neurons expressing dsRNA above a threshold, RNA editing (Savva, Rieder et al. 2012) and/or the competitive interactions of endogenous dsRNA with RNA probe. This observation was consistent with a recent study that observed fewer cells expressing antisense C9orf72 relative to sense C9orf72 transcripts in the brains of ALS patients using LNA in situ probes (Mizielinska, Lashley et al. 2013).

Together these data provide strong evidence that genomic lesions can lead to toxicity via cytoplasmic dsRNA. To directly test if dsRNA is sufficient to induce neurodegeneration we developed a strategy to express both sense and antisense GFP in mature OSNs. We accomplished this by infecting OMP-IRES-GFP mice (Shykind, Rohani et al. 2004), which express sense GFP exclusively in mature OSNs, with an AAV9-flex-GFP virus (Cardin, Carlen et al. 2009), which expresses antisense GFP in the absence of Cre protein (FIG. 4). We injected littermate control mice (GFP positive) with AAV9-GFP at the same viral titer, or mice that express tTA from the OMP locus (control for exogenous protein expression) infected with the AAV9-flex-GFP virus as controls. One month after viral infection, the animals were sacrificed and sections were labeled by J2 immunofluorescence to show the presence of dsRNA (FIGS. 4B and 4C) and by RNA in situ hybridization for antisense GFP, showing that we were successful at infecting OSNs with AAV encoding anti-sense GFP (FIGS. 4D and 4E). We quantitated the height of the mature OSN layer (a measure of OSN degeneration), which was labeled by RNA in situ hybridization with a probe against OMP, labeling all mature OSNs, and showed that there was an approximately 30% reduction in the OSNs in animals with dsRNA vs controls (P<0.0001) (FIG. 4F-4H). These data were consistent with data showing that intranasal instillation with polyinosinic-polycytidylic acid (Poly (I:C)), a synthetic dsRNA, causes degeneration of OSNs in mice and cortical neurons in rats (Melton, Keith et al. 2003, Kanaya, Kondo et al. 2014).

Figures 5A, 5P:
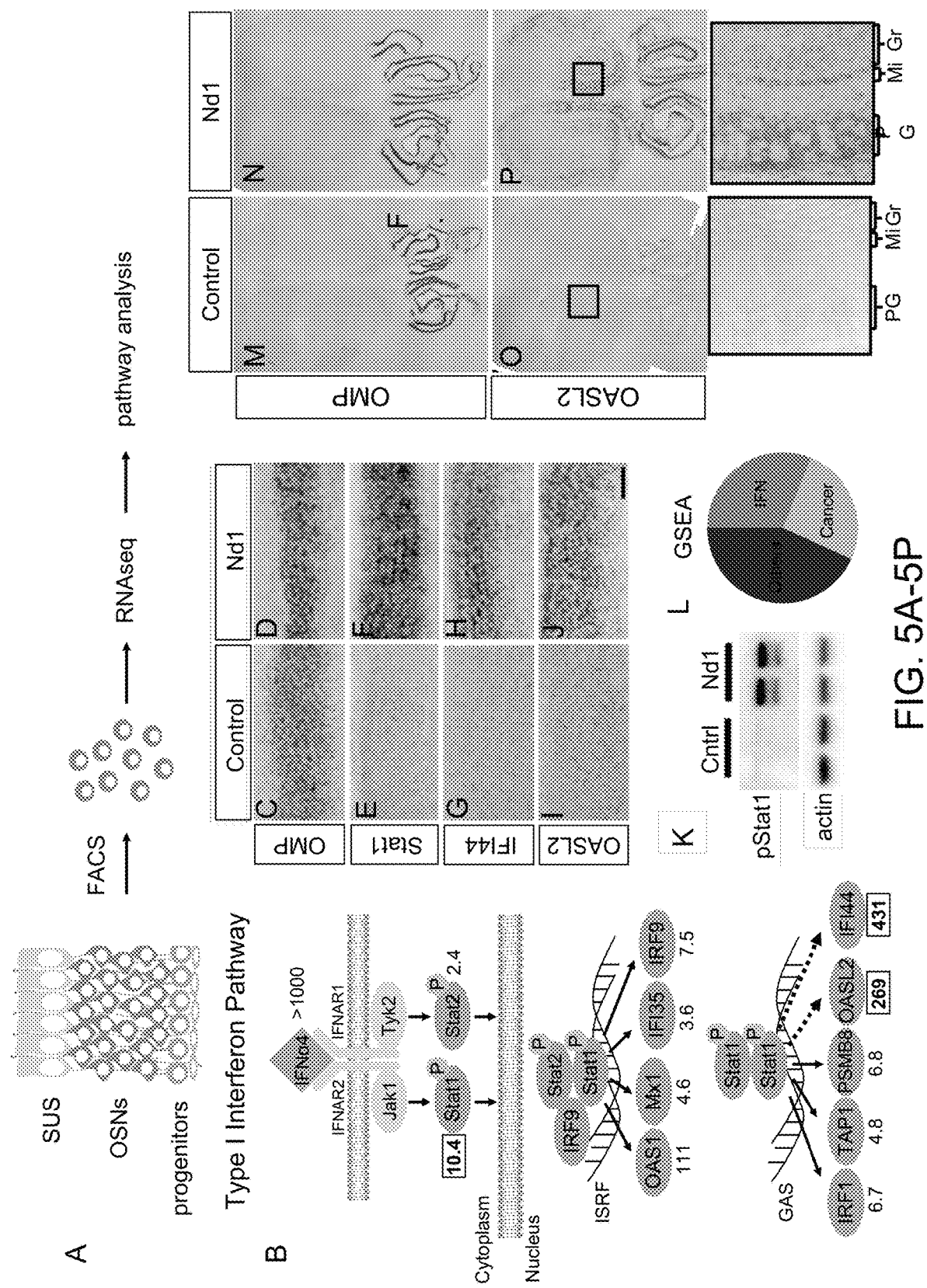
FIGS. 5A-P. Type I interferon signaling is highly unregulated, both cell-autonomously and non-cell-autonomously, in Nd1 relative to littermate controls. A) A schematic of the experiment paradigm: OSNs expressing GFP were isolated by FACS, subsequent RNA-seq and pathway analysis were performed on these samples. B) A schematic modified from Ingenuity Pathway Analysis, showing the upregulation type I interferon signaling pathway in Nd1 by RNA-seq. Genes labeled with numbers were upregulated by indicated fold values. Genes with boxed fold values were used to confirm the RNA-seq by RNA in situ hybridization (C-J) or western blotting (K). C, D) OMP was used as a positive control to label mature OSNs. The expression of Stat1 (E, F), IFI44 (G, H), and OASL2 (I, J) are all unregulated in Nd1 relative to controls by RNA in situ hybridization. K) Western blot showing elevated phosphorylated Stat1 in Nd1 relative to controls. L) Pie chart showing an enrichment of type I interferon/viral signaling and cancer cell line gene expression signatures with the gene expression signature of Nd1. M-P) RNA in situ showing that OASL2, as a marker of IFN signaling, is expressed in both the olfactory epithelium, and all cells of the olfactory bulb (O, P, and insets). Pg=periglomerular, Mi=mitral cells, Gr=granule neurons.

To identify molecular changes that may shed light onto the mechanism of genomic lesion induced neurodegeneration we compared the transcriptomes of purified mature OSNs from Nd1 and littermate control mice by RNA-seq. We confirmed our results in both Nd1 and Nd2, which phenocopy each other. We adopted this strategy to avoid spurious gene expression changes due to changes in cell types due to apoptosis of OSNs. We crossed Nd1 with a mouse line where all mature OSNs were labeled with GFP (OMP-IRES-GFP) and used FACS to purify mature OSNs from Nd1 (FIG. 5A). Using Ingenuity Pathway Analysis software (IPA) to analyze our single end RNA-seq results we found that the innate immune type I interferon (IFN) signaling pathway is the most highly upregulated pathway in Nd1 relative to controls among genes elevated 2-fold or higher (FIG. 5B, p=$6.2 \times 10^{-6}$). Type I IFN signaling is potently activated by cytoplasmic dsRNA, consistent with our data that dsRNA is triggering an innate immune response in OSNs in our transgenic mice with neurodegeneration. We confirmed the increased expression of the three highly upregulated type I IFN induced genes, signal-transducing activators of transcription 1 (Stat1), 2'-5' oligoadenylate synthetase-like 2 (Oasl2), and interferon induced protein 44 (Ifi44), by RNA in situ hybridization (FIG. 5C-5J), as well as protein kinase R (PKR), and melanoma differentiation-associated protein 5 (MDA5) by qPCR (FIG. 6B). We verified that Stat1, Oasl2, and Ifi44 were also highly expressed in OSNs of Nd2 mice, but not CORMAP mice, which overexpresses hAPPsw in mature OSNs using a similar genetic strategy but does not exhibit neurodegeneration (FIG. 8A-8K). In addition to looking at gene expression levels we tested for the activation of type I interferon signaling at a protein level. Ligation of the type I Interferon receptor triggers the phosphorylation of STAT 1, which subsequently localizes to the nucleus where it regulates gene transcription, thereby serving as a node for downstream effectors of interferon signaling (FIG. 5B). We performed western blotting of olfactory epithelium extracts from Nd1 and littermate controls and observed a dramatic increase phosphorylated-STAT1 (pSTAT1) relative to actin (FIG. 5K).

Figure 2D:
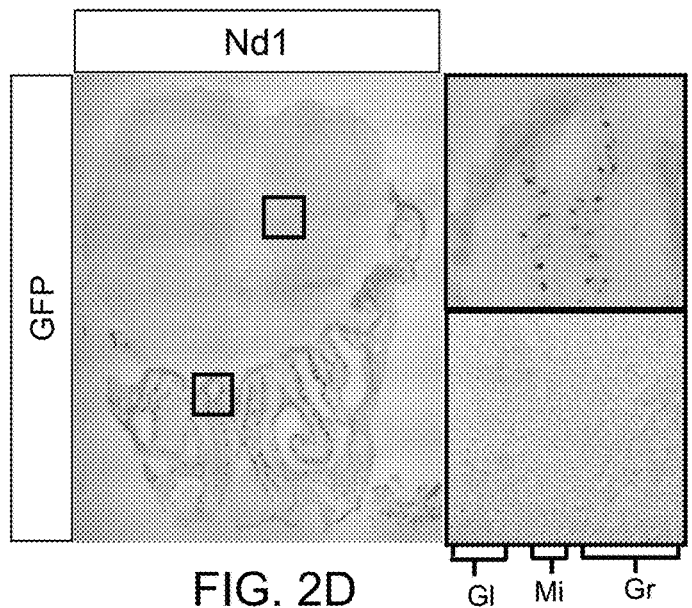
Figure 2E:
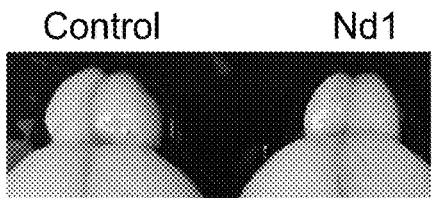
Figure 2F:
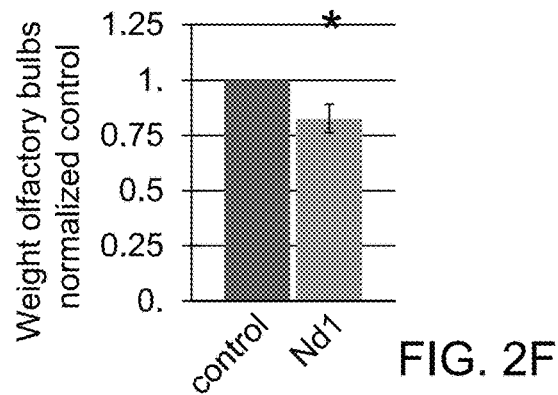

Interestingly, Stat1, Oasl2, and Ifi44 were highly expressed non-cell-autonomously (i.e. in both transgene negative and positive OSNs) (compare FIG. 3F with 5F, 5H, and 5J). Moreover, using Oasl2 as a marker of this IFN signaling pathway, we showed that this signaling cascade propagated to multiple cell types of the olfactory bulb including (FIG. 5I-5O): 1) the periglomerular layer (Pg) containing interneurons surrounding OSNs axon termini, 2) the mitral cells (Mi) that are the postsynaptic partner of OSNs, and 3) the granule neurons (Gr), which are interneurons that lie deep within the olfactory bulb. We confirmed the propagation of IFN signaling to these cell types in the bulb with both Stat1 and IFI44 and that the transgene was not expressed in these cell types (FIG. 2D). Together these data show that type I interferon signaling is propagated non-cell-autonomously, and correlates with neurodegeneration across our transgenic mouse lines.

Example 1.4. Pattern Recognition Receptors Recognizing dsRNA are Induced and Engaged in Nd1 Mice MDA5 and PKR are two prominent cytosolic pattern recognition receptors that can recognize and bind endogenous cytoplasmic dsRNAs (Nallagatla, Toroney et al. 2011, Wu, Peisley et al. 2013). Activation of these receptors by dsRNA leads to a positive feedback loop that enhances their own gene expression (Takeuchi and Akira 2010). We found that PKR and MDA5 are protein levels were elevated in Nd1 relative to littermate controls in our RNA-seq data (FIG. 6A). We confirmed these results by qPCR and western blotting (FIGS. 6B, 6D, and 6E). MDA5 is activated by forming oligomers templated by dsRNA molecules >34 nucleotides in length (Peisley, Lin et al. 2011). Aggregated MDA5 directly interacts with the mitochondrial anti-viral signaling proteins (MAVS), triggering the aggregation and degradation of the large isoform of MAVS, but not miniMAVS, a smaller isoform of MAVS which serves as an internal control (Castanier, Zemirli et al. 2012, Wu, Peisley et al. 2013, Brubaker, Gauthier et al. 2014). Consistent with an activation of MDA5, western blotting of olfactory epithelium extracts with an antibody against MAVS showed a dramatic reduction in the large isoform of MAVS relative to miniMAVS in Nd1 relative to control mice (FIG. 6D). The activation of PKR by dsRNA activated p38 MAPK and the phosphorylation of eukaryotic translation initiation factor 2A (pEIF2a). Even though there was an increase in total PKR protein levels, the levels of pEIF2a were not changed in Nd1 relative to controls by whole olfactory epithelium western blotting (FIG. 6E). However, the phosphorylation of the well-established p38 substrate heat shock protein 27 (HSP27) (Cargnello and Roux 2011) was increased in Nd1 relative to controls suggesting that p38 signaling, which is PKR dependent in the setting of dsRNA (Goh, deVeer et al. 2000, Ishibashi, Ali et al. 2011), is active in Nd1 (FIG. 6E).

To directly test if MDA5 binds to dsRNA derived from Nd1 we performed RNA co-immunoprecipitation experiments with an antibody raised against MDA5 or IgG on aliquots from the same olfactory epithelial extracts (FIG. 6F). Using PCR we were able to enrich for a fragment of hAPP with MDA5, which we found to be inverted in Nd1, but not with an IgG antibody at the same concentration (n=3), and not with primers outside of the hAPP inversion.

References for Examples 1

Brubaker, S. W., A. E. Gauthier, E. W. Mills, N. T. Ingolia and J. C. Kagan (2014). "A Bicistronic MAVS Transcript Highlights a Class of Truncated Variants in Antiviral Immunity." *Cell* 156(4): 800-811.

Cao, L., B. R. Schrank, S. Rodriguez, E. G. Benz, T. W. Moulia, G. T. Rickenbacher, A. C. Gomez, Y. Levites, S. R. Edwards, T. E. Golde, B. T. Hyman, G. Barnea and M. W. Albers (2012). "Abeta alters the connectivity of olfactory neurons in the absence of amyloid plaques in vivo." *Nat Commun* 3: 1009.

Cardin, J. A., M. Carlen, K. Meletis, U. Knoblich, F. Zhang, K. Deisseroth, L. H. Tsai and C. I. Moore (2009). "Driving fast-spiking cells induces gamma rhythm and controls sensory responses." *Nature* 459(7247): 663-667.

Cargnello, M. and P. P. Roux (2011). "Activation and function of the MAPKs and their substrates, the MAPK-activated protein kinases." *Microbiol Mol Biol Rev* 75(1): 50-83.

Castanier, C., N. Zemirli, A. Portier, D. Garcin, N. Bidere, A. Vazquez and D. Arnoult (2012). "MAVS ubiquitination by the E3 ligase TRIM25 and degradation by the proteasome is involved in type I interferon production after activation of the antiviral RIG-I-like receptors." *BMC Biol* 10: 44.

Citron, M., D. B. Teplow and D. J. Selkoe (1995). "Generation of amyloid beta protein from its precursor is sequence specific." *Neuron* 14(3): 661-670.

Gogos, J. A., J. Osborne, A. Nemes, M. Mendelsohn and R. Axel (2000). "Genetic ablation and restoration of the olfactory topographic map." *Cell* 103(4): 609-620.

Goh, K. C., M. J. deVeer and B. R. Williams (2000). "The protein kinase PKR is required for p38 MAPK activation and the innate immune response to bacterial endotoxin." *EMBO J* 19(16): 4292-4297.

Hanscom, C. and M. Talkowski (2014). "Design of large-insert jumping libraries for structural variant detection using illumina sequencing." *Curr Protoc Hum Genet* 80: 7 22 21-29.

Ishibashi, O., M. M. Ali, S. S. Luo, T. Ohba, H. Katabuchi, T. Takeshita and T. Takizawa (2011). "Short RNA duplexes elicit RIG-I-mediated apoptosis in a cell type- and length-dependent manner." *Sci Signal* 4(198): ra74.

Kanaya, K., K. Kondo, K. Suzukawa, T. Sakamoto, S. Kikuta, K. Okada and T. Yamasoba (2014). "Innate immune responses and neuroepithelial degeneration and regeneration in the mouse olfactory mucosa induced by intranasal administration of Poly(I:C)." *Cell Tissue Res* 357(1): 279-299.

Melton, L. M., A. B. Keith, S. Davis, A. E. Oakley, J. A. Edwardson and C. M. Morris (2003). "Chronic glial activation, neurodegeneration, and APP immunoreactive deposits following acute administration of double-stranded RNA." *Glia* 44(1): 1-12.

Mizielinska, S., T. Lashley, F. E. Norona, E. L. Clayton, C. E. Ridler, P. Fratta and A. M. Isaacs (2013). "C9orf72 frontotemporal lobar degeneration is characterised by frequent neuronal sense and antisense RNA foci." *Acta Neuropathol* 126(6): 845-857.

Mullan, M., F. Crawford, K. Axelman, H. Houlden, L. Lilius, B. Winblad and L. Lannfelt (1992). "A pathogenic mutation for probable Alzheimer's disease in the APP gene at the N-terminus of beta-amyloid." *Nat Genet* 1(5): 345-347.

Nallagatla, S. R., R. Toroney and P. C. Bevilacqua (2011). "Regulation of innate immunity through RNA structure and the protein kinase PKR." *Curr Opin Struct Biol* 21(1): 119-127.

Peisley, A., C. Lin, B. Wu, M. Orme-Johnson, M. Liu, T. Walz and S. Hur (2011). "Cooperative assembly and dynamic disassembly of MDA5 filaments for viral dsRNA recognition." *Proc Natl Acad Sci USA* 108(52): 21010-21015.

Savva, Y. A., L. E. Rieder and R. A. Reenan (2012). "The ADAR protein family." *Genome Biol* 13(12): 252.

Shykind, B. M., S. C. Rohani, S. O'Donnell, A. Nemes, M. Mendelsohn, Y. Sun, R. Axel and G. Barnea (2004). "Gene switching and the stability of odorant receptor gene choice." *Cell* 117(6): 801-815.

Takeuchi, O. and S. Akira (2010). "Pattern recognition receptors and inflammation." *Cell* 140(6): 805-820.

Vedin, V., M. Molander, S. Bohm and A. Berghard (2009). "Regional differences in olfactory epithelial homeostasis in the adult mouse." *J Comp Neurol* 513(4): 375-384.

Wu, B., A. Peisley, C. Richards, H. Yao, X. Zeng, C. Lin, F. Chu, T. Walz and S. Hur (2013). "Structural basis for dsRNA recognition, filament formation, and antiviral signal activation by MDA5." *Cell* 152(1-2): 276-289.

Yu, C. R., J. Power, G. Barnea, S. O'Donnell, H. E. Brown, J. Osborne, R. Axel and J. A. Gogos (2004). "Spontaneous neural activity is required for the establishment and maintenance of the olfactory sensory map." *Neuron* 42(4): 553-566.

Example 2. Cytoplasmic Double Stranded RNA, Present in Neurons of ALS and Alzheimer's Disease Patients, Triggers Neurodegeneration Neurodegenerative diseases are a growing scourge without effective therapies. While each disease has distinguishing clinical and pathological features, common mechanisms may participate in the initiation and/or propagation of these diseases through neural systems. For instance, mounting evidence implicates a role for the innate immune system and for TDP-43 cytoplasmic inclusions in amyotrophic lateral sclerosis (ALS) (1) and Alzheimer's disease (AD) (2) among others, but the triggers of these pathological hallmarks remain elusive. In contrast, viral encephalitides have a clear trigger that in many cases result in progressive neurodegeneration in the setting of a fulminant immune response to double stranded (dsRNA). Recent observations by multiple laboratories (3, 4), and confirmed in our own laboratory, indicate that both sense and antisense RNA strands are produced from the most common genetic lesion associated with ALS, the hexanucleotide repeat of C9orf72. We hypothesized that sense and anti-sense strands could form an intermolecular cytoplasmic dsRNA, which would serve as a viral mimetic, thereby evoking an innate immune response leading to neurodegeneration.

Figures 10A, 10B, 10C, 10D, 10E, 10F:
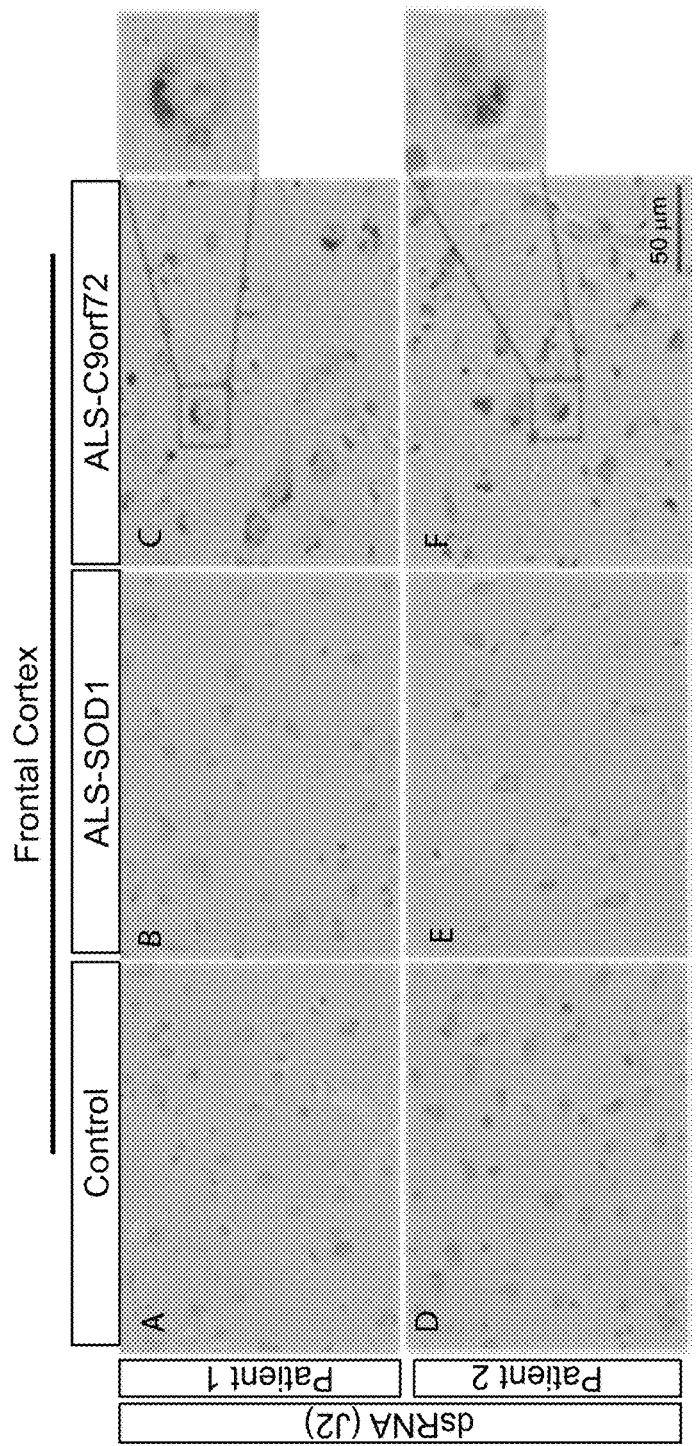
FIGS. 10A-H. Neurons in ALS-C9orf72 cases contain high levels of dsRNA in the frontal cortex. A-F) Representative images of immunocytochemistry on sections from the superior frontal cortex (B8,9) with the J2 antibody that recognizes dsRNA. DsRNA positive staining in brown (DAB) can be regularly seen in ALS-C9orf72 (A,D), but not regularly in ALS-SOD (B,E), or control sections (C,F). Insets of digitally magnified cells show the granularity of dsRNA staining in ALS-C9orf72. G) Quantification of the percentage of cells (nuclear counter stain in blue) that are dsRNA positive as recorded using Fiji in ALS-C9orf72 (n=3) compared to control brains (n=3, p<0.00001), and ALS-SOD brains compared to controls (n=3, p=0.24). H) Quantification of the proteins level of PKR, a double-stranded RNA binding protein, shows it is more highly expressed in ALS-C9orf72 relative to controls (p<0.05).

To test this hypothesis, we immunostained cerebellum (FIG. 9) and frontal cortices (FIG. 10) from patients diagnosed with ALS in the setting of a hexanucleotide expansion (GGGGCC) of C9orf72 using an antibody that recognizes dsRNA in a sequence-independent fashion (FIG. 11). We found a highly significant enrichment of signal in the cytoplasms of neurons and smaller cells in these ALS cases relative to age-matched controls and ALS-SOD1 (FIGS. 10A-H). The signal was largely abrogated by immunostaining with a isotype primary antibody control (FIG. 9) and by preincubating the antibody with poly-inosinic-polycytidylic acid (poly IC), a synthetic dsRNA-mimetic (FIG. 11). The morphology of this specific cytoplasmic staining was typically perinuclear and consistent with granules. DsRNA cytoplasmic inclusions were also found in neurons in the dentate nuclei in the cerebellum of these ALS cases (FIG. 9A-D), but were not prevalent in Purkinje cells (FIG. 9). The specific immunostaining did not overlap with lipofuscin. In ALS cases with SOD1 mutations, which do not have TDP-43 pathology, dsRNA cytoplasmic inclusions were not detected (FIG. 10B, E).

Figure 10H:
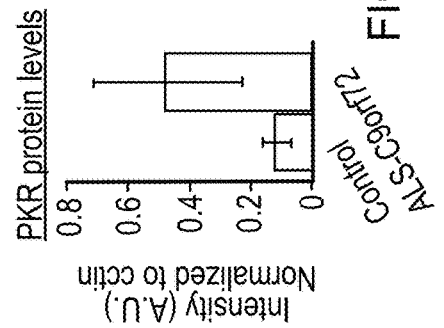
Figure 10G:
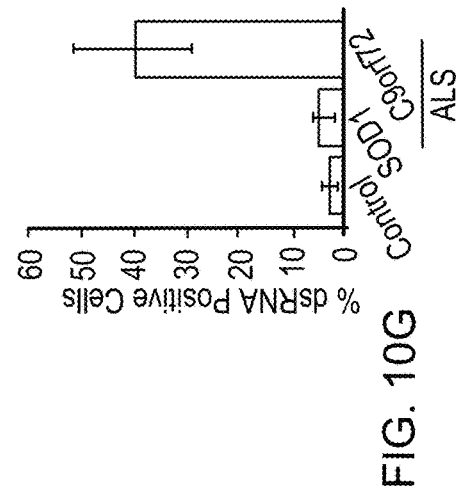

Cytoplasmic dsRNA is sensed by three different proteins, PKR, MDA5, and RIG-I, that are components of the innate immune system. Engagement of each protein by dsRNA induces interferon signaling and neurodegeneration. We found significantly increased levels of PKR protein in the frontal lobes of ALS patients with expanded C9orf72 alleles relative to frontal lobes from control cases (FIG. 10H). To determine if cytoplasmic dsRNA was sufficient to mediate neurodegeneration in a human neurons, we transfected neuronal differentiated ReNcell VM cells, a human neural cell line derived from ventral mesencephalon, with escalating doses of poly IC (which mimics a GC dinucleotide repeat). After 2 days in culture, we found a dose-dependent reduction in their viability (FIGS. 12A-G) relative to mock-transfected neurons. We observed massive induction of MDA5 and PKR (FIG. 12G) as well as downstream activators in their respective pathways, (MAVS reduction, and phosphorylation of p38), indicating that neurons are capable of mounting this innate immune response intrinsically and that cytoplasmic dsRNA is sufficient to induce neuronal death.

Next, we sought to determine whether intermolecular, cytoplasmic dsRNA is sufficient to induce neuronal death in vivo. Mice with the olfactory marker protein gene locus targeted to express GFP exclusively in mature olfactory sensory neurons (OSNs) were intranasally infected with an AAV that expressed inverted GFP driven by a constitutively active promotor. Two weeks after infection we observed a 40% reduction in the olfactory epithelial thickness in regions of the olfactory epithelium where infection occurred (FIG. 4A). The degree of neuronal loss was significantly less in wild type mice infected with the AAV expressing Flex-GFP as well as wild type mice infected with an viral isotype-matched AAV that expresses GFP to facilitate observation of the infected regions (FIG. 4F-G). We determined that cytoplasmic dsRNA was following infection of the AAV expressing inverted GFP in the mice expressing GFP using immunostaining, but not present in similarly infected wild type mice (FIG. 4B-C). Together, these results demonstrated that formation of an intermolecular dsRNA in the cytoplasm, which does not encode toxic substances, is sufficient to mediate neuronal loss in vivo.

Figure 13A:
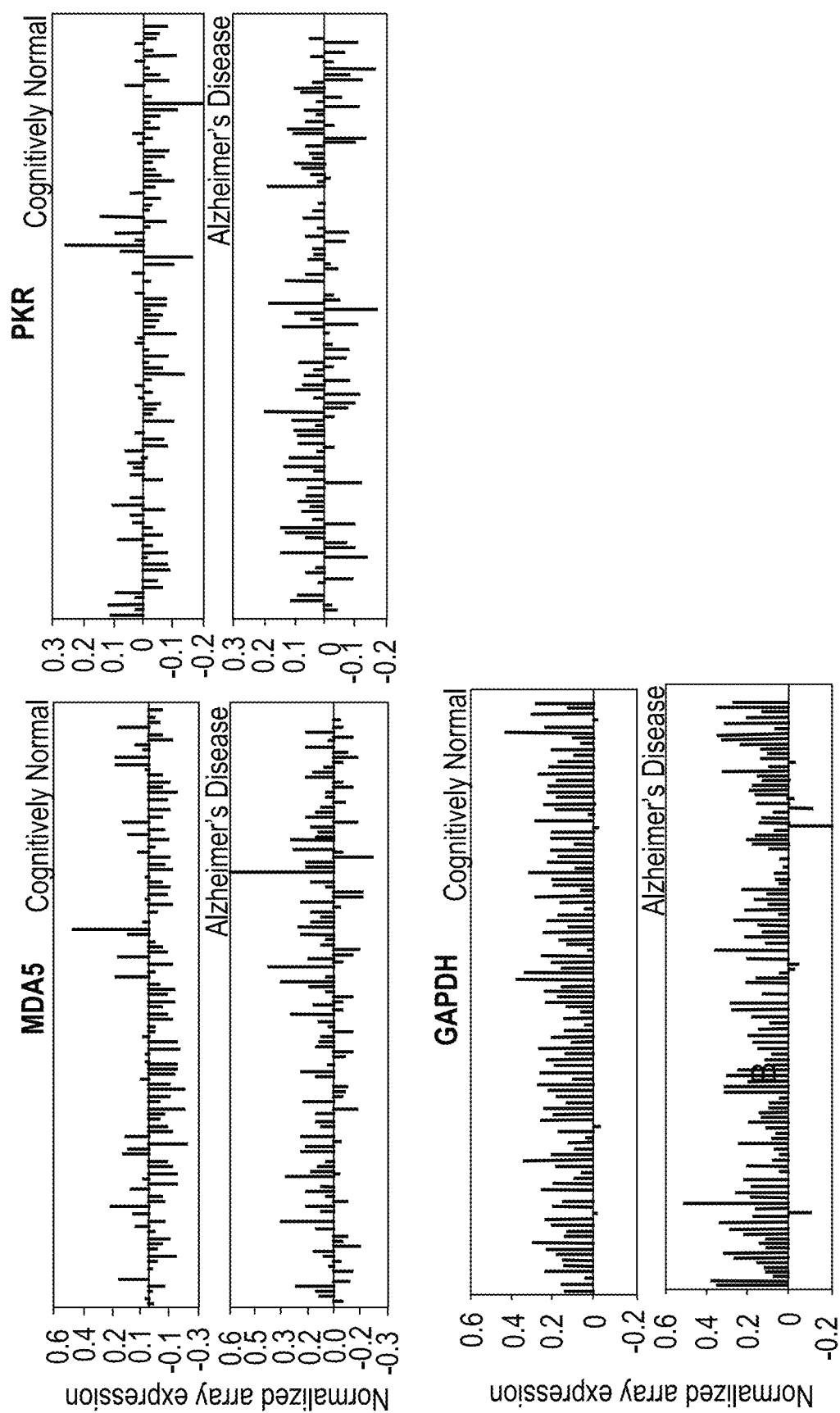
FIGS. 13A-D. The cytoplasmic dsRNA binding receptors PKR and MDA5 are more highly expressed in AD brains and dsRNA is present in the frontal cortex of AD brains. A) Graphs made from publicly available microarray RNA expression data frontal cortex of AD and control brains. B) J2 immunohistochemistry detects higher levels of dsRNA in AD brains (B, brown DAB stain) than controls (C), quantified in (D), n=4 AD and n=3 controls, p=0.026).

Cytoplasmic dsRNA ignites an innate immune cascade that results in interferon production and induction of a family of interferon stimulated genes (ISGs). Subsets of these ISGs have been reported to be significantly increased in ALS and Alzheimer's disease (AD). For instance, the dsRNA-activated protein kinase PKR is present at 26-fold greater levels in the cerebrospinal fluid (CSF) of ALS patients (6), and elevated PKR has been reported in the CSF of AD patients (7), and was associated with a decline in a neuropsychological test performance over the following 2 years (8). We examined expression profiles of brains with AD and age-matched cognitively normal individuals (9). Analysis of 129 frontal lobes from brains with AD clinical diagnosis and 101 age-matched cognitively normal people showed a significant increase in the levels of mRNA present in the both PKR (FIG. 13A) and MDA5 (FIG. 13B) in the AD brains. However, a subset of the cognitively normal individuals also manifested high levels of PKR and/or MDA5, which may represent the early stages of a neurodegenerative process (but might also indicate an active viral process at death). In a second analysis, we examined the levels of MDA5 and PKR protein in 19 different regions of brains from aged individuals that span the spectrum of Alzheimer's disease (from cognitively normal to severe dementia). After establishing norms for expression levels of both proteins in the cognitively normal individuals, we found that 10 patients with MCI or AD dementia (FIG. 13C) had at least one brain region with levels of both MDA5 and PKR 2 standard deviations above the mean, (p<0.01). Moreover, all these brain regions mapped to regions involved in the cortical signature of AD (10), based on a comprehensive analysis of atrophy in high-resolution MRIs of patients with AD.

Figures 13B, 13C:
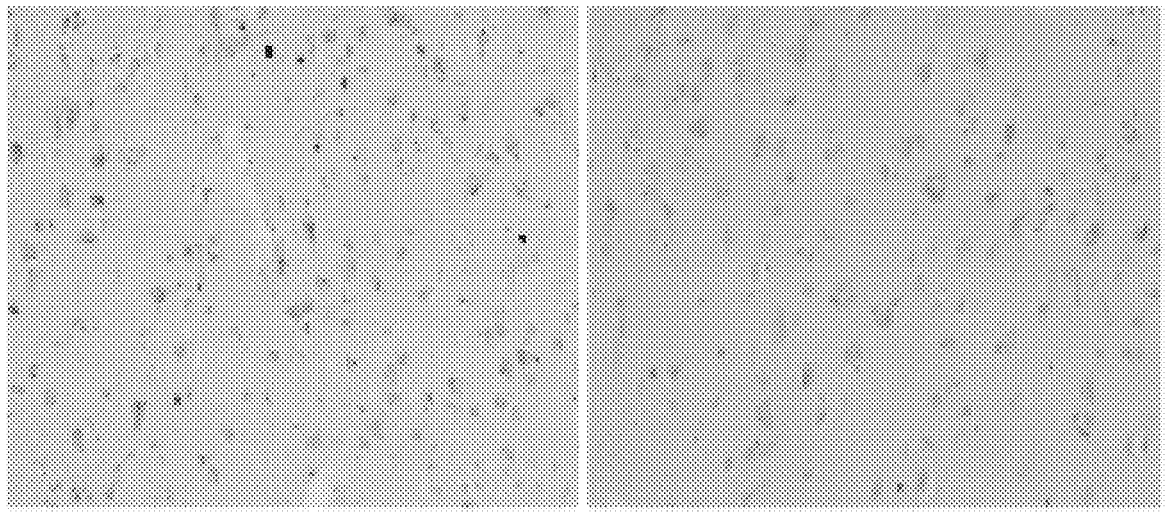
Figure 13D:
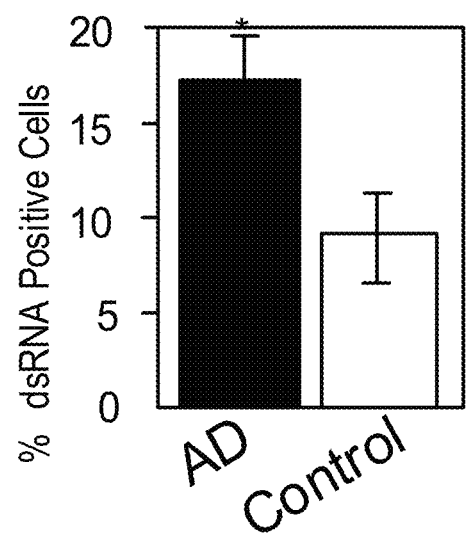

We posited that cytoplasmic dsRNA may trigger induction of MDA5 and PKR in AD patients. TDP-43 inclusions are present in a subset of AD cases and associated with a greater rate of cognitive decline. Both partial loss of function of TDP-43 and overexpression of pathogenic alleles of TDP-43 are associated with the derepression of endogenous retroviral sequences embedded in human genomes (11-13), which may trigger a viral mimicry pathological cascade. Indeed, we found cytoplasmic dsRNA in neurons in the amygdala of cognitively normal individuals with Braak stage I and II tangle deposition as well as demented patients with Braak stage V and VI pathology. Moreover, we found significant greater cytoplasmic dsRNA inclusions in the neurons of frontal lobes of AD patients with severe dementia relative to the neurons of frontal lobes from individuals who were cognitively normal (FIG. 13B-D). The frequency of dsRNA staining exceeded the frequency of TDP-43 inclusions, and were present in peri-nuclear granules.

We have identified cytoplasmic dsRNA in neurons of subsets of ALS and AD patients with TDP-43 cytoplasmic inclusions. Cytoplasmic dsRNA evokes Type I innate immune signaling (14) and is sufficient to mediate neurodegeneration (15). The possible origins of the cytoplasmic dsRNA species in neurons include cell autonomous, e.g. genomic lesions (e.g. C9orf72), genomic inversions (either inherited or acquired somatically as a consequence of aging) (16), viral infection (17), derepression of endogenous retroviruses and transposons (18), and ectopic splicing (19). Moreover, non-cell autonomous processes are possible, e.g. propagation of dsRNA from neighboring or synaptically connected cells via exosomes or direct transfer. Taken together, our findings demonstrated that dsRNA accumulates in the cytoplasm of neurons in ALS and AD and that activation of cytoplasmic dsRNA sensors contribute to the rich tapestry of neurodegenerative processes that underlie clinically-classified disease (20). Inhibition of one or more of these innate immune pathways may slow propagated neurodegeneration and offer clinical benefit, particularly if treatment is initiated at a sufficiently early stage.

References for Example 2

1. S. C. Ling, M. Polymenidou, D. W. Cleveland, Converging mechanisms in ALS and FTD: disrupted RNA and protein homeostasis. Neuron 79, 416-438 (2013).
2. K. A. Josephs et al., Staging TDP-43 pathology in Alzheimer's disease. Acta Neuropathol 127, 441-450 (2014).
3. C. Lagier-Tourenne et al., Targeted degradation of sense and antisense C9orf72 RNA foci as therapy for ALS and frontotemporal degeneration. Proc Natl Acad Sci USA 110, E4530-4539 (2013).
4. J. Cooper-Knock et al., Antisense RNA foci in the motor neurons of C9ORF72-ALS patients are associated with TDP-43 proteinopathy. Acta Neuropathol, (2015).
5. M. Bonin et al., Determination of preferential binding sites for anti-dsRNA antibodies on double-stranded RNA by scanning force microscopy. RNA 6, 563-570 (2000).
6. J. H. Hu, K. Chernoff, S. Pelech, C. Krieger, Protein kinase and protein phosphatase expression in the central nervous system of G93A mSOD over-expressing mice. J Neurochem 85, 422-431 (2003).
7. F. Mouton-Liger et al., Increased cerebrospinal fluid levels of double-stranded RNA-dependant protein kinase in Alzheimer's disease. Biological psychiatry 71, 829-835 (2012).
8. J. Dumurgier et al., Cerebrospinal fluid PKR level predicts cognitive decline in Alzheimer's disease. PloS one 8, e53587 (2013).
9. B. Zhang et al., Integrated systems approach identifies genetic nodes and networks in late-onset Alzheimer's disease. Cell 153, 707-720 (2013).
10. B. C. Dickerson et al., Alzheimer-signature MRI biomarker predicts AD dementia in cognitively normal adults. Neurology 76, 1395-1402 (2011).
11. R. Douville, J. Liu, J. Rothstein, A. Nath, Identification of active loci of a human endogenous retrovirus in neurons of patients with amyotrophic lateral sclerosis. Annals of neurology 69, 141-151 (2011).
12. T. K. Saldi et al., TDP-1, the *Caenorhabditis elegans* ortholog of TDP-43, limits the accumulation of double-stranded RNA. (2014), vol. 33, pp. 2947-2966.
13. W. Li et al., Human endogenous retrovirus-K contributes to motor neuron disease. Sci Transl Med 7, 307ra153 (2015).
14. C. S. McAllister, C. E. Samuel, The RNA-activated protein kinase enhances the induction of interferon-beta and apoptosis mediated by cytoplasmic RNA sensors. The Journal of biological chemistry 284, 1644-1651 (2009).
15. L. Gitlin et al., Essential role of mda-5 in type I IFN responses to polyriboinosinic:polyribocytidylic acid and encephalomyocarditis picornavirus. Proceedings of the National Academy of Sciences of the United States of America 103, 8459-8464 (2006).
16. M. E. Talkowski et al., Sequencing chromosomal abnormalities reveals neurodevelopmental loci that confer risk across diagnostic boundaries. Cell 149, 525-537 (2012).
17. P. Mukherjee, T. A. Woods, R. A. Moore, K. E. Peterson, Activation of the innate signaling molecule MAVS by bunyavirus infection upregulates the adaptor protein SARM1, leading to neuronal death. Immunity 38, 705-716 (2013).
18. M. T. Reilly, G. J. Faulkner, J. Dubnau, I. Ponomarev, F. H. Gage, The role of transposable elements in health and diseases of the central nervous system. The Journal of neuroscience: the official journal of the Society for Neuroscience 33, 17577-17586 (2013).
19. J. P. Ling, O. Pletnikova, J. C. Troncoso, P. C. Wong, NEURODEGENERATION. TDP-43 repression of non-conserved cryptic exons is compromised in ALS-FTD. Science 349, 650-655 (2015).
20. J. S. Rao, M. Kellom, H. W. Kim, S. I. Rapoport, E. A. Reese, Neuroinflammation and synaptic loss. Neurochemical research 37, 903-910 (2012).

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A transgenic mouse whose genome comprises:
a first transgene comprising
a nucleic acid sequence in sense orientation encoding human amyloid precursor protein (APP) that has amino acid substitutions K670N and M671 L operably linked to a tetracycline responsive element (TRE) inducible promoter, an internal ribosome entry sequence (IRES), and a nucleic acid sequence encoding a green fluorescent protein (GFP), and
a nucleic acid sequence in antisense orientation that is complementary to at least part of the nucleic acid sequence encoding the human APP,
a second transgene comprising a nucleic acid sequence encoding tetracycline-controlled transactivator (tTA) operably linked to an olfactory marker protein (OMP) promoter, and an IRES,
wherein induced expression of the first and second transgenes causes increased olfactory neuron degeneration in the mouse as compared to a wild-type mouse.

2. A transgenic mouse whose genome comprises:
a first transgene comprising
a nucleic acid sequence in sense orientation encoding human amyloid precursor protein (APP) that has amino acid substitution M671V operably linked to a tetracycline responsive element (TRE) inducible promoter, an internal ribosome entry sequence (IRES), and a nucleic acid sequence encoding mCherry, and
a nucleic acid sequence in antisense orientation that is complementary to at least part of the nucleic acid sequence encoding the human APP,
a second transgene comprising a nucleic acid sequence encoding tetracycline-controlled transactivator (tTA) operably linked to an olfactory marker protein (OMP) promoter, and an IRES,
wherein induced expression of the first and second transgenes causes increased olfactory neuron degeneration in the mouse as compared to a wild-type mouse.

3. A transgenic mouse whose genome comprises:
a first transgene comprising
a nucleic acid sequence in sense orientation encoding a wild-type human amyloid precursor protein (APP) operably linked to a tetracycline responsive element (TRE) inducible promoter, an internal ribosome entry sequence (IRES), and a nucleic acid sequence encoding a fluorescent protein, and
a nucleic acid sequence in antisense orientation that is complementary to at least part of the nucleic acid sequence encoding the human APP,
a second transgene comprising a nucleic acid sequence encoding tetracycline-controlled transactivator (tTA) operably linked to an olfactory marker protein (OMP) promoter, and an IRES,
wherein induced expression of the first and second transgenes causes increased olfactory neuron degeneration in the mouse as compared to a wild-type mouse.

4. The transgenic mouse of claim 3, wherein the fluorescent marker is GFP or mCherry.

* * * * *